US008501190B2

(12) United States Patent
Prescott et al.

(10) Patent No.: US 8,501,190 B2
(45) Date of Patent: Aug. 6, 2013

(54) **VACCINE AGAINST *CLOSTRIDIUM PERFRINGENS***

(75) Inventors: John Prescott, Guelph (CA);
Raveendra Kulkarni, Guelph (CA);
Valeria Parreira, Guelph (CA); Shayan Sharif, Guelph (CA)

(73) Assignee: The University of Guelph, Guelph, Ontario (CA)

( * ) Notice: Subject to any disclaimer, the term of this patent is extended or adjusted under 35 U.S.C. 154(b) by 333 days.

(21) Appl. No.: 12/666,264

(22) PCT Filed: May 30, 2008

(86) PCT No.: PCT/CA2008/001031
§ 371 (c)(1),
(2), (4) Date: Jun. 11, 2010

(87) PCT Pub. No.: WO2009/000066
PCT Pub. Date: Dec. 31, 2008

(65) Prior Publication Data
US 2010/0255022 A1 Oct. 7, 2010

Related U.S. Application Data

(60) Provisional application No. 60/929,342, filed on Jun. 22, 2007.

(51) Int. Cl.
*A61K 39/00* (2006.01)
*A61K 39/02* (2006.01)
*A61K 39/08* (2006.01)
*A01N 63/00* (2006.01)
*A01N 65/00* (2009.01)

(52) U.S. Cl.
USPC ............... 424/190.1; 424/184.1; 424/234.1; 424/247.1; 424/93.1; 424/93.2; 424/93.4

(58) Field of Classification Search
None
See application file for complete search history.

(56) References Cited

U.S. PATENT DOCUMENTS
7,144,998 B1 * 12/2006 Gibert et al. ................. 536/24.1

FOREIGN PATENT DOCUMENTS
CA 2606180 A1 10/2006

OTHER PUBLICATIONS

Uniprot accession No. Q8XW1 Mar. 1, 2002.*
GenBank accession # CAA35186, Jul. 2006.*
Houghten et al. New Approaches to Immunization, Vaccines 86, Cold Spring Harbor Laboratory, p. 21-25, 1986.*
Colman et al. Research in Immunology 145: 33-36, 1994.*
Ellis, R.W. Chapter 29 of "Vaccines" .Plotkin, S.A. et al. (eds) published by W. B. Saunders company (Philadelphia) in 1988.*
Abbas et al. Cellular and Molecular Immunology 2000 Chapter 15 p. 360-362.*
Algape-Giron, Alberto, et al., 2000, Identification of residues critical for toxicity in *Clostridium perfringens* phospholipase C, the key toxin in gas gangrene, Eur. J. Biochem., 267:5191-5197.
Awad, Milena M., et al., 2001, Synergistic effects of alpha-toxin and perfringolysin O in *Clostridium perfringens*-mediated gas gangrene, Infectection and Immunity, 69:7904-7910.
Banu, Sayera, et al., 2000, Identification of novel VirR/VirS-regulated genes in *Clostridium perfringens*, Molecular Microbiology, 35:854-864.
Ba-Thein, William, et al., 1996, The virR/virS locus regulates the transcription of genes encoding extracellular toxin production in *Clostridium perfringens*, Journal of Bacteriology, 178:2514-2520.
Bennett, Alice M., et al., 1999, Recombinant vaccinia viruses protect against *Clostridium perfringens* alpha-toxin, Viral Immunology, 12:97-105.
Boel, Gregory, et al., 2005, Inhibition of cell surface export of group A Streptococcal anchorless surface dehydrogenase affects bacterial adherence and antiphagocytic properties, Infection and Immunity, 73:6237-6248.
Eaton, Julian T., et al., 2002, Crystal structure of the *C. perfringens* alpha-toxin with the active site closed by a flexible loop region, J. Mol. Biol., 319:275-281.
Efimova, M. G., et al., 1982, Protective properties of theta-hemolysin obtained by affinity chromatography, Zh. Mikrobiol. Epidemiol. Immunobiol., 12:87-92.
Grifantini, R., et al., 2002, Gene expression profile in *Neisseria meningitidis* and *Neisseria lactamica* upon host-cell contact: From basic research to vaccine development, Ann. N. Y. Acad. Sci., 975:202-216.
Heier, B. T., 2001, A field study of naturally occurring specific antibodies against *Clostridium perfringens* alpha-toxin in Norwegian broiler flocks, Avian Dis., 45:724-732.
Ito, A., 1968, Alpha-toxoid of *Clostridium perfringens*: 1. purification and toxoiding of alpha-toxin of *C. perfringens*, Japan J. Med. Sci. Biol., 21:379-391.
Kaldhusdal, M., 2000, Necrotic enteritis: The economical impact of *Clostridium perfringens* is greater than anticipated, World Poultry, 16: 50-51.
Kawsar, H., et al., 2004, Organization and transcriptional regulation of myo-inositol operon in *Clostridium perfringens*, FEMS Microbiol. Lett., 235:289-295.
Keyburn, Anthony L., 2006, The alpha-toxin of *Clostridium perfringens* is not an essential virulence factor in necrotic enteritis in chickens, Infectection and Immunity, 74:6496-6500.
Kulkarni, R. R., 2006, *Clostridium perfringens* antigens recognized by broiler chickens immune to necrotic enteritis, Clinical and Vaccine Immunology, 13:1358-1362.

(Continued)

*Primary Examiner* — Oluwatosin Ogunbiyi
(74) *Attorney, Agent, or Firm* — Knobbe, Martens, Olson & Bear, LLP

(57) ABSTRACT

There is provided a vaccine for controlling *Clostridium perfringens* in animals, and particularly necrotic enteritis in poultry. The vaccine may comprise a *C. perfringens* antigenic polypeptide or variant thereof, a nucleic acid encoding the *C. perfringens* antigenic polypeptide or variant thereof, or a recombinant cell producing the *C. perfringens* antigenic polypeptide or variant thereof.

15 Claims, 22 Drawing Sheets

OTHER PUBLICATIONS

Kulkarni, R.R., et al., 2007, Immunization of broiler chickens against *Clostridium perfringens*-induced necrotic enteritis, Clinical and Vaccine Immunology, 14:1070-1077.

Laemmli, U. K., 1970, Cleavage of structural proteins during the assembly of the head of bacteriophage T4, Nature, 227:680-685.

Ling, E. et al., 2004, Glycolytic enzymes associated with the cell surface of *Streptococcus pneumoniae* are antigenic in humans and elicit protective immune responses in the mouse, Clin. Exp. Immunol., 138:290-298.

Logan, A. J., et al., 1991, Epitope mapping of the alpha-toxin of *Clostridium perfringens*, Infection and Immunity, 59:4338-4342.

Lovland, A., et al., 2004, Maternal vaccination against subclinical necrotic enteritis in broilers, Avian Pathology, 33:83-92.

Madureira, Pedro, et al., 2007, *Streptococcus agalactiae* GAPDH is a virulence-associated immunomodulatory protein, Journal of Immunology, 178:1379-1387.

McCarthy, J. S., et al., 2002, *Onchocerca volvulus* glycolytic enzyme fructose-1,6-bisphosphate aldolase as a target for a protective immune response in humans, Infection and Immunity, 70:851-858.

Modun, Belinda, and Paul Williams, 1999, The staphylococcal transferrin-binding protein is a cell wall glyceraldehyde-3-phosphate dehydrogenase, Infection and Immunity, 67:1086-1092.

Pancholi, V. and G.S. Chhatwal, 2003, Housekeeping enzymes as virulence factors for pathogens, Int. J. Med. Microbiol, 293:391-401.

Pancholi, V. and V. A. Fischetti, 1997, Regulation of the phosphorylation of human pharyngeal cell proteins by group A streptococcal surface dehydrogenase: Signal transduction between streptococci and pharyngeal cells, J. Exp. Med., 186:1633-1643.

Prescott, J. F., 1979, The prevention of experimentally induced necrotic enteritis in chickens by avoparcin, Avian Diseases, 23: 1072-1074.

Shimizu, T., et al., 1994, The virR gene, a member of a class of two-component response regulators, regulates the production of perfringolysin O, collagenase, and hemagglutinin in *Clostridium perfringens*, Journal of Bacteriology, 176:1616-1623.

Shimizu, T., et al., 2002, Complete genome sequence of *Clostridium perfringens*, an anaerobic flesh-eater, Proc. Natl. Acad. Sci. U. S. A., 99:996-1001.

Shimizu, T., et al., 2002, Proteome and transcriptome analysis of the virulence genes regulated by the VirR/VirS system in *Clostridium perfringens*, Journal of Bacteriology, 184:2587-2594.

Sirard, J.C., et al., 1997, A recombinant *Bacillus anthracis* strain producing the *Clostridium perfringens* Ib component induces protection against Iota Toxins, Infect. Immun., 65:2029-2033.

Stevens, D. L. and Amy E. Bryant, 1993, Role of theta toxin, a sulfhydryl-activated cytolysin, in the pathogenesis of clostridial gas gangrene, Clinical Infectious Diseases, 4:S195-9.

Stevens, D. L., et al., 2004, Immunization with the C-domain of alpha-toxin prevents lethal infection, localizes tissue injury, and promotes host response to challenge with *Clostridium perfringens*, Journal of Infectious Diseases, 190:767-773.

Thammapalerd, N., et al., 1996, Pyruvate: Ferredoxin oxidoreductase from Entamoeba histolytica recognized by a monoclonal antibody, Southeast Asian J. Trop. Med. Public Health, 27:63-70.

Thompson, D. R., et al., 2006, Live attenuated vaccine-based control of necrotic enteritis of broiler chickens, Veterinary Microbiology, 113:25-34.

Titball, Richard W., et al., 1993, Biochemical and immunological properties of the C-terminal domain of the alpha-toxin of *Clostridium perfringens*, FEMS Microbiology Letters, 110:45-50.

Williamson, E. D., and R. W. Titball, 1993, A genetically engineered vaccine against the alpha-toxin of *Clostridium perfringens* protects mice against experimental gas gangrene, Vaccine, 11: 1253-1258.

Winram, S. B., and R. Lottenberg, 1996, The plasmin-binding protein plr of group A streptococci is identified as glyceraldehyde-3-phosphate dehydrogenase, Microbiology, 142 (8):2311-2320.

Konjufca, V., et al., 2006, A recombinant attenuated *Salmonella enterica* serovar Typhimurium vaccine encoding *Eimeria acervulina* antigen offers protection against *E. acervulina* challenge, Infecttion and Immunity, 74(12):6785-96.

Galan, J. E., et al., 1990, Cloning and characterization of the asd gene of *Salmonella typhimurium*: use in stable maintenance of recombinant plasmids in *Salmonella* vaccine strains, Gene, 94(1):29-35.

Curtiss, R./3rd, et al., 1990, Stabilization of recombinant avirulent vaccine strains in vivo, Res. Microbiol., 141 (7-8):797-805.

Zekarias, Bereket, et al., 2008, Recombinant attenuated *Salmonella* expressing the carboxy-terminal domain of alpha-toxin from *Clostridium perfringens* induces protective responses against necrotic enteritis in chickens, Clin. Vaccine Immunology, Mar. 12: Epub ahead of print.

Wyszynska, A., et al., 2004, Oral immunization of chickens with avirulent *Salmonella* vaccine strain carrying *C. jejuni* 72Dz/92 cjaAgene elicits specific humoral immune response associated with protection against challenge with wild-type *Campylobacter*, Vaccine, 22(11-12):1379-89.

Kang, H.Y., et al., 2002, Immune responses to recombinant pneumococcal PspA antigen delivered by live attenuated *Salmonella enterica* serovar *Typhimurium* vaccine, Infection and Immunity, 70 (4): 1739-49.

Oliveira, Aline F., et al., 2007, Oral administration of a live attenuated *Salmonella* vaccine strain expressing the VapA protein induces protection against infection by *Rhodococcus equi*, Microbes and Infection, 9(3): 382-90.

* cited by examiner

Figure 1

(SEQ ID NO:1)

MNKRKIAAIILATMITNLSATTIDVLAQELNTKNNSKVEVSHDDESHQARVSKFDLYNSDKLDAYNQEFQI
NRSNIKSITNNGGKYNSSTIDKAIDGNLETHWETGKPNDSNFTNEVVVTFNEITNIDRIVYSARRDSARGK
GFAKEFEIYASLKDEGDDFNLVSSGEYTESTRDLVEIKFNPTDFKRLKFKFKKKADQNWASSAEFMFYKEDK
LNEKFNGLFTDSSMNKVSEEFNTLEKLNAFENELKDHPMYDLYKEGLNNARAILTETSENPTKATLGQITY
NLNDDYNNQYRMPYTNIKSIKNNGRHYAAQNIEKAIDNDVNTYWETGTLNSSSFNNEVEVEFNDLVTLDRI
VYGSRQSDLKGFAEEVYIYASRTSKGDTYKLVATGAHEATKGLVEAKFEPTEFKRVKFKFKKKSKQNSATLN
ELMFYKPDEVYSSIPKLFTDGTMSELSEEFNSLEKINAFKEKAKNHPLYNDFKETIDLAESLISNPRKEDV
LELEMRGDSISEAKKRKVWNFQDWQITGLSARAGDKITVYVDVAEGDPTPTLLYKQSLTQHGGATSFQLKP
GKNEITIPEINYESNGIPKDVIQGGDLFFTNYKSDSQKRAPKVRIEGASKYPVFILGKSDENEVMKELEAY
VEKIKAEPKTTPNIFAVSSNKSLEFVQATYALDWYKKNNKTPKYTAEQWDQYIADAMGFWGFDNSKDVNSD
FNFRIMPMVKNLSGGAFMNAGNGVIGIRPGNQDAILAANKGWGVAHELGHNFDTGGRTIVEVTNNMMPLFF
ESKYKTKTRITDQNIWENNTYPKVGLDDYSNNELYNKADSTHLAQLAPLWQLYLYDNTFYGKFERQFRERD
FGNKNREDIYKSWVVAASDAMELDLTEFFARHGIRVDDDKVKEDLAKYPKPDKKIYYLNDLAMNYKGDGFTD
NAKVSVSTSGSNGNIKLSFSVDDENKDNILGYEIRRDGKYVGFTSNDSFVDTKSNLDEDGVYVTPYDRKL
NTLNPIEVNALQPTLSVNPVITLALGEEFNEEEYIVAKDIKGNSLSESVKVKSSNVNTSKVGEYEVLYSLE
DSKGNEYTKTSKVNVVSRKEYMSDLTPKQSSNGWGTVRKDKSISGGVIGLTRDGDFVDYNKGLGLHSNAEY

Figure 1(continued)

```
VYDLEGKDYDYFESYVGVDKAMSSRPASSVIFKVLVDGEEKFNSGVMRSTTPQKYVKVDVKNAKELKLIVN
DAGDGDSSDHASFGDAKLATLSSKPIIKGENLAYNMDEKVDLMKGITATDIEDGNITSKIQIKSSDFVEGK
SGIFKVVYSVTDSDGLTSECSRTIAVTDKETQLSDLNWKSATIGSGSVRKDRAVSGNQIRLLNEDNSVQTF
AKGIGTHSYSEIVYNSEGYDIFDTWVGIDRHVADKKVSSVKFKVYVDGELKAETDVMRIDTPKKRLVVDVR
NSKEIKLVVDVADNGNTWDHADWADAKFRNLAEYDTTELNKALEEAKKLDLNNYTEESFEALKNAISKGEE
ALLSKDKETINSALEELNKAMDSLVKVDLNAVINIPDKYLLKSIQNQLNKTGDITLGDMYSLTTLTLSGVE
DLSGLENAKNLETLNMDYNEVKDLRPLSKLKKLNTLNAQEQFIAAGELKPSNGKVIGDSKVYNREGKNVAK
TIRVVDKNGNTILEQDAKDEFTINTKDLSSGLYGVHVLFEDEGFSGVMFYLFNV
```

Figure 2

(SEQ ID NO:2)

MAMRKMKTMDGNTAAAYISYAFTDVAAIFPITPSSPMAEWVDENSARGLKNIFGQPVKVMEMQSEAGAAG
AVHGSLQAGALTTYTASQGLLLMIPNMYKIAGELLPSVFHVSARALATSALNIFGDHQDVMAARQTGFA
MLAEGSVQEVMDLSAVAHLAALKARIPFVNFFDGFRTSHEIQKVELLQYDELKELVDMEAVEEFRRRALN
PNKPVTRGTAQNPDIYFQEREAVNKFYDAVPEIVESYMKEITKLTGREYNCFDYYGAADAERVIVAMGSV
TDLIEETVDYLNAKGEKVGLIKVRLFRPFSNERLIKAMPKTVKKVAVLDRTKEPGAAGEPLYLEVKNAFY
GLENAPVIVGGRFGLGSKDTVPADIVAVYENLNKEDAKNGFTLSIVDDVTNTSLEPVGDIDTTPEGTKAC
KFWGLGSDGTVGANKSAIKIIGDHTDMYAQGYFAYDSKKSGGVTISHLRFGKQPIKSPYLINKADFVACH
NQSYVNKYFVLDGLKKNGTFLLNTIWTPEEVAEHLPASYKRFLAENNIKFYTLNAVKIAQEVGLGGRINM
IMQSAFFKLANIIPVEDAVKYLKDAVVTSYGKKGEKVVNMNHAAIDKGIDAIVEITVPAEWANAKDEVVE
AKEVPAFIKNIVEPMNRLEGDKLPVSAFNGMEDGTFEPGTAAYEKRGIGINIPEWIADNCIQCNQCAYVC
PHATIRPFLLTEEEAKNAPASTKLVAAKALKTEEPMQFTMAVSTLDCTGCNCAQVCPAKEKALVMKPQH
TQEDQIEAWDYCVNDVVPKKNPMNKNTVKGSQFEQPLFEFSGACAGCGETPYAKLITQLFGDRMMIANAT
GCSSIWGGSAPSTPYTTNHNGHGPAWANSLFEDNAEFGLGMFLGVKAIRERLVDLAGKAIEAGVKPEAKE
ALEAWIAEVDNGEGTRDRADAVVAALQGETNEFAKEILKDQDYLAKRSQWIFGGDGWAYDIGYGGVDHVL
ASGEDVNILVMDTEIYSNTGGQASKSTPTAAIAKFAAAGKRTKKKDLGMMAMSYGYVYVAQIAMGADKNQ
TLKAIAEAEAYKGPSLIIAYAPCISHGLKAGMGNSQLEEKRAVECGYWAMYRFNPMLKETGKNPFSLDSK
EPTGDFREFIMGEVRYAALAKAFPEAAEALFEKTERDAKERLENYKKLAAN

Figure 3

(SEQ ID NO:3)

MARQYPLEKFRNFGIMAHIDAGKTTTTERILFYTGRNHKIGETHDGASTMDWMAQEQERGITITSAATTC
FWKGYELNIIDTPGHVDFTVEVERSLRVLDGAVTVLDAKSGVEPQTETVWRQADKYGVPRMIYVNKMDAT
GADYYNCINTVRERLQANAVAIQIPIGQEDQFQGMVDLLTNQAIIFKDDLGKDIEVGEVPADLADKAEEY
RAAMIEAIAETDEELMMKYLEGEELTLEELKVALRKATINNEIIPVICGSSYKNKGVQQMIDGVVDYLPS
PLDIPAVKGTNLDGEEVREASDDAPMSALAFKIATDPFVGRLAFTRVYSGVLESGSYVLNSTKGKKERI
GRLVKMHANSREEVESLEAAELGAVIGLKNTTTGDTLCTEAAPIILEKMEFPEPVISIAIEPKTKAGQEK
MGIALSKLAEEDPTFKTWTDQETGQTIIAGMGELHLDIIVDRLQREFKVECNVGAPQVAYKETIKKAVEA
EAKFARQSGGRGQYGHCKIEMIPTEGEYEFENAIVGGAIPREYIPAVDNGIREAAESGIIAGYPVINFKI
RLFDGSYHDVDSSEMAFKIAGSMAFKNAMAKADAVLLEPIMKVEITVPEEYMGDVIGDVNSRRGRMEGMD
SRNGAQIIRAFIPLSEMFGYATALRSRTQGRGTYAMEFDHYDDVPKSIQEEVAGKKNK

Figure 4

(SEQ ID NO:4)

MIRFKKTKLIASIAMALCLFSQPVISFSKDITDKNQSIDSGISSLSYNRNEVLASNGDKIESFVPKEGKK
TGNKFIVVERQKRSLTTSPVDISIIDSVNDRTYPGALQLADKAFVENRPTILMVKRKPININIDLPGLKG
ENSIKVDDPTYGKVSGAIDELVSKWNEKYSSTHTLPARTQYSESMVYSKSQISSALNVNAKVLENSLGVD
FNAVANNEKKVMILAYKQIFYTVSADLPKNPSDLFDDSVTFNDLKQKGVSNEAPPLMVSNVAYGRTIYVK
LETTSSSKDVQAAFKALIKNTDIKNSQQYKDIYENSSFTAVVLGGDAQEHNKVVTKDFDEIRKVIKDNAT
FSTKNPAYPISYTSVFLKDNSVAAVHNKTDYIETTSTEYSKGKINLDHSGAYVAQFEVAWDEVSYDKEGN
EVLTHKTWDGNYQDKTAHYSTVIPLEANARNIRIKARECTGLAWEWWRDVISEYDVPLTNNINVSIWGTT
LYPGSSITYN

Figure 5

(SEQ ID NO:5)

MVKVAINGFGRIGRLALRLMIDNPEFEVVAINDLTDAKTLAHLFKYDSAQGRFNGEIEVKEGAFVVNGKE
IKVTAKSNPAELPWGELGVDVVLECTGFFASKEKASAHLTAGAKKVVISAPAGNDLPTVVYNVNHDILDG
SEDVISGASCTTNCLAPMAKALNDNFGLNKGFMTTIHAYTNDQNTLDAPHKKGDLRRARAAAANIVPNST
GAAKAIGLVIPELAGKLDGNAQRVPVITGSLTELVCTLDKKVTVEEVNAAMKAASNESFGYTEDPIVSSD
VIGISFGSLFDATQTKIMEVDGQQLVKVASWYDNEASYTNQLIRTLKCLVSK

Figure 6

(SEQ ID NO:6)

MALVNAKEMLNKAREGKYAVGQFNINNLEWTKAILLTAQENNSPVILGVSEGAAKYMCGFKTIVGMVNGM
LEELKITVPVALHLDHGSYQGAIDAMDAGFSSVMFDGSHYSIEENIVKTKEIINLAAAKNVSVEAEVGSI
GGEEDGVVGAGEIADPAECKQIAELGVTMLAAGIGNIHGKYPANWAGLNFEALANIKAATGDMPLVLHGG
TGIPSDMIAEAISLGVSKINVNTECQLSFAEATRKYIEAGKDLEGKGFDPRKLLNPGFEAIKATVKEKME
LFGSVNRA

Figure 18

SKDVNSDFNFRIMPMVKNLSGGAFMNAGNGVIGIRPGNQ
DAILAANKGWGVAHELGHNFD (SEQ ID NO:7)

YDNTFYGKFERQFRERDFGNKNREDIYKSWVVAASDAME
LDLTEFFARHGIRVDDDKVKEDLAKYPKPDKKIYYLNDLA
(SEQ ID NO:8)

IKLSFSVDDENKDNILGYEIRRDGKYVGFTSNDSFVDTKS
NLDEDGVYVVTPYD (SEQ ID NO:9)

Figure 19

GYFAYDSKKSGG (SEQ ID NO:10)

SYVNKYFVLDGL (SEQ ID NO:11)

KDEVVEAKEVPA (SEQ ID NO:12)

AKEVPAFIKNIV (SEQ ID NO:13)

AYVCPHATIRPF (SEQ ID NO:14)

Figure 20A

TTCTGGGATTTGATAACTCAAAAGATGTTAATTCAGATTTAATTTTAGAATAATGCCTATGG
TTAAAAACCTTAGTGGTGGAGCATTCATGAATGCTGGAAATGGTGTTATAGGTATAAGACCTGG
AAATCAGGATGCAATACTTGCAGCTAATAAAGGATGGGGTGTTGCTCATGAACTTGGACATAAC
TTTGATACAGGCGGAAGAACCATAGTAGAAGTAACAAATAATATGATGCCATTATTCTTTGAGT
CTAAATATAAAACTAAAACAAGAATAACTGACCAAAACATATGGGAAAACAATACTTACCCTAA
AGTTGGCTTAGATGATTATTCTAATAATGAGTTATATAATAAGGCTGATAGTACTCATTAGCT
CAGTTAGCGCCATTATGGCAATTATATTTATATGATAATACTTTCTATGGAAAGTTTGAAAGAC
AGTTTAGAGAGAAAGAGATTTTGGAAATAAAAATAGAGAAGATATATATAAATCTTGGGTTGTGGC
AGCGTCAGATGCTATGGAGTTAGATTTAACTGAGTTCTTTGCAAGACATGGTATTCGTGTTGAT
GATAAGGTTAAGGAGGATTTAGCTAAGTATCCAAAGCCTGATAAATGCAAAGGTATCTGTAAGTACAAG
ATTAGCAATGAATTATATAAAGGTGATGGGATTTACGGATAATGCAAAGGTATCTGTAAGTACAAG
TGGTTCAAATGGTAATATAAAACTTTCATTCTCAGTAGATGATGAAAATAAAGATATATACTT
GGATATGAAATACGCAGAGATGGAAAGTATGTAGGATTTACTTCTAATGATAGCTTTGTTGATA
CTAAATCTAATTTAGATGAGGATGGTGTATATGTAGTAACACCATATGATAGAAAGTAAATAC
CTTAAATCCAATAGAGGTAAATGCATTGCAACCAACTTTATCTGTAAACCCAGTGATTACACTA
GCTTTAGGTGAGGAG     (SEQ ID NO:15)

Figure 20B

FWGFDNSKDVNSDFNFRIMPMVKNLSGGAFMNAGNGVIGIRPGNQDAILA

ANKGWGVAHELGHNFDTGGRTIVEVTNNMMPLFFESKYKTKTRITDQNIW

ENNTYPKVGLDDYSNNELYNKADSTHLAQLAPLWQLYLYDNTFYGKFERQ

FRERDFGNKNREDIYKSWVVAASDAMELDLTEFFARHGIRVDDKVKEDLA

KYPKPDKKIYYLNDLAMNYKGDGFTDNAKVSVSTSGSNGNIKLSFSVDDE

NKDNILGYEIRRDGKYVGFTSNDSFVDTKSNLDEDGVYVVTPYDRKLNTL

NPIEVNALQPTLSVNPVITTALGEE          (SEQ ID NO:16)

US 8,501,190 B2

VACCINE AGAINST *CLOSTRIDIUM PERFRINGENS*

This application is U.S. National Phase of International Application PCT/CA2008/001031, filed May 30, 2008 designating the U.S., and published as WO 2009/000066 on Dec. 31, 2008, which claims priority to U.S. Provisional Application No. 60/929,342 filed Jun. 22, 2007.

REFERENCE TO SEQUENCE LISTING, TABLE, OR COMPUTER PROGRAM LISTING

The present application incorporates by reference the sequence listing submitted as an ASCII text filed via EFS-Web on Sep. 21, 2012. The Sequence Listing is provided as a file entitled 14025218.txt, created on Sep. 21, 2012, which is 47.0 Kb in size.

FIELD OF INVENTION

The invention relates to the production of a vaccine. More specifically, the invention provides a vaccine for controlling *Clostridium perfringens* in animals.

BACKGROUND OF THE INVENTION

*Clostridium* are characterized as spore-forming, anaerobic, Gram positive bacilli. The species, *Clostridium perfringens*, can be subdivided into subspecies. Five subspecies have been described. These subspecies are generally known as "type" A-E. All subspecies produce several toxins, both major and minor toxins. The four major toxins are the alpha, beta, epsilon and iota toxin. All *C. perfringens* types produce the alpha-toxin. The beta-toxin is produced by *C. perfringens* types B and C. In addition, a range of minor toxins is produced by all *C. perfringens* types.

One or more of these various toxins can play a role in *C. perfringens* related pathogenesis. Type A is known to be pathogenic for various birds, man, cows and pigs. Type B is mainly pathogenic for lamb, sheep and goat, and causes "lamb dysentery" and haemorrhagic enteritis. Type C is pathogenic for man, sheep, calf, lamb, pig, and bird. *C. perfringens* can cause "struck", haemorrhagic enteritis, necrotic enteritis and enterotoxemia.

Necrotic enteritis (NE) is an economically important enteric disease of birds, for example poultry, caused by *Clostridium perfringens*. The disease is usually controlled by antimicrobial drugs administered at prophylactic doses either in water or feed. However, there is concern about the routine prophylactic use of antimicrobial drugs in food animal production because of their contribution to resistance problems. If antimicrobial drugs were banned for such purposes in North America, there might be an increase in NE in poultry, for example chicken flocks, as has happened in Scandinavia (12).

Although vaccination offers an alternative approach to antimicrobial drugs in control of the disease, very little is known about immunity to NE. However, there has been considerable work on immunity to *C. perfringens* in other circumstances, since it is a cause of gas gangrene in people. This has identified the alpha-toxin, a phospholipase C exoenzyme, both as a major virulence factor and as an important immunogen. For example, a genetically engineered vaccine inducing alpha-toxin (amino acids 247-370) serum antibodies was shown by Williamson and Titball (34) to neutralize hemolytic activity of the toxin and to provide protection against *C. perfringens* in mice. Bennett et al. (5) showed that a recombinant Vaccinia virus vector expressing the non-toxic C-domain region of the alpha-toxin protein provided antibody-mediated protection against experimental toxin challenge. More recently, Stevens et al. (30) showed significant prevention of gas gangrene in mice by immunization using the C-terminal domain of the alpha-toxin (amino acids 247-370). In addition, there is evidence based on naturally occurring antibodies or maternal vaccination that antibodies to alpha-toxin are involved in immunity to NE (10,19). However, the importance of alpha-toxin or any other protein in immunity to NE in birds, for example chickens, remains to be demonstrated, and one study has shown the immunizing effects of alpha-toxin minus mutants (32). A recent study also demonstrated that an alpha-toxin minus mutant produced NE experimentally in chickens, demonstrating that factors other than alpha-toxin are important in the pathogenesis of NE (14). Other studies have shown that the immunizing ability to protect against NE was associated with virulent rather than with avirulent *C. perfringens* (32).

While the prior art has demonstrated some immunizing effect of whole-cell *C. perfringens* in chickens, the basis of this immunity is poorly understood. NE is usually controlled by antimicrobial drugs but, if these are unavailable or not used, there is currently no other simple way to control infection. Therefore, there is a need for novel vaccine for controlling *Clostridium perfringens* in birds.

An object of an aspect of the present invention is to provide a novel vaccine for controlling *Clostridium perfringens* in birds.

SUMMARY OF THE INVENTION

In an aspect, there is provided a vaccine for controlling *C. perfringens* in an animal comprising an isolated nucleic acid molecule which comprises a nucleic acid sequence that encodes a *C. perfringens* secreted antigenic polypeptide or a variant thereof.

In another aspect, there is provided a vaccine for controlling *C. perfringens* in an animal comprising an isolated *C. perfringens* secreted antigenic polypeptide or a variant thereof.

In yet another aspect, there is provided a vaccine for controlling *C. perfringens* in an animal comprising a recombinant cell producing an isolated *C. perfringens* secreted antigenic polypeptide or a variant thereof.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

The present invention will become more fully understood from the detailed description given herein and from the accompanying drawings, which are given by way of illustration only and do not limit the intended scope of the invention.

FIG. 1 shows an amino acid sequence of Hypothetical Protein (HP) of *C. perfringens* Strain 13, GenBank Accession #18144943 (SEQ ID NO:1).

FIG. 2 shows an amino acid sequence of Pyruvate ferredoxin oxidoreductase (PFOR) of *C. perfringens* Strain 13, GenBank Accession #18311043 (SEQ ID NO:2). The underlined portion corresponds to the amino acid sequence of a fragment of PFOR designated as truncated PFOR (tPFOR).

FIG. 3 shows an amino acid sequence of Elongation factor-G (EF-G) of *C. perfringens* Strain 13, GenBank Accession #18311390 (SEQ ID NO:3).

FIG. 4 shows an amino acid sequence of Perfringolysin O of *C. perfringens* Strain 13, GenBank Accession #18143820 (SEQ ID NO:4).

FIG. 5 shows an amino acid sequence of Glyceraldehyde 3-phoshate dehydrogenase (GPD) of *C. perfringens* Strain 13, GenBank Accession #18144966 (SEQ ID NO:5).

FIG. 6 shows an amino acid sequence of Fructose biphosphate aldolase (FBA) of *C. perfringens* Strain 13, GenBank Accession #18310332 (SEQ ID NO:6).

FIG. 7 shows recombinant *C. perfringens* histidine-tagged proteins purified from *Escherichia coli* cells. (A) Coomassie stained purified proteins (B) Reactivity of purified proteins to immune serum from chickens immune to necrotic enteritis. In each panel, Lane 1-Alpha-toxin (45 kDa), Lane 2—GPD of FIG. 5 (40 kDa), Lane 3—FBA of FIG. 6 (35 kDa), Lane 4—tPFOR of FIG. 2 (67 kDa), Lane 5—HP of FIG. 1 (90-100 kDa) and Lane M—Molecular mass standards.

FIG. 8 shows a summary of mean lesion scores of immunized broiler chicken groups challenged with *C. perfringens* infected feed, together with the concurrent unimmunized controls. VC-vehicle-only controls, A-tox—alpha-toxin, FBA—Fructose 1,6-biphosphate aldolase, GPD—Glyceraldehyde 3-phosphate dehydrogenase, tPFOR—Truncated pyruvate:ferredoxin oxidoreductase, HP-Hypothetical protein, Sup—culture supernatant of *C. perfringens*, G+H-combination of GPD and HP, Exp—Experiment. +-birds in this group were challenged for 3 days and autopsied on day 6. ++-birds in this group were given a severe challenge. *-immunized group that had significantly fewer chickens with lesions compared to unimmunized vehicle-only controls; Fisher's exact test, $p<0.05$.

FIG. 9 shows serum IgY ELISA titres of broiler chickens immunized intramuscularly with *C. perfringens* purified proteins. Serum collected at three time-points; Day 0—Pre-immunization titre, Day 10—Mid-experiment, Day 20-Pre-challenge titre. FBA—Fructose 1,6-biphosphate aldolase, GPD—Glyceraldehyde 3-phosphate dehydrogenase, tPFOR—Truncated pyruvate:ferredoxin oxidoreductase, HP-Hypothetical protein, Exp—Experiment; (*) to designate significant titre values when compared to pre-immunization titres, $p<0.05$.

FIG. 10 shows intestinal IgY and IgA ELISA titres of broiler chickens immunized intramuscularly with *C. perfringens* purified proteins. Samples analyzed were from pooled intestines collected from at least 10 chickens in each group. FBA—Fructose 1,6-biphosphate aldolase, GPD—Glyceraldehyde 3-phosphate dehydrogenase, tPFOR—Truncated pyruvate: ferredoxin oxidoreductase, HP—Hypothetical protein, Exp—Experiment.

FIG. 11 shows B-cell epitope mapping of Hypothetical Protein (HP). Based on the primary sequence of HP, a total of 169 peptides of 12 amino acids length, offset by 6 residues were synthesized as spots on a cellulose-derived matrix and reacted with polyclonal chicken immune serum (A). The membrane was visualized under a Molecular light imager and each black spot represents a reactive peptide. The quantified signal of each spot was obtained using Win Light Software and the value was expressed as relative percentage of signal intensity (B).

FIG. 12 shows B-cell epitope mapping of Pyruvate:ferredoxin oxidoreductase (PFOR). Based on the primary sequence of PFOR, a total of 94 peptides of 12 amino acids length, offset by 6 residues were synthesized as spots on a cellulose-derived matrix and reacted with polyclonal chicken immune serum (A). The membrane was visualized under a Molecular light imager and each black spot represents a reactive peptide. The quantified signal of each spot was obtained using Win Light Software and the value was expressed as relative percentage of signal intensity (B).

FIG. 13 shows expression of *C. perfringens* genes by *S. Typhimurium* χ9241 vaccine vector. Total proteins expressed by recombinant *Salmonella* were separated on a 12% SDS-PAGE gel, transferred onto nitrocellulose membranes and reacted with immune serum collected from previously immunized, protected birds. Lanes 1, 3 and 5, *S. Typhimurium* χ9241 (pYA3342); Lane 2, *S. Typhimurium* χ9241 (pYA3342-fba); Lane 4, *S. Typhimurium* χ9241 (pYA3342-tPFOR); Lane 6, *S. Typhimurium* χ9241 (pYA3342-tHP), Lane M—Molecular weight standards. Arrows indicate the protein expressed by recombinant *Salmonella*.

FIG. 14 shows isolation of recombinant *S. Typhimurium* χ9241 after infection. Isolation of *S. Typhimurium* carrying pYA3342, pYA3342-fba, pYA3342-tPFOR or pYA3342-tHP plasmids from broiler chicken tissues at different times following a single oral dose of $1.2\times10^9$ CFU/bird. Tissues were collected from 3 birds at each time.

FIG. 15 shows serum and intestinal antibody responses of broiler chickens to *C. perfringens* antigens, immunized with recombinant *Salmonella* χ9241 carrying pYA3342, pYA3342-fba, pYA3342-tPFOR or pYA3342-tHP plasmids, as detected by Western-blot. Pooled serum IgY (panel-A) and intestinal IgY (panel-B) and IgA (panel-C) responses of immunized birds to *C. perfringens* antigens. Lane 1—FBA, Lane 2—tPFOR, Lane 3—tHP. Molecular weight standards are given in kilo daltons. FBA—fructose-biphosphate aldolase, tPFOR—truncated pyruvate:ferredoxin oxidoreductase, tHP—truncated Hypothetical protein. Arrow indicates a weak reactive band of tHP.

FIG. 16 shows serum IgY responses of broiler chickens to *Salmonella* and *C. perfringens* antigens, immunized with recombinant *Salmonella* χ9241 carrying pYA3342, pYA3342-fba, pYA3342-tPFOR or pYA3342-tHP plasmids, as determined by ELISA. Birds were immunized orally on days 0 (week-0) and 14 (week-2) and serum samples were collected at Weeks 0, 2 and 4. Whole cell lysates and purified antigens were used as coating antigens to assess anti-*Salmonella* and anti-*C. perfringens* responses, respectively. FBA—fructose-biphosphate aldolase, tPFOR—truncated pyruvate: ferredoxin oxidoreductase, tHP-truncated Hypothetical protein. (*) indicate significant titer values when compared to week 0 titers, $p<0.05$.

FIG. 17 shows intestinal IgY and IgA responses of broiler chickens to *Salmonella* and *C. perfringens* antigens immunized with recombinant *Salmonella* χ9241 carrying pYA3342, pYA3342-fba, pYA3342-tPFOR or pYA3342-tHP plasmids, as determined by ELISA. Birds were immunized orally on days 0 (week-0) and 14 (week-2) and intestinal scrapings/washings were collected at Necropsy (Week-5). Whole cell lysates and purified antigens were used as coating antigens to assess anti-Salmonella and anti-*C. perfringens* responses, respectively. FBA-fructose-biphosphate aldolase, tPFOR—truncated pyruvate:ferredoxin oxidoreductase, tHP—truncated Hypothetical protein.

FIG. 18 shows the amino acid sequence of three immunoreactive fragments of HP (SEQ ID NO:7,8,9).

FIG. 19 shows the amino acid sequence of five immunoreactive fragments of tPFOR (SEQ ID NO:10,11,12,13,14).

FIG. 20 shows the (A) nucleic acid sequence (SEQ ID NO:15) and (B) amino acid sequence (SEQ ID NO:16) of a fragment of HP designated truncated HP protein (tHP).

DETAILED DESCRIPTION OF THE PREFERRED EMBODIMENTS

Figure 7:
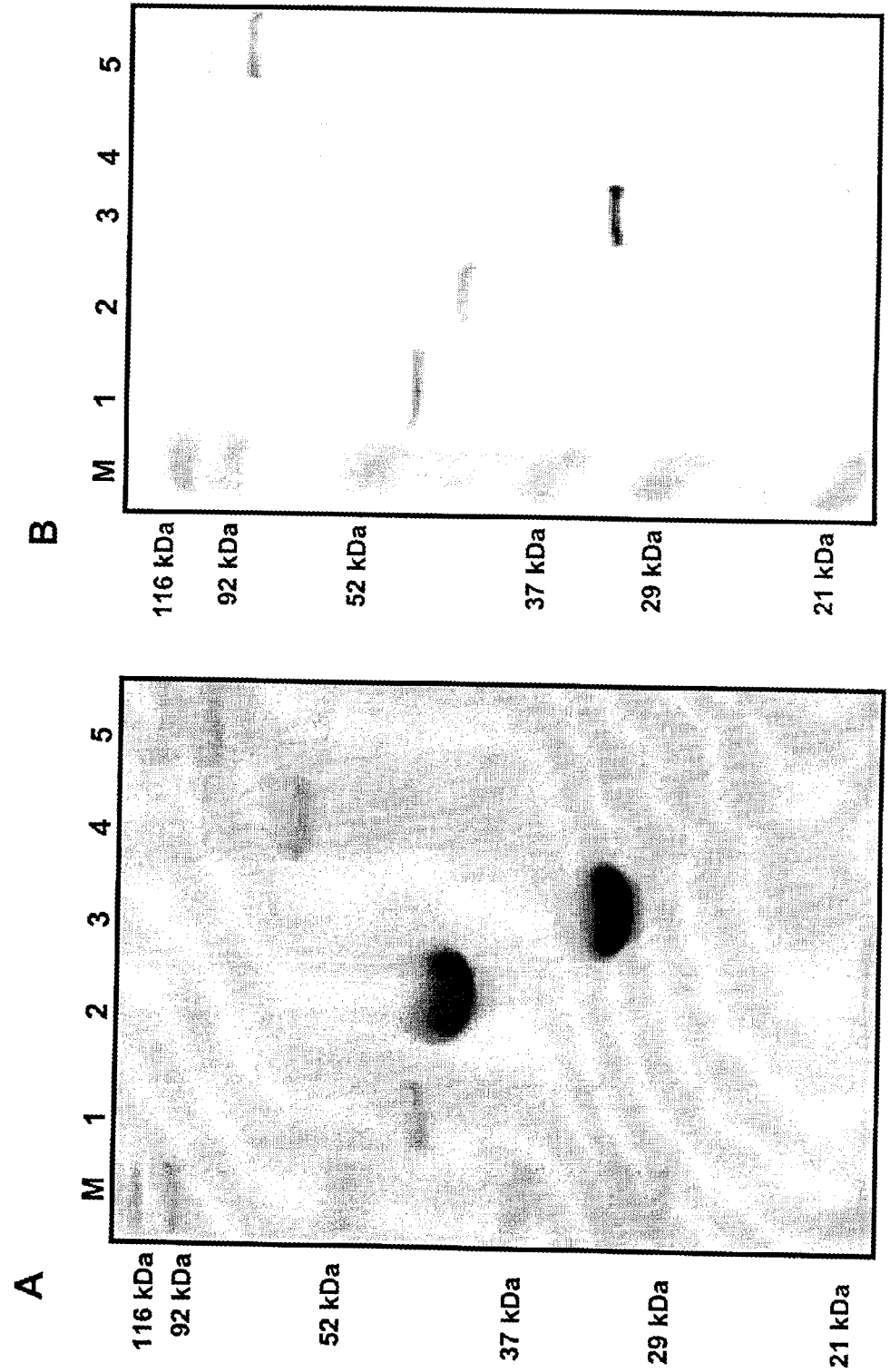

A vaccine is a preparation which is used to confer an immunoprotective effect against a disease in an animal. A vaccine typically acts against a disease by inducing a specific immune response to an antigen associated with a pathogen or disease state, for example, a micro-organism, an epitope in a protein or other molecule, or a class of cells. A vaccine can be prophylactic (for example, to prevent or ameliorate the effects of a future infection or proliferation of a pathogen or undesired cell type), or therapeutic (for example, vaccines to ameliorate the effects of an established infection or proliferation of a pathogen or undesired cell type).

A vaccine is provided for controlling *Clostridium perfringens* in animals. The vaccine may comprise a *C. perfringens* antigenic polypeptide or variant thereof, a nucleic acid molecule encoding the *C. perfringens* antigenic polypeptide or variant thereof, or a recombinant cell producing the *C. perfringens* antigenic polypeptide or variant thereof. Administration of the vaccine to a subject can confer an immunoprotective effect to the subject against *C. perfringens*. The vaccine may be for prophylactic, therapeutic, or both prophylactic and therapeutic treatment. The vaccine can control *C. perfringens* by reducing or preventing infection or proliferation of *C. perfringens* in an animal.

The vaccine will typically comprise an isolated *C. perfringens* secreted antigenic polypeptide or variant thereof, an isolated nucleic acid molecule encoding the *C. perfringens* secreted antigenic polypeptide or variant thereof, or a recombinant cell producing the *C. perfringens* secreted antigenic polypeptide or variant thereof.

An antigenic polypeptide may be provided by any source or method, for example, natural isolate or recombinant or synthetic origin or suitable combinations thereof. An antigenic polypeptide may react immunologically with the sera of subjects suffering from a *C. perfringens* infection. Administration of the antigenic polypeptide to a subject can confer an immunoprotective effect to the subject against *C. perfringens*. The antigenic polypeptide may be of any length provided that the immunoprotective activity is maintained. The sequence of the antigenic polypeptide may be based on a complete or partial naturally occurring amino acid sequence of a polypeptide that naturally occurs in virulent *C. perfringens* type A. An antigenic polypeptide may be used either singly or in combination with other polypeptides, antigenic or otherwise, in the preparation of a vaccine. A polypeptide refers to a chain of amino acids, for example peptides, oligopeptides, or proteins, having a biological function, and does not refer to a specific length of the chain.

An isolated *C. perfringens* antigenic polypeptide is a polypeptide that has been identified and separated and/or recovered from at least one component of its natural environment. The isolated polypeptide will typically have been purified by at least one purification step, and, in some embodiments purification may be achieved (1) to a degree sufficient to obtain at least 15 residues of N-terminal or internal amino acid sequence by use of a sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the *C. perfringens* antigenic polypeptide natural environment will not be present. An isolated polypeptide may be produced by synthetic or recombinant techniques, for example as described in J. Sambrook, E. F. Fritsch, and T. Maniatis, 1989, Molecular Cloning: A Laboratory Manual, Second Edition, Books 1-3, Cold Spring Harbor Laboratory Press. An isolated polypeptide produced as a result of recombinant techniques may be referred to as a recombinant polypeptide.

A nucleic acid encoding an antigenic polypeptide may be any nucleic acid molecule of, for example. cDNA, genomic DNA, synthetic DNA or RNA origin or suitable combinations thereof. Administration of the nucleic acid encoding an antigenic polypeptide to a subject can confer an immunoprotective effect to the subject against *C. perfringens*. The nucleic acid may be of any length provided that the immunoprotective activity is maintained by the encoded antigenic polypeptide. The sequence of the nucleic acid encoding an antigenic polypeptide may be based on a complete or partial naturally occurring nucleic acid sequence found in virulent *C. perfringens* type A. A nucleic acid sequence encoding an antigenic polypeptide may be used either singly or in combination with other nucleic acid sequences, encoding antigenic polypeptides or encoding any other desired polypeptide, in the preparation of a vaccine.

An isolated nucleic acid molecule encoding a *C. perfringens* antigenic polypeptide is a nucleic acid molecule that is identified and separated from at least one contaminant nucleic acid molecule with which it is ordinarily associated in the natural source of the nucleic acid. Such an isolated nucleic acid molecule is other than in the form or setting in which it is found in nature. Isolated nucleic acid molecules therefore are distinguished from the nucleic acid molecule as it exists in natural cells. An isolated nucleic acid molecule encoding a *C. perfringens* antigenic polypeptide includes nucleic acid molecule encoding a *C. perfringens* antigenic polypeptide contained in cells that ordinarily express the *C. perfringens* antigenic polypeptide where, for example, the nucleic acid molecule is in a chromosomal or extrachromosomal location different from that of natural cells. The isolated nucleic acid molecule may be referred to as a recombinant nucleic acid molecule where the isolated nucleic acid molecule has been manipulated using recombinant techniques, for example, as described in 3. Sambrook, E. F. Fritsch, and T. Maniatis, 1989, Molecular Cloning: A Laboratory Manual, Second Edition, Books 1-3, Cold Spring Harbor Laboratory Press.

Variants include, without limitation, analogs, derivatives, fragments, truncations, mutants, deletions, substitutions, insertions, fusions and the like. Any variant may be used in the vaccine described herein provided that the variant maintains an immunoprotective activity.

An antigenic polypeptide or a nucleic acid encoding an antigenic polypeptide may be mutated or changed or derivatised in any manner desired (for example, any number or combination of deletions, insertions, or substitutions) to produce a corresponding variant. For example, a variant may be a fragment of an antigenic polypeptide, which fragment may optionally be fused to another polypeptide, such as a carrier protein and/or a T-cell epitope. As another example, a variant may be a fragment of a nucleic acid encoding an antigenic polypeptide, which fragment may optionally be fused with a nucleic acid encoding another polypeptide, such as a carrier protein and/or a T-cell epitope. Examples of suitable fragments are indicated in FIG. 2, 18, 19 or 20.

Use of variants in producing vaccines and in vaccinating a subject is contemplated, and such a variant nucleic acid or variant polypeptide may be mutated or changed or derivatised in any manner in comparison to a naturally occurring nucleic acid or polypeptide sequence, respectively, found in virulent

*C. perfringens* (type A), provided that the capability of conferring an immunoprotective effect against *C. perfringens* is maintained. Similarly, nucleic acids or polypeptides having varying degrees of sequence identity to a corresponding naturally occurring nucleic acid or polypeptide sequence found in virulent *C. perfringens* (type A) may be tolerated without eliminating an immunoprotective activity against *C. perfringens*. For example, a vaccine may comprise an antigenic polypeptide having a sequence that is identical to a naturally-occurring form of the antigenic polypeptide or a variant thereof that has a sequence that is at least 80% identical to a naturally-occurring form of the antigenic polypeptide. As another example, a vaccine may comprise a nucleic acid molecule having a coding sequence that is identical to a naturally-occurring form of the coding sequence or a variant thereof that has a sequence that is at least 70% identical to a naturally-occurring form of the coding sequence. Determination of sequence identity of proteins and nucleic acids by computer based methods, as well as nucleic acid hybridization techniques using high stringency conditions for determining or identifying nucleic acid sequences that share high (e.g., at least 70%) sequence identity are well known to the skilled person.

Stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of sequence identity between the probe and hybridizable sequence, the higher the relative temperature which can be used. High stringency conditions may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. Hybridization and wash times should be sufficient for achieving equilibrium.

Percent (%) sequence identity of amino acid or nucleic acid sequences with respect to antigenic polypeptides as, for example in FIGS. 1 to 6, and nucleic acid sequences encoding antigen polypeptides is the percentage of residues in a candidate sequence that are identical with the antigenic polypeptide amino acid sequence or the antigenic polypeptide-encoding nucleic acid sequence, as the case may be, after aligning the sequences and introducing gaps, if necessary, to achieve the maximum percent sequence identity. Alignment for purposes of determining percent amino acid sequence identity or percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over a desired length of sequence, for example, at least 20, 30, 40, 50, 60, 70, 80, 90, 100, 110, 120, 130, 140, 150, 160, 170, 180, 190, or 200 residues or even the full-length of the sequences being compared.

When considering an antigenic polypeptide or variant thereof, the variant antigenic polypeptide will typically have an amino acid sequence that is at least 80, 82, 84, 86, 88, 90, 92, 94, 96, or 98 percent identical to the corresponding antigenic polypeptide.

When considering a nucleic acid sequence encoding an antigenic polypeptide or variant thereof, the variant nucleic acid sequence will typically be at least 70, 72, 74, 76, 78, 80, 82, 84, 86, 88, 90, 92, 94, 96, or 98 percent identical to the corresponding nucleic acid encoding the antigenic polypeptide.

Techniques and strategies for producing variants are well known in the art. In one example, with regard to polypeptides, an antigenic polypeptide may be modified in vivo or in vitro by, glycosylation, amidation, phosphorylation, carboxylation, truncation, fragmentation, substitution, and the like without eliminating an immunoprotective activity against *C. perfringens*. In another example, with regard to nucleic acids, substitution mutations can be made in a nucleic acid encoding an antigenic polypeptide such that a particular codon is changed to a codon which codes for a different amino acid. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e. by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. Groupings of amino acids are known to the skilled person. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charges (basic) amino acids include arginine, lysine and histidine. The negatively charged (acidic) amino acids include aspartic acid and glutamic acid. Any number of such substitutions or any other type of alteration (e.g., deletion or insertion) or modification may be tolerated provided that the immunoprotective effect of the antigenic polypeptide is not eliminated.

Antibodies may be generated against antigenic polypeptides. The antibodies may be monoclonal or polyclonal.

Recombinant cells, comprising an antigenic polypeptide or a nucleic acid sequence that encodes an antigenic polypeptide may be used as vaccines for controlling *C. perfringens*. Recombinant cell types may include any cell type that is compatible with the physiology of an intended vaccination subject. Cells of eukaryotic or prokaryotic origin may be used. Prokaryotic cells that can survive within the gastrointestinal system of an intended vaccination subject may be particularly useful for preparation of oral or enteral vaccines. For example, cells that form part of the intestinal flora of an intended vaccination subject (such as *Eschercichia coli* or *Lactobacillus* species) may be used. In another example, avirulent *Salmonella* or *Listeria* or other attenuated invasive bacterial cells may be used.

Examples of recombinant cell vaccines, using for example non-pathogenic recombinant cells or attenuated pathogenic microorganisms such as *Salmonella typhimurium* or *Mycobacterium bovis*, and methods of their delivery, for example oral or mucosal, are known to the skilled person. See for example PCT publications WO2001/021200 or WO2003/020040.

A cell may be altered or modified to comprise a nucleic acid sequence that does not naturally occur in the cell, and as such the cell will be considered recombinant. In other examples, a cell may be altered or modified to comprise an additional copy of a nucleic acid sequence that naturally occurs in the cell, and such cells will also be considered recombinant. As is understood by one of skill in the art, a nucleic acid encoding an antigenic polypeptide may be introduced into a cell using any known technique, for example, microinjection, electroporation, viral transfection, lipofectamine transfection, calcium phosphate precipitation and the like. In certain non-limiting examples, a bacterial cell may be modified by introduction of a nucleic acid molecule encoding an antigenic polypeptide, and then the modified cells may be administered to a subject. In certain other examples, a nucleic acid molecule encoding an antigenic polypeptide may be incorporated into an appropriate construct or vehicle, for example a viral construct, and administered to a subject such that the nucleic acid molecule encoding the antigenic polypeptide is introduced and expressed in at least a portion of the cells of the subject.

A nucleic acid encoding an antigenic polypeptide may be operably linked to control sequences, typically in the context of a suitable vector. A useful control sequence may be any nucleic acid element that is necessary or advantageous for expression of the coding sequence of the nucleic acid sequence. Each control sequence may be native or foreign to the nucleic acid sequence encoding the antigenic polypeptide. Such control sequences include, but are not limited to, a leader, a polyadenylation sequence, a propeptide sequence, a promoter, a signal sequence, or a transcription terminator. Alternatives for incorporating control sequences are readily available to the skilled person. For example, a nucleic acid encoding an antigenic polypeptide may be under the control of an endogenous upstream promoter, or it may be put under control of a heterologous upstream promoter. Examples of suitable promoters for directing the transcription of the modified nucleotide sequence, such as PS4 nucleic acids, in a bacterial host include the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase gene (amyQ), the promoters of the *Bacillus subtilis* xylA and xylB genes, the promoter of the *Bacillus subtilis* aprE gene and a promoter derived from a *Lactococcus* sp.—derived promoter including the P170 promoter. When the gene encoding the PS4 variant polypeptide is expressed in a bacterial species such as *E. coli*, a suitable promoter can be selected, for example, from a bacteriophage promoter including a T7 promoter and a phage lambda promoter.

For transcription in a fungal species, examples of useful promoters are those derived from the genes encoding the, *Aspergillus oryzae* TAKA amylase, *Rhizomucor miehei* aspartic proteinase, *Aspergillus niger* neutral .alpha.-amylase, *A. niger* acid stable .alpha.-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase.

Examples of suitable promoters for the expression in a yeast species include but are not limited to the Gal 1 and Gal 10 promoters of *Saccharomyces cerevisiae* and the *Pichia pastoris* AOX1 or AOX2 promoters.

Still further suitable promoters are available to the skilled person, for example, cytomegalovirus, Rous Sarcoma Virus, synthetic pox viral promoter, pox synthetic late promoter 1, pox synthetic late promoter 2 early promoter 2, pox 01L promoter, pox 14L promoter, pox 13L promoter; pox 12L promoter, pox IIL promoter, pox DIOR promoter, PRV gX, HSV-1 alpha 4, chicken beta-actin promoter, HCMV immediate early, MDV gA, MDV gB, MDV gD, ILT gB, BHV-1.1 VP8 and ILT gD and internal ribosomal entry site promoter.

A suitable vector may be any vector (for example, a plasmid or virus) which can incorporate a nucleic acid sequence encoding an antigenic polypeptide and any desired control sequences and can bring about the expression of the nucleic acid sequence. The choice of the vector will typically depend on the compatibility of the vector with a host cell into which the vector is to be introduced. In certain examples, the vector may exist as an extrachromosomal entity, with replication being independent of chromosomal replication, for example, a plasmid, an extrachromosomal element, a minichromosome, or an artificial chromosome. In other examples, the vector may be one which, when introduced into the host cell, is integrated into the genome and replicated together with the chromosome(s) into which it has been integrated. Still other examples of vectors and techniques for manipulating vectors will be known and apparent to the skilled person.

Recombinant cells may comprise an antigenic polypeptide or a nucleic acid sequence encoding an antigenic polypeptide, either singly or in combination, with other desired polypeptide or nucleic acid molecules, respectively, to optimize vaccination efficacy. Furthermore, a nucleic acid sequence may be mutated or altered prior to introduction into the cells as desired, for example for codon optimization for expression in a particular cell type. In addition, a nucleic acid sequence may be altered to encoded a fusion of an antigenic polypeptide with one or more other polypeptide as desired in an application, for example fusion with a targeting polypeptide or a carrier polypeptide.

As is understood by the skilled person, administration of a vaccine can be done in a variety of manners. For example, administration may be done intramuscularly, subcutaneously, intravenously, intranasally, intradermaly, intrabursally, in ovo, ocularly, orally, intra-tracheally or intra-bronchially, as well as combinations of such modalities. The dose of the vaccine may vary with the size of the intended vaccination subject. Methods of administration are known to the skilled person, for example, U.S. Pat. Nos. 5,693,622; 5,589,466; 5,580,859; and 5,566,064. The amounts of polypeptide, nucleic acid sequence, or recombinant cell needed for preparation of a vaccine is well understood by one of skill in the art.

Oral vaccines, that is vaccines formulated for oral delivery, may be convenient for delivery of vaccines to non-human animals, for example as a feed additive. Such oral vaccine compositions can be alkaline, since alkali can neutralise acid in the stomach, and allow at least a portion of the vaccine composition to pass through the stomach into the intestine intact. Vaccines comprising recombinant bacterial cells may be particularly well suited for oral delivery. Such vaccines will be formulated such that at least a portion of the recombinant bacteria administered will survive the stomach, and pass into the intestine. Increased immune responses can be achievable when recombinant bacteria are alive, because they can continue to express the heterologous antigenic polypeptide in vivo.

An antigenic polypeptide, a nucleic acid encoding an antigenic polypeptide, or a recombinant cell, may be used in combination with a pharmaceutically acceptable carrier for preparation of a vaccine. Pharmaceutically acceptable carriers for vaccines are well known to those skilled in the art and include but are not limited to proteins, sugars, and the like. One example of such a suitable carrier is a physiologically balanced culture medium containing one or more stabilizing agents such as hydrolyzed proteins, lactose, and the like. Another example of an acceptable carrier is 0.01-0.1M, and preferably 0.05M, phosphate buffer or 0.8% saline. Acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media. Preservatives and other additives for vaccines are also well know to the skilled person, for example antimicrobials, antioxidants, chelating agents, inert gases, organic acids and the like.

Acceptable adjuvants, for example as described in U.S. Pat. No. 6,908,620, may be used to enhance the immune response to an antigenic polypeptide. Acceptable adjuvants include, without limitation: polymers of acrylic or methacrylic acid, maleic anhydride and alkenyl derivative polymers; immunostimulating sequences (ISS), such as oligodeoxyribonucleotide sequences having one or more non-methylated CpG units (WO98/16247); oil in water emulsion; cation lipids containing a quaternary ammonium salt; cytokines; aluminum hydroxide or aluminum phosphate; or any combinations or mixtures thereof.

An oil in water emulsion adjuvant can be based on, for example, light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Examples of adjuvant polymers crosslinked acrylic or methacrylic acid, especially crosslinked by polyalkenyl ethers of sugars or polyalcohols. U.S. Pat. No. 2,909,462, provides examples of such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms.

An example of a cationic lipid adjuvant is DMRIE (N-(2-hydroxyethyl)-N,N-dimethyl-2,3-bis(tetradecyloxy)-1-propane ammonium; WO96/34109), either alone or associated with a neutral lipid, for example, DOPE (dioleoyl-phosphatidyl-ethanol amine), to form DMRIE-DOPE.

Examples of cytokine adjuvants are granulocyte colony stimulating factor (G-CSF), granulocyte/macrophage colony stimulating factor (GM-CSF), interferon alpha (IFN alpha), interferon beta (IFN beta), interferon gamma, (IFN gamma), interleukin-1alpha (IL-1alpha), interleukin-1beta (IL-1beta), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor alpha (TNF alpha), tumor necrosis factor beta (TNF beta), and transforming growth factor beta (TGF beta). A cytokine adjuvant can be in form of a cytokine polypeptide or a nucleic acid sequence encoding a cytokine polypeptide.

Still further adjuvants known to the skilled person include, without limitation, complete Freund's adjuvant, incomplete Freund's adjuvant, saponin, mineral gels such as aluminum hydroxide, surface active substances such as lysolecithin, pluronic polyols, polyanions, peptides, keyhole limpet hemocyanins, dinitrophenol, and the like.

Adjuvants may be co-administered or sequentially administered with a vaccine.

The vaccine described herein can be useful for controlling *C. perfringens* in an animal, for example a bird, a cow or a pig. The vaccine may be useful in any bird, wild, domesticated or commercially farmed, for example, chicken, turkey, goose, duck, pheasant, quail, pigeon and ostrich. Administration of the vaccine to a subject can confer an immunoprotective effect to the subject against *C. perfringens*. Administration of the vaccine to a subject may reduce or prevent symptoms of a *C. perfringens* infection. The vaccine may be for prophylactic, therapeutic, or both prophylactic and therapeutic treatment. The vaccine can control *C. perfringens* by reducing or preventing infection or proliferation of *C. perfringens* in an animal. The vaccine may be used in combination with other treatments, for example, therapeutic antibodies or antibiotics.

When introducing elements disclosed herein, the articles "a", "an", "the", and "said" are intended to mean that there are one or more of the elements unless the context dictates otherwise. For example, the term "a compound" and "at least one compound" may include a plurality of compounds, including mixtures thereof. The terms "comprising", "having", "including" are intended to be open-ended and mean that there may be additional elements other than the listed elements.

The above disclosure generally describes preferred embodiments. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

*Clostridium perfringens* Antigens Recognized by Broiler Chickens Immune to Necrotis Enteritis Four strains of *C. perfringens* (CP1, CP4, CP5, and CP6) used in this study are clinical isolates from field cases of NE. Strains CP1 and CP4 are virulent, and CP5 and CP6 avirulent, isolates, as assessed by their abilities to cause NE (32). *Clostridium perfringens* cells were grown anaerobically in an empirically formulated medium (tryptic soy broth [Difco] 50%, nutrient broth [Difco] 25% and peptone water [Difco] 25%) for 24 h at 37° C., and the cells and culture supernatant were collected thereafter. The cells were lysed by eight freeze-thaw cycles with liquid nitrogen to obtain whole-cell proteins. The culture supernatant was dialyzed and concentrated by use of 10-kDa cutoff Amicon filters (Millipore Inc., Billerica, Mass.) to obtain secreted proteins. The protein concentration was determined using a PlusOne 2-D Quant kit (Amersham Biosciences, San Francisco, Calif.). The protein contents of concentrated secreted and whole-cell protein samples were 3 to 4 mg/ml. For sodium dodecyl sulfate-polyacrylamide gel electrophoresis (SDS-PAGE) analysis under reducing conditions, 100 µg of protein sample was applied.

The secreted and whole-cell proteins were separated by one-dimensional SDS-PAGE in a 12.5% acrylamide gel under reducing and nonreducing conditions (16). The gels were visualized by Coomassie R-250 staining. The proteins from the gel were transferred to a nitrocellulose membrane of 0.45-µm pore size (Bio-Rad Laboratories) by use of a Hoefer tank buffer system (Amersham Biosciences) followed by reaction with primary antibodies (serum or intestinal washing) at 1:1,000 and 1:500 dilutions, respectively. Serum (source of immunoglobulin Y [IgY]) used in this study was pooled from broiler chickens immune to virulent *C. perfringens* challenge in infection-immunization experiments (32). The pooled small intestinal washings made from these birds by use of phosphate-buffered saline were dialyzed, concentrated, and used as the source of primary antibody (IgA and IgY) in Western blotting and neutralization experiments. Anti-chicken IgY (heavy plus light chains) and anti-chicken IgA were used as secondary antibodies at 1:2,000 and 1:1,000 dilutions, respectively. Specific immunoreactive protein bands were visualized using an alkaline phosphatise-conjugated substrate kit (Bio-Rad Laboratories).

Several protein bands from strain CP4 showed reactivity to immune serum, but similar reactivity was not observed for secreted proteins from CP5. This lack of reactivity was also observed when secreted proteins from avirulent strain CP6 were reacted with immune serum. Secreted proteins from another virulent strain, CP1, showed reactivity similar to that seen for CP4. The secreted protein bands of CP4 that showed reactivity to immune serum were consistently reactive in multiple gels run at different times. Although there was little reactivity of CP4- and CP5-secreted proteins to intestinal IgA, the reactivity of these secreted proteins to intestinal IgY was similar to that of Western blots done with immune serum. Therefore, it seems that both intestinal and serum IgY antibodies are important in immunity to this infection. No differences in the whole-cell protein reactivities to serum or intestinal washings between virulent and avirulent strains were observed, suggesting that the trait of immune protection against NE lies in the secreted components of virulent *C. perfringens*.

Six immunoreactive secreted proteins unique to virulent strains, of which five were highly antigenic, were identified in the parallel-run Coomassie-stained gels by use of the coordinates of molecular-weight-marker bands and the distance of migration. The gels from the centers of these bands were excised, in-gel digested, and identified by mass spectrometric techniques, namely, matrix-assisted laser desorption ionization mass spectrometry (MALDI-MS) and electrospray ionization mass spectrometry (ESI-MS/MS). The peptide masses and sequence data from MS analysis were searched against the National Center for Biotechnology Information (NCBI) protein database by MS-Fit from the database named "ProteinProspector" which is operated by University of California, San Francisco, Calif., USA and Matrix-Science Mascot search operated by Ohio Supercomputer Center, Ohio, USA to identify the protein that had the highest homology percentage match. Of the six antigenic secreted proteins unique to the two virulent, immunoprotective strains identified by MS (FIGS. 1 to 6), three (perfringolysin 0, fructose 1,6 biphosphate aldolase [FBA], and elongation factor G [EF-G]) are regulated by the VirR-VirS virulence regulon of *C. perfringens* (3). In addition to virulence genes, this regulon controls genes involved in energy metabolism, such as those encoding FBA and NAD-dependent .beta.-hydroxybutyryl coenzyme A dehydrogenase, as well as others that may be indirectly involved in bacterial virulence (3,13, 28). It therefore seems possible that the marked difference in the immunoreactivities of the secreted proteins between the two virulent and the two avirulent strains is the result of a mutation in this regulatory region in the avirulent strains and that the quantity of these proteins produced is too low to be detected in SDS-PAGE and Western blotting experiments. The avirulent strains do produce alpha-toxin; however, the amount produced was not quantified.

Example 2

Antigenic Epitopes of Alpha-Toxin

Purified *C. perfringens* alpha-toxin (Sigma Laboratories) was separated by SDS PAGE and Western blotting performed using chicken immune serum and intestinal antibodies, as well as alpha-toxin antiserum (J. G. Songer, University of Arizona) raised in goats. As expected, alpha-toxin antiserum detected purified alpha toxin (43 kDa). Interestingly, in the Western immunoblot no antibodies to alpha-toxin were detected either in serum or intestinal washings of immune birds. However, further study showed antibodies to alpha toxin were detected in serum at titres of 5000 when native (and not denatured) alpha toxin was used in a lecithinase inhibition assay. In addition, there was immunoreactivity when a Western immunoblot was run against alpha toxin electrophoresed in a non-denaturing gel. This suggests that neutralizing antibodies to alpha toxin are present in immune birds but these may be to conformational rather than linear protein epitopes.

Achieving conformational but non-toxic alpha-toxin epitopes in a vaccine may prove challenging. A structure-function analysis of alpha-toxin suggests that the toxicity is associated with the N-terminus whereas the immunogenicity is associated with the C-terminal domain (1, 7, 33). However, the hemolytic activity was found to result from an interaction of both the domains (1). Although many studies have emphasized the importance of non-toxic C-terminal domain in protection against experimental gas gangrene (5, 30, 34), some have shown the neutralizing epitopes to be on the N-terminus (18). It seems likely that the positioning of protective, neutralizing, conformational epitopes of alpha-toxin is subtle and that these epitopes are shared upon folding between both domains, which play a key role in toxicity and also in protective immunogenicity, thus making them hard to access by antibodies.

Example 3

Cloning, Expression and Purification of Secreted Antigenic Polypeptides from Virulent *C. perfringens*

The chromosomal DNA of the virulent, protective, *C. perfringens* strain CP4 was used as the source of DNA for cloning of secreted antigens: alpha-toxin, glyceraldehyde 3-phosphate dehydrogenase (GPD), pyruvate: ferredoxin oxidoreductase (PFOR), fructose 1,6-biphosphate aldolase (FBA) and a Hypothetical Protein (HP). PCR was performed using the proofreading DNA polymerase (Qiagen, Mississauga, ON) and primers designed to specifically amplify DNA fragments in the genes. The primers used to amplify the genes are given in Table 1.

TABLE 1

List of primers used to amplify genes encoding proteins used in immunization experiments

| Gene | Sequences 5'-3' | Amplicon size (bp) |
|---|---|---|
| Alpha-toxin | Forward-<br>ccgctcgagttgggatggaaaaattgat<br>Reverse-<br>ccggaattctttatattataagttgaattt | 1100 |
| Hypothetical protein | Forward-<br>ccgctcgaggaataagagaaaaatagcag<br>Reverse-<br>ccgggtaccacgttaaataaatagaacat | 5400 |
| Glyceraldehyde 3-phosphate dehydrogenase | Forward-<br>ccgctcgagggtaaaagtagctattaacgg<br>Reverse-<br>ccgggtaccttagaaactaagcattttaaa | 1000 |
| Fructose 1,6-biphosphate aldolase | Forward-<br>ccgcggatccatggcattagttaacgcaaa<br>Reverse-<br>ccgcctcgagagctctgtttactgaaccga | 900 |
| Truncated pyruvate: ferredoxin oxidoreductase | Forward-<br>ccgcctcgagcacttcattagaaccagttg<br>Reverse-<br>ccgcggatcctagctaagtagtcttggtct | 1600 |

After purification (PCR Purification Kit, Qiagen, Mississauga, ON), the PCR products were cloned into plasmid expression vectors so as to generate proteins fused with histidine residues (6-His) either at the N-terminus or at the C-terminus of the protein sequence. Two plasmid vectors, pBAD (for cloning alpha-toxin, GPD and HP) and pET-28 (for cloning FBA and tPFOR), were used in this study.

The resulting plasmids were introduced into *E. coli* LMG 194 or BL21 Star (DE3) (Invitrogen, Carlsbad, Calif.), following the manufacturer's instructions. For protein expression, overnight cultures were used to inoculate a fresh Luria broth (LB) medium supplemented with ampicillin or kanamycin (100 µg/ml). Bacteria were grown at 37° C. under aerobic conditions and L-arabinose (St. Louis, Mo.) (0.2% final) or isopropyl-beta-D-thiogalactopyranoside (IPTG) (Qbiogene, Vista, Calif.) was added (1 mM) to the bacterial culture in exponential growth phase ($OD_{500}$-0.5). After a further incubation for 4 h, cells were harvested by centrifugation.

Purification of recombinant proteins was performed by affinity chromatography on nickel-nitrilotriacetic acid (Ni-NTA) agarose following the manufacturer's instructions (Qiagen). Briefly, when the proteins were expressed as soluble proteins, bacterial pellets were resuspended in a buffer (50 mM $NaH_2PO_4$, 300 mM NaCl) containing lyzozyme (1 mg/ml) and incubated for 60 min in ice. The bacterial cells were lysed using a French pressure cell (3-4 cycles of 1000 psi). The supernatant was collected by centrifugation and added to Ni-NTA agarose. The washing and elution steps were performed using buffers containing increasing concentration of imidazole. Finally, imidazole was removed from the eluted material by dialysis against phosphate buffered saline, pH 7.2, (PBS) and the recombinant proteins were concentrated using Amicon filter –10 kD (Millipore, Billerica, Mass.) and the protein concentration was determined using PlusOne' 2-D Quant kit (Amersham Biosciences, San Francisco, Calif.).

Purified recombinant proteins were separated by one-dimensional sodium dodecyl sulfate polyacrylamide gel electrophoresis (SDS-PAGE) in a 12.5% acrylamide gel under denaturing conditions as described by Laemmli (16). Proteins were transferred to nitrocellulose membrane of 0.45 pm pore size using a mini-gel transfer assembly (Bio-Rad Laboratories, Hercules, Calif.). After completion of transfer, non-specific binding sites on the membranes were blocked with blocking buffer containing 1% casein (Bio-Rad Laboratories) and incubated with primary antibodies (immune serum collected from infection-immunized birds in a previous study (32) at 1:1000 dilution. Anti-chicken IgY (H+L) (Cedarlane Laboratories, Hornby, ON) was used as secondary antibody at 1:2000 dilution. The blots were developed and specific immunoreactive protein bands were visualized using an alkaline phosphatase-conjugated substrate kit (Bio-Rad Laboratories) (see FIG. 7).

All five genes selected for the immunization study were successfully cloned, expressed and purified to homogeneity.

Cloning of the full length pfor gene was not successful, possibly because of homologous recombination. However, a portion of the gene that encoded a truncated protein (tPFOR) of 67 kDa size (see underlined portion of FIG. 2) that contained the Iron-Sulphur (Fe—S) active sites of this enzyme was successfully cloned and purified in large quantities.

Although alpha-toxin was successfully cloned, expressed and purified, the quantity obtained was insufficient for immunization, possibly because of toxicity for the *E. coli* host. Hence, commercially available purified alpha-toxin (Sigma Laboratories, St. Louis, Mo.) was used for immunization experiments.

Hypothetical Protein (190 kDa) was found to be cleaved into two bands of 90-100 kDa size upon expression. Attempts to express the entire protein by changing *E. coli* expression hosts were unsuccessful. Since these two bands reacted strongly to anti-histidine antibodies as well as to immune serum collected from infection-immunized birds (FIG. 7) from a previous study (32) these two bands were further purified in large quantities and used in immunization experiments.

Example 4

Immunization Experiments in Chickens

Experiments with chickens and conditions for their use were approved by the University of Guelph Animal Care Committee in accordance to the Canadian Council on Animal Care's Guidelines. Commercial 1-day-old male White Plymouth Rock broiler chickens (Bonnie's Chick Hatchery, Elmira, Ont., Canada) were fed an antibiotic-free chicken starter containing 20% protein for 13 days followed by a formulated wheat-based grower feed, containing 28% protein (Arkell Research Station, University of Guelph). Birds were immunized intramuscularly in the pectoral muscle in a volume of 0.2 ml per bird with purified recombinant proteins at different concentrations and frequencies.

In all experiments, the number of birds in each group was between 10 and 20 and all birds were identified individually. Blood was collected from the wing vein from all the groups at three times: pre-immunization, mid-experiment and pre-challenge. Intestinal washings were collected using PBS at autopsy.

For the experimental infection of birds, virulent *C. perfringens* CP4 was grown in cooked meat medium (Difco) (CMM) for 24 h at 37° C. Fluid thioglycolate medium (FTG, Difco) was then inoculated with a 3% (v/v) inoculum from the *C. perfringens* infected CMM and incubated at 37° C. for 24 h. The growth at 24 h was $log_io$ 8.24±0.09 *C. perfringens* CFU/ml. The inoculated FTG was then mixed with feed at a ratio of 2:1 (v/w). Inoculated feed was prepared freshly twice per day and fed to chickens for 3-5 days as described.

Autopsy

Chickens were euthanized with carbon dioxide gas and their small intestines (duodenum to ileum) examined for grossly visible lesions. Any chickens that had reached a pre-determined severity of clinical illness prior to autopsy were euthanized and later autopsied. Intestinal lesions in the small intestine (duodenum to ileum) were scored as follows: 0=no gross lesions; 1=thin or friable wall; 2=focal necrosis or ulceration; 3=large patches of necrosis; 4=severe extensive necrosis; 5=chickens that died during experiment, having 4+ lesions (25). Blind scoring was employed to avoid scorer bias. A pathological change of mild generalized and superficial intestinal necrosis, not previously included in this scoring system (25), was assigned a score of 1+.

A visual summary of mean lesion scores of birds from all immunized groups that received different doses of antigens and challenge across different experiments, together with the concurrent unimmunized controls, is shown in FIG. 8.

Measurement of the Antibody Titers in Chicken Sera and Intestinal Washings

The specific antibody titers were determined by the end point dilution method using an enzyme-linked immunosorbent assay (ELISA). Microtiter plates (Immulon-2, Chantilly, Va.) were coated with recombinant proteins (5 μg/ml in 0.1 M carbonate buffer pH 9.6) for 60 min at 37° C. followed by an overnight incubation at 4° C. After blocking coated plates for 60 min at 37° C. with PBS containing 3% of bovine serum albumin (BSA Sigma), immune sera were serially diluted in PBS containing BSA 1% and incubated for 2 h with recombinant protein-coated plates at room temperature. After washing with PBS containing Tween 20 0.1% (PBST), alkaline phosphatase (AP)-coupled anti-chicken IgY (H+L) (1:5,000 in PBS-Tween 20 0.1%-BSA 1%) was added to the microplates and incubated for 60 min at room temperature. After extensive washing with PBST, color reaction was developed using alkaline phosphate substrate kit (Bio-Rad Laboratories) following the manufacturer's instructions. The reaction was stopped by adding 0.4 M NaOH. The absorbance was measured at 405 nm in an ELISA spectrophotometer. The specific antibody titer of immune serum was expressed as the reciprocal of the serum dilution ($log_2$ OD) that gave an A405 value above the cut-off, defined as twice the absorbance value of the un-immunized and mock control wells.

Intestinal antibody response was also measured by ELISA following the procedure described above for serum. Intestinal washings from at least 10 chickens per group were pooled and the total protein content was measured using PlusOne™ 2-D Quant kit (Amersham Biosciences) and used as source of primary antibody after keeping the protein content of the initial dilution (1:10) constant across all the groups. Alkaline phosphatase conjugated anti-chicken IgY and IgA were used as secondary antibodies at dilutions of 1:4000 and 1:2000 respectively. The end-point titres were determined as described above for serum ELISA.

Although purification of histidine tagged recombinant proteins through Ni-NTA agarose column should yield eluted protein free of LPS, using mock-immunized (as well as non-immunized control bird) serum to determine the cut-off value further strengthened the interpretation of results. All the proteins used to immunize birds in the immunization experiments described produced significant antigen-specific serum antibody titres (FIG. 9) compared to their pre-immunization titres. Alpha-toxoid immunized but non-protected birds as shown in Experiment-1 below had higher titres than toxoid-active toxin immunized birds that were highly protected in Experiment-3 below.

Intestinal antibody responses to all the immunized proteins showed higher IgY than IgA titers (FIG. 10). However, unlike serum, such a difference was not observed between alpha-toxoid (Experiment-1) and toxoid-active toxin boosted (Experiment-3) birds.

Statistical Analysis

Statistical analysis was performed to determine whether there was a significant difference between the number of birds with lesions from immunized groups and birds from the unimmunized, vehicle-only controls. A two-tailed Fisher's exact test determined whether the two groups differed in the proportion with which they fell into the two classifications of either lesions or no lesions, under the null hypothesis that the proportions were the same. Data was analyzed in a 2×2 contingency table with the unimmunized control group in one column and immunized groups in the other column. Lesion scores were ranked from 0 to 5+, however, a "protective" response was given to birds with <1+ lesions. The null hypothesis was rejected at a=0.05. For serum ELISA, a one-way ANOVA (Mini-tab 14 software) was used to determine significant differences the antibody titres between pre-immunized and immunized time points across all the groups. Statistical analysis could not be made on intestinal ELISA, since the washings collected were pooled per group.

A summary of the immunization experiments is shown in Table 2.

TABLE 2

Summary of experimental design

| Experiment | Immunization Groups | Dosage of vaccine/ Bird | Frequency of administration | Oral challenge |
|---|---|---|---|---|
| 1 | VC, Sup[a], Alpha-toxoid, GPD, HP, FBA and tPFOR | 20 μg | Three times; day 7, 14 and 21 | 3 days (mild) |
| 2 | VC, MC[b], GPD, HP, FBA and tPFOR | 40 μg | Two times; day 7 and 14 | 5 days (moderate) |

TABLE 2-continued Summary of experimental design

| Experiment | Immunization Groups | Dosage of vaccine/ Bird | Frequency of administration | Oral challenge |
|---|---|---|---|---|
| 3 | VC, Alpha-toxoid/ toxin[c], GPD, HP, tPFOR, combination of GPD and HP | 20 µg | Three times; day 7, 14 and 21 | 5 days (severe) |
| 4A | VC and FBA | 20 µg | Three times; day 7, 14 and 21 | 3 days (mild-moderate) |
| 4B | VC, Alpha-toxin[d] and FBA | 20 µg | Three times; day 7, 14 and 21 | 5 days (severe) |

VC—Vehicle-only controls, GPD—glyceraldehyde 3-phosphate dehydrogenase, tPFOR—truncated pyruvate: ferredoxin oxidoreductase, FBA—fructose 1,6-biphosphate aldolase, HP—Hypothetical protein, Sup—crude culture supernatent of virulent C. perfringens and MC—mock-immunized controls
[a]Birds received 60 µg/inj of culture supernatant that was processed and concentrated following a protocol described earlier (15).
[b]Birds were mock immunized with an unrelated protein that was cloned, expressed and purified from E. coli in the same manner as C. perfringens related proteins.
[c]Birds received alpha-toxoid in the first two injections followed by active alpha-toxin in the third.
[d]Birds in this group received three injections of alpha-toxin where in the first and the third injections were with 20 µg and the second was reduced to 10 µg.

In Experiment-1, birds were immunized with alpha-toxoid, HP, GPD, FBA and tPFOR. Each bird received three injections of 20 µg of recombinant protein and 50 µg of Quil-A adjuvant (Superfos Biosector, Vedbaek, Denmark) on days 7, 14 and 21 of age. A week later, following a 20 h fast, birds were orally challenged 2-3 times a day with virulent C. perfringens. This challenge was considered 'mild' since the duration of challenge was 3 days and lesions produced in non-immunized birds were relatively mild. Post mortem examination was performed on all birds on day 31, or on birds that died earlier, and the intestinal lesions were scored. A group of birds also received crude culture supernatant of CP4 obtained, processed and concentrated following a protocol described earlier (15) at a dose of 60 µg/bird/injection. The unimmunized controls received only Quil-A adjuvant followed by a challenge similar to immunized groups. Purified alpha-toxin was toxoided following the protocol described (11) and used for immunization.

HP, GPD, tPFOR and FBA showed significant protection against a mild infection challenge (Table 3). Immunization with crude culture supernatant that contained all secreted proteins including those purified also showed significant protection. Alpha-toxoid did not protect birds against challenge. Hypothetical Protein showed the greatest protection.

TABLE 3

Intestinal lesion scores of birds immunized with three injections intramuscularly, then infected with a mild challenge by C. perfringens

| Protein | No. of chickens | Lesion scores | | | | | | Mean |
|---|---|---|---|---|---|---|---|---|
| | | 0 | 1+ | 2+ | 3+ | 4+ | 5+ | |
| Vehicle-only controls | 10 | 1 | 3 | 4 | 1 | 1 | 0 | 1.55 |
| Culture supernatant* | 10 | 8 | 1 | 1 | 0 | 0 | 0 | 0.4 |
| Alpha-toxoid | 12 | 3 | 4 | 3 | 1 | 1 | 0 | 1.41 |
| HP* | 12 | 10 | 2 | 0 | 0 | 0 | 0 | 0.16 |
| GPD* | 10 | 7 | 2 | 1 | 0 | 0 | 0 | 0.4 |
| tPFOR* | 10 | 4 | 5 | 1 | 0 | 0 | 0 | 0.7 |
| FBA* | 10 | 4 | 6 | 0 | 0 | 0 | 0 | 0.6 |

*Immunized groups that had significantly fewer chickens with lesions compared to unimmunized vehicle-only controls; Fisher's exact test, $p \leq 0.05$.

In Experiment-2, birds were immunized with HP, GPD and tPFOR. Each bird received two injections of 40 µg of recombinant protein and 50 µg of Quil-A adjuvant on days 14 and 21 of age. A week later, following 20 h fasting birds were orally challenged with virulent C. perfringens twice a day for five days, from days 28-32 of age. Since feeding was restricted to twice daily and birds ran out of feed on some occasions, and in light of the moderate lesion scores in unimmunized birds, this challenge was considered 'moderate'. Post mortem examination was performed on day 33 and intestinal lesions were scored. The unimmunized controls received only Quil-A adjuvant followed by a challenge similar to immunized groups. A group of birds were mock immunized with an unrelated protein that was cloned, expressed and purified from E. coli in the same manner as C. perfringens related proteins.

HP alone showed significant protection against a moderate challenge, whereas GPD, tPFOR and FBA did not (Table 4). Immunization (mock) with an unrelated purified recombinant fusion protein showed a mean lesion score similar to that of unimmunized controls. The increased mean lesion score of controls compared to Experiment-1 indicated the effect of increased length of challenge.

TABLE 4

Intestinal lesion scores of birds immunized with two injections intramuscularly, then infected with a moderate challenge by C. perfringens

| Protein | No. of chickens | Lesion scores | | | | | | Mean |
|---|---|---|---|---|---|---|---|---|
| | | 0 | 1+ | 2+ | 3+ | 4+ | 5+ | |
| Vehicle-only controls | 18 | 1 | 4 | 9 | 2 | 1 | 1 | 2.05 |
| Mock controls | 10 | 0 | 1 | 6 | 3 | 0 | 0 | 2.20 |
| HP* | 17 | 10 | 3 | 4 | 0 | 0 | 0 | 0.64 |
| GPD | 17 | 3 | 8 | 6 | 0 | 0 | 0 | 1.17 |
| tPFOR | 18 | 7 | 4 | 3 | 3 | 0 | 1 | 1.33 |
| FBA | 18 | 2 | 7 | 6 | 2 | 0 | 1 | 1.66 |

*Immunized group had significantly fewer chickens with lesions compared to unimmunized vehicle-only controls; Fisher's exact test, $p \leq 0.05$.

In Experiment-3, the immunization schedule was same as in the Experiment-1 but birds were challenged orally for 5 days. This challenge was considered 'severe' since the birds were fed 2 to 3 times a day to ensure that they always had infected feed available. Birds in this experiment were immunized with alpha-toxoid/toxin, HP, GPD, and tPFOR. A group of birds received alpha-toxoid in the first two injections followed by active, non-toxoided, alpha-toxin in the third. This modification was made since injections with alpha-toxoid alone in the Experiment-1 did not show protection. The unimmunized controls received only Quil-A adjuvant followed by a challenge similar to immunized groups. A group of birds were immunized with a combination GPD and HP (20 μg each) along with Quil-A and challenged similarly as other groups.

This infection challenge was characterized as severe, since lesions scores in non-immunized chickens were greater than in Experiments-1 and 2, an enhancement of severity attributed to constant challenge with infected feed. Alpha-toxin immunized birds, which received two initial injections of alpha-toxoid but a third injection with native, non-toxoided, alpha-toxin showed the greatest protection against heavy challenge (Table 5). Birds immunized with either HP or tPFOR also showed significant protection against severe challenge. Although birds immunized with GPD, FBA and the combination of GPD and HP had mean lesion scores lower than non-immunized controls, no statistical significance was observed.

TABLE 5

Intestinal lesion scores of birds immunized with three injections intramuscularly, then infected with a severe challenge by *C. perfringens*.

Figure 9:
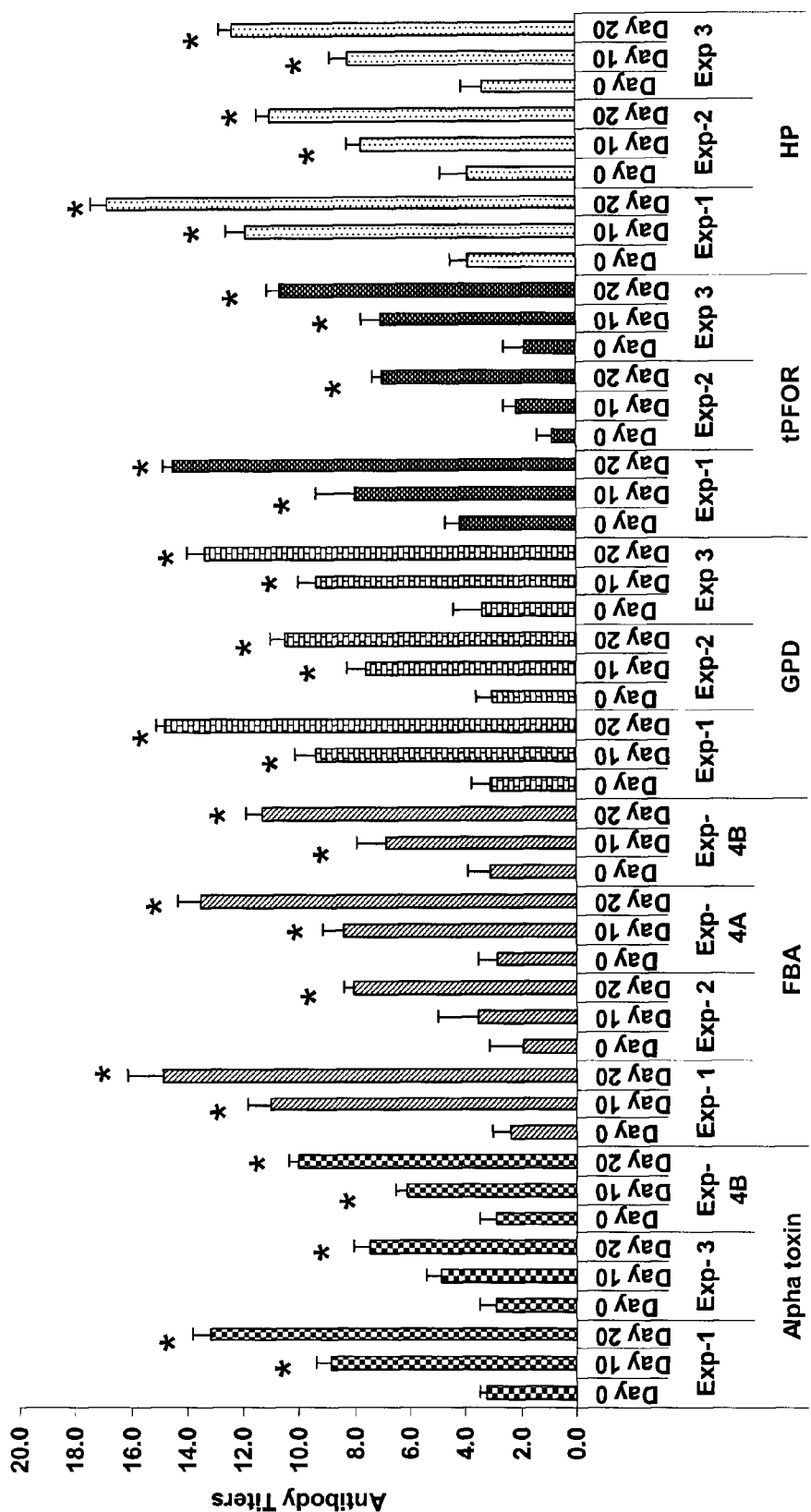
Figure 10:
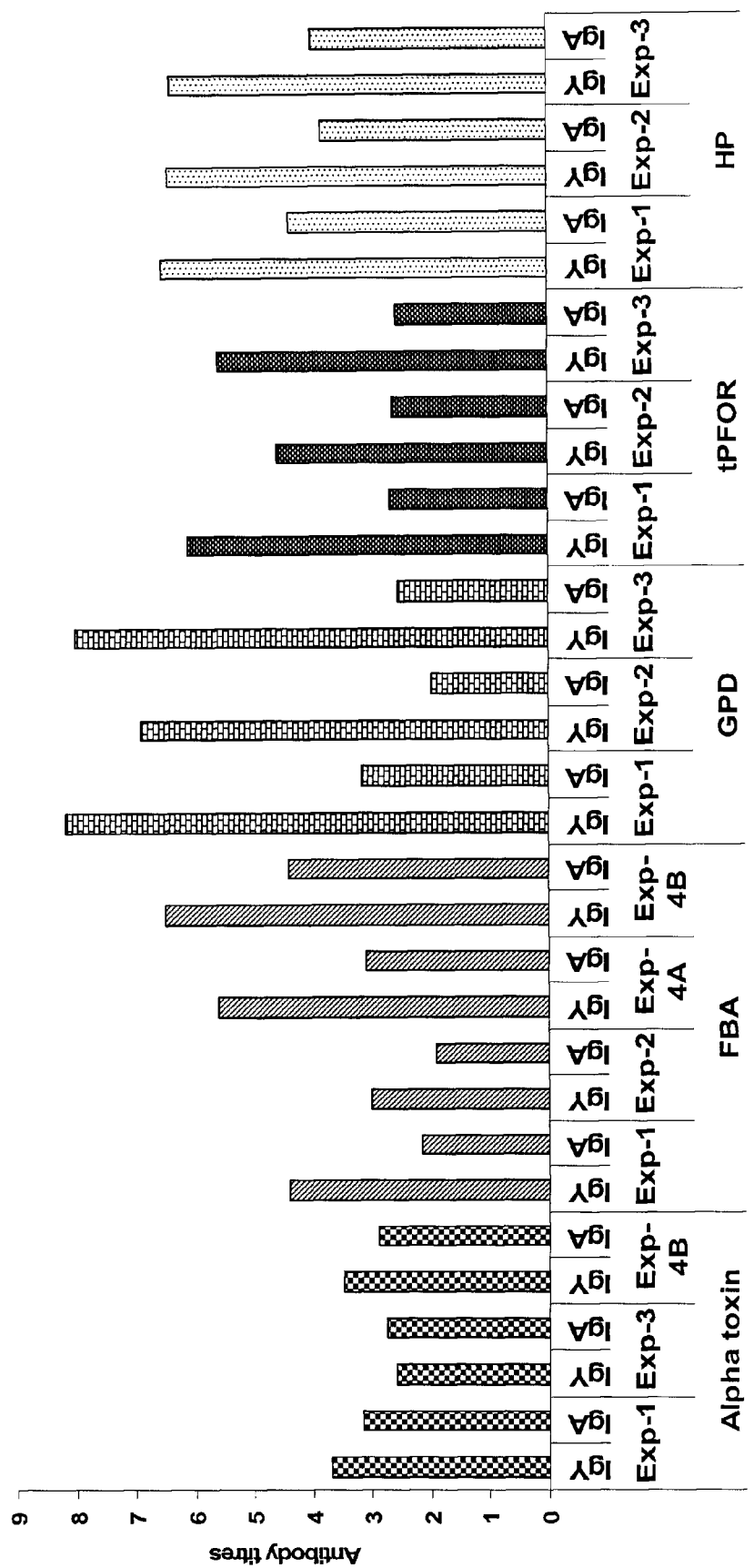

| Protein | No. of chickens | Lesion scores 0 | 1+ | 2+ | 3+ | 4+ | 5+ | Mean |
|---|---|---|---|---|---|---|---|---|
| Vehicle-only controls | 22 | 0 | 5 | 5 | 6 | 4 | 2 | 2.68 |
| Alpha toxoid/toxin*[a] | 19 | 10 | 8 | 1 | 0 | 0 | 0 | 0.53 |
| HP* | 20 | 8 | 6 | 4 | 2 | 0 | 0 | 1.0 |
| GPD | 18 | 4 | 4 | 6 | 1 | 1 | 1 | 1.64 |
| tPFOR* | 19 | 9 | 2 | 6 | 2 | 0 | 0 | 1.05 |
| GPD + HP | 19 | 5 | 5 | 7 | 1 | 1 | 0 | 1.36 |

*Immunized groups that have significantly fewer chickens with lesions compared to unimmunized vehicle-only controls; Fisher's exact test, $p \leqq 0.05$.
[a]Birds in this group received alpha-toxoid in the first two injection and toxin in the third.

In Experiment-4, the immunization schedule was same as in the Experiment-1 and 3, but birds were challenged orally for either 3 ("mild-moderate") or 5 days ("severe"). One group of birds was immunized with FBA and challenged for 3 days and autopsied on the day 6 together with the 3-day challenged unimmunized controls. Two other groups were immunized with either FBA or active (non-toxoided) alpha-toxin, followed by a severe challenge for 5 days. In the active alpha-toxin group, birds received three injections of active alpha-toxin where in the first and the third injections were with 20 μg and the second was reduced to 10 μg since 20 μg dose in the first injection was toxic, causing the death of some birds.

The mean lesion scores in birds of either immunized or unimmunized groups that were challenged for 3 days and autopsied on day 6 (Table 6) were higher than observed in birds of Experiment-1 that were challenged for 3 days and autopsied on day 4 (Table 2). The FBA immunized birds showed significant protection compared to unimmunized controls. In the 5-day-challenged (heavy dose) groups, neither FBA nor the alpha-toxin immunized birds were protected (Table 6). Mean lesion scores of unimmunized controls were comparable to the scores of unimmunized controls in Experiment-3 that also received a severe challenge.

TABLE 6

Intestinal lesion scores of birds immunized with three injections intramuscularly, then infected with mild-moderate or severe challenge by *C. perfringens*

| Protein | No. of chickens | Lesion scores 0 | 1+ | 2+ | 3+ | 4+ | 5+ | Mean |
|---|---|---|---|---|---|---|---|---|
| Groups infected with mild-moderate challenge | | | | | | | | |
| Vehicle-only controls | 10 | 0 | 5 | 2 | 0 | 1 | 2 | 2.3 |
| FBA* | 13 | 4 | 6 | 1 | 1 | 0 | 1 | 1.23 |
| Groups infected with severe challenge | | | | | | | | |
| Vehicle-only controls | 11 | 0 | 3 | 2 | 3 | 1 | 2 | 2.72 |
| Alpha-toxin[a] | 10 | 0 | 2 | 4 | 4 | 0 | 0 | 2.2 |
| FBA | 14 | 1 | 4 | 9 | 0 | 0 | 0 | 1.57 |

*Immunized group that had significantly fewer chickens with lesions compared to unimmunized vehicle-only controls; Fisher's exact test, $p \leqq 0.05$.
[a]Birds in this group received three injections of alpha-toxin where in the first and the third injections were with 20 μg and the second was reduced to 10 μg.

Experiments 1 to 4 show that a degree of immunity to *C. perfringens* infection in broiler chickens can be produced by immunization with several different secreted *C. perfringens* proteins. All the proteins used in immunization, including alpha-toxin, showed significant protection depending on the severity of challenge. Of the five secreted proteins used for immunization experiments, three proteins namely alpha-toxin, HP and tPFOR significantly protected chickens against a heavy challenge, whereas the other two proteins, GPD and FBA, significantly protected against mild challenge. Nevertheless a degree of protection was apparent with these latter proteins even against severe challenge.

Priming with alpha-toxoid and boosting with active toxin showed significant protection, whereas immunization with three injections of either alpha-toxoid or of active toxin did not protect (Tables 3, 6). The failure of active toxin to protect birds against a heavy challenge may have resulted from the toxin's activity on immune system cells. The failure of alpha-toxoid to protect in the Experiment-1 may be the result of a degradation effect of toxoiding on the protein that was observed on SDS-PAGE gel (data not shown). However, it is clear from FIG. 9 that toxoiding was adequate to induce antibodies sufficient for the birds to tolerate the active toxin given as a booster in the Experiment-3. The findings suggest that antibodies to conformational (rather than linear) epitopes of alpha-toxin are needed in protection against NE.

Perfringolysin O (also known as theta toxin), a 52 kDa protein is a potent hemolytic cytolysin that mediates necrosis in the pathogenesis of clostridial gas gangrene (29) and is an important protective immunogen in mouse and guinea-pig gas gangrene models (8). The purified alpha-toxin (Sigma Laboratories) used to immunize birds had traces of perfringolysin O, identified using mass spectrometry (data not shown). However, the relative amounts in the otherwise apparently pure alpha-toxin preparation (assessed by SDS-PAGE) were not quantified. It is possible that the protection observed in alpha-toxoid/toxin immunized birds (Table 5), can be partly attributed to perfringolysin O and that a synergistic effect on the induction of neutralizing antibodies against both the toxins may have contributed to better protection. A synergistic effect of alpha-toxin and perfringolysin O in the pathogenesis of *C. perfringens*-mediated gas gangrene has been observed (2). Proteins identified as important in immunity to NE, may also be involved in the pathogenesis of, and immunity to, gas gangrene.

Among proteins other than alpha-toxin used for immunization, HP showed significant protection against all severities of challenge (Tables 3-5). The truncated PFOR protein also produced significant protection against a heavy challenge in Experiment-3. The tPFOR did not produce significant protection when administered only twice (Experiment-2), possibly because this dosage produced a lower antibody response than observed in birds immunized three times, albeit with a lower dose (FIG. 9). Because of the inconsistency in the protective effect observed with FBA in Experiments 1 and 2, a group of birds in Experiment-4 was immunized with FBA and challenged for 3 or 5 days, then necropsied on day 6 together with the concurrent unimmunized controls. The study confirmed that immunization with FBA provided some protection against mild-moderate challenge. The mean lesion scores in 3-day-challenged birds of either immunized or unimmunized groups (Experiment-4A) were higher than the birds of Experiment-1 that were challenged for 3 days and necropsied on day 4, suggesting that delay to necropsy of birds following 3 day challenge was associated with higher lesion scores.

Experiments 1 to 4 shows that immunization with secreted C. perfingens proteins provides some immunity to birds against C. perfringens infection. Both alpha-toxin and perfringolysin O are regulated in C. perfringens by the VirR-VirS two-component regulon. (4, 26) a regulon that also controls genes involved in energy metabolism such as FBA and NAD-dependent β-hydroxybutyryl co-enzyme-A dehydrogenase, as well as others that may be indirectly involved in bacterial virulence (3, 13, 28). There is growing evidence that certain enzymes, such as GPD and FBA, that are conventionally regarded as metabolic or "house-keeping" enzymes, may have a 'dual role' in both the pathogenesis of, and immunity to, other infections (17, 23). For example, recent studies of the virulence of Group A streptococci (GAS) indicate that GPD assists in attachment of GAS to host cell plasmin and fibronectin receptors (6, 20, 35) and also plays an important role in cellular communication by activating host protein phosphorylation mechanisms (24). Furthermore, GPD has been suggested to be a putative virulence factor in staphylococcal and neisserial infections (9, 22). Interestingly, a recent study showed that antibodies to FBA and GPD of *Streptococcus pneumoniae* showed age-dependent increased serum titers in children of different ages. Immunization of mice with recombinant GPD and FBA showed significant protection against respiratory challenge with virulent *S. pneumoniae* (17). A role for FBA in immunity to Onchocerca volvulus, a filarid nematode causing River Blindness in humans, has also been suggested (21). Similarly, PFOR, an enzyme crucial for anaerobic energy metabolism, has been suggested to have a role in immunity to invasive amoebiasis (31). Hypothetical Protein is a novel protein of C. perfringens of unknown function identified in its genome (27) that may have protease activity (zinc-metallopeptidase) based on the analysis of its protein structure (15).

Figure 8:
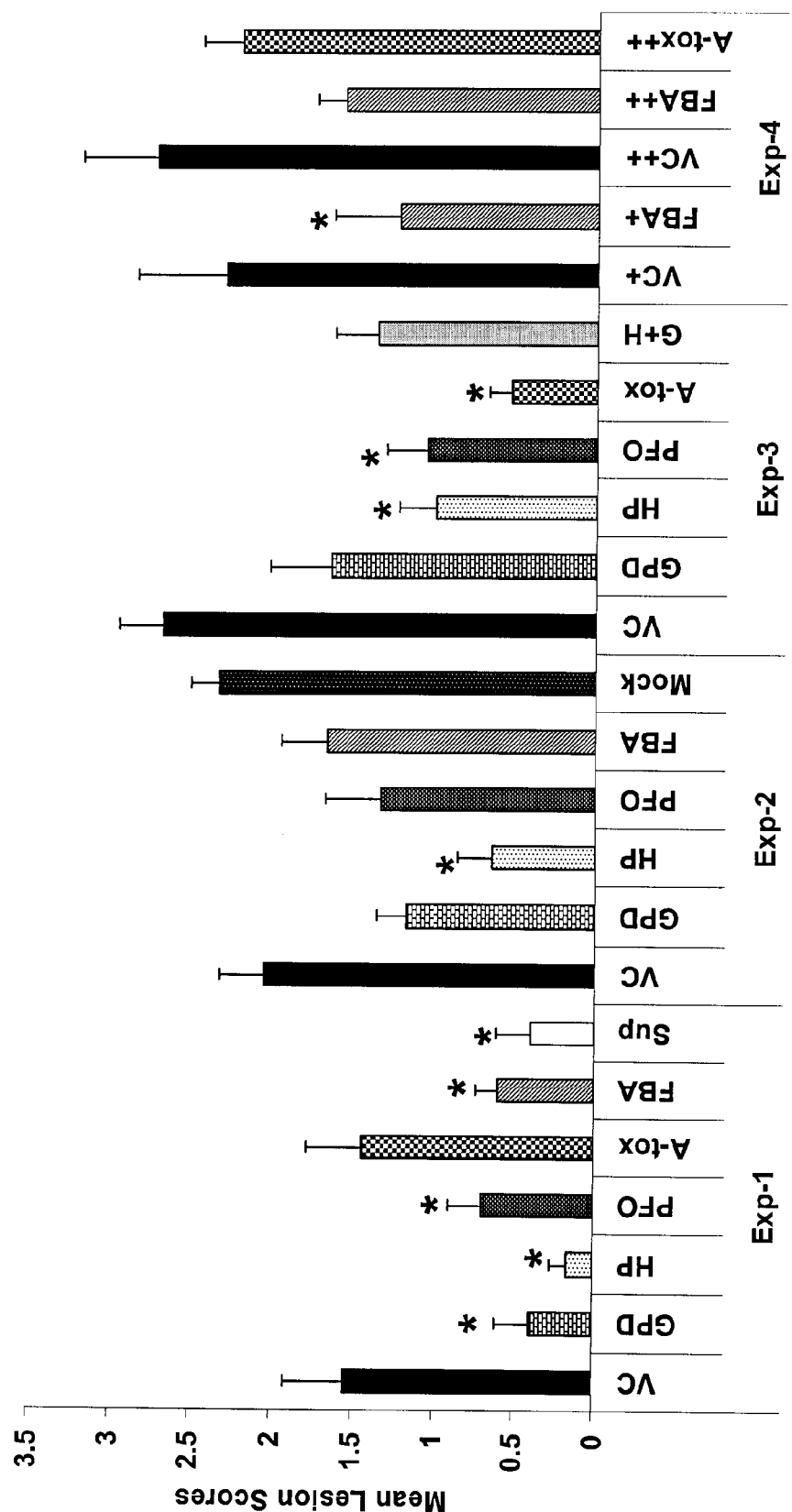

Serum ELISA responses suggested that protection against NE is antibody mediated, since failure of protection in immunized groups in Experiment-2 was associated with low antibody titers (FIG. 8). However, alpha-toxoid/toxin immunized-protected birds had lower antibody titers than toxoid-immunized birds that were not protected, suggesting the importance of conformational epitope-specific neutralizing antibodies, despite in low titers, in mounting a protective immune response. The intestinal antibody response, as expected, was biased towards IgY, since systemic immunization results in more antigen-specific IgY than IgA (FIG. 9). Immunization with HP, that significantly protected birds against all severities of challenge doses, produced higher IgA titers in all three experiments compared to other immunized groups. However, this association of IgA titers to protection was not evident in either alpha-toxoid/toxin or tPFOR immunized groups that were also significantly protected birds against a heavy challenge in Experiment-3.

Experiment 1 to 4 have demonstrated the immunizing ability of *C. perfringens* secreted proteins in protecting against *C. perfringens* in broiler chickens.

Example 5

Epitope Mapping of HP and tPFOR

Since HP and tPFOR, immunogenic secreted proteins of virulent *C. perfringens* were shown to induce significant protection against NE in broiler chickens in Example 4, B-cell epitopes in the primary sequence of both the proteins were identified to provide additional information on the possible antibody recognition sites of these proteins.

To identify B-cell epitopes of HP, a total of 169 peptides were synthesized (SPOTs Synthesis) on a derivatized cellulose membrane (Sigma Genosys Biotechnologies, Woodlands, Tex.). The synthesis of peptides was based on the 1020 amino acid sequence of HP such that synthetic peptides were 12 residues in length with sequential peptides having six residue overlaps. The synthesized membranes containing the synthetic peptides were either probed immediately or stored at −20° C. until needed.

The membrane containing synthesized peptides were washed briefly with methanol and then with Tris-buffered saline (TBS) three times for 5 min and blocked overnight with the blocking buffer (Sigma-Genosys Biotechnologies) with 5% (w/v) sucrose. After blocking, the membranes were washed with TBST (50 mM Tris, pH 8.0, 136 mM NaCl, 2.7 mM KCl and 0.05% Tween-20) for 10 min and incubated with immune sera collected from HP-immunized and protected chickens obtained in Example 4 at a dilution of 1:500 for 2 h at room temperature. Then membranes were washed twice with TBST for 10 min and incubated with goat anti-chicken immunoglobulin Y (IgY: heavy and light chains: Cedarlane Laboratories, Hornby, ON, Canada) at 1:2000 dilution at room temperature for 1 h. After incubation, membranes were washed with TBST and the bound antibodies detected using the chemiluminescent substrate CDP-Star (Applied Biosystems, Foster City, Calif.) and enhancer Nitro-Block II (Applied Biosystems), both diluted to 1:100 with 0.1 M Tris-HCl, 0.1 M NaCl, pH 9.5. The membrane was visualized using a Molecular Light Imager (Berthold, Bad Wildbad, Germany).

The quantified signal of each spot was determined as a relative percentage of a selected spot (peptide) that showed the highest reactivity (designated as 100%) using Win Light Software (Berthold) and the corresponding value was given after substracting the background reactivity of spots developed to the sera from non-immunized, unprotected chickens collected in Example 4. To optimize the appropriate serum dilution for optimum immunoreactivity, the membrane was re-used 3-4 times after regenerating the membrane, performed according to the manufacturer's instructions (Sigma-Genosys Laboratory). Spots showing strong binding intensities were traced back on the primary sequence of HP and immunoreactive regions (epitopes) were identified.

To identify B-cell epitopes of tPFOR, a total of 94 peptides were synthesized on derivatized cellulose membrane (Sigma Genosys Biotechnologies) based on the 564 amino acid sequence of tPFOR such that synthetic peptides were 12 residues in length, with sequential peptides having six residue overlaps. Staining of membrane with immune serum and immuno-reactivity measurement was performed as described for HP.

Figure 11:
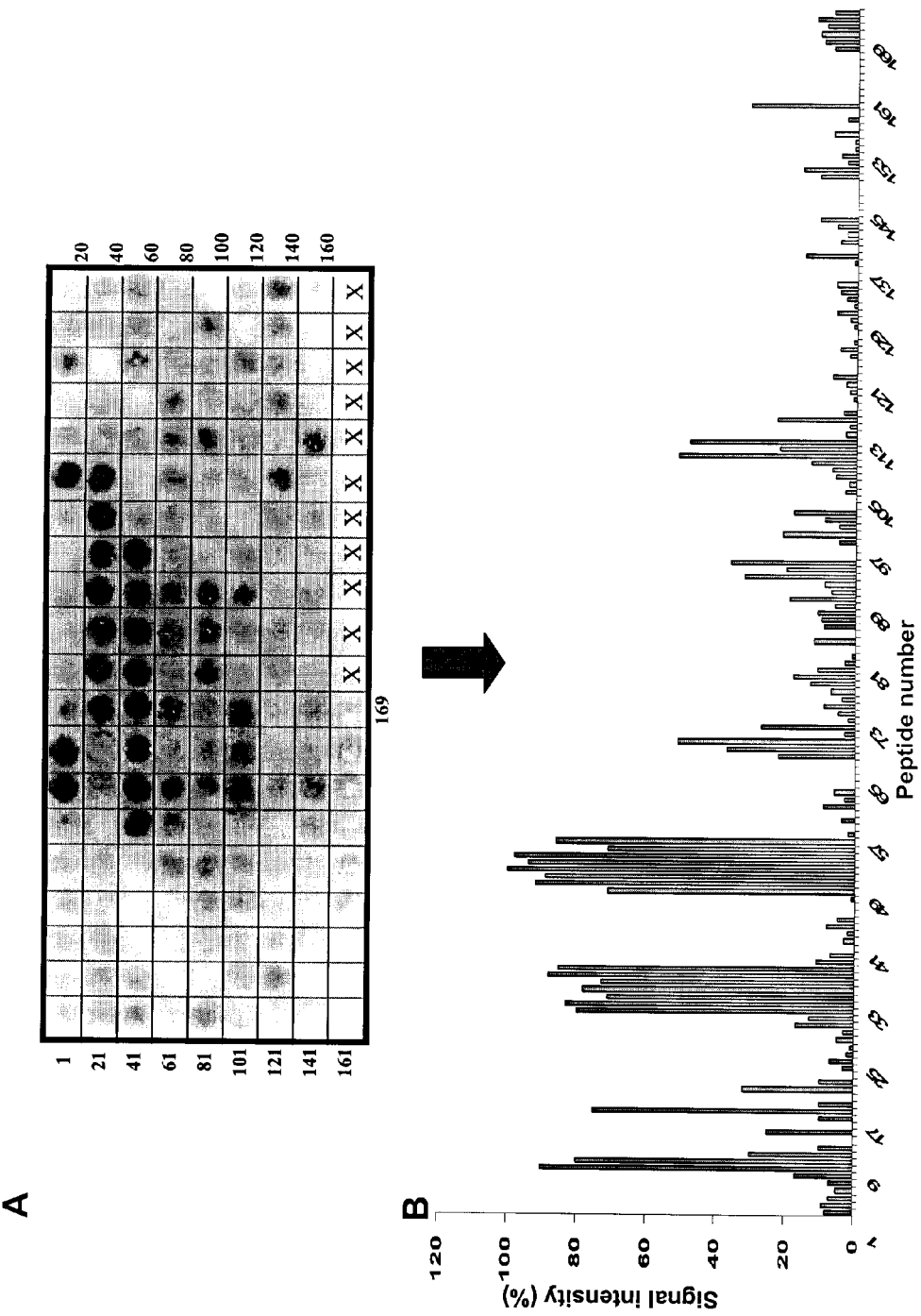

FIG. 11 shows the reactivity of peptides of HP to the serum from HP-immunized and protected birds collected in Example 4. Three distinct regions (amino acid positions; 37-96, 169-246 and 271-324), each comprising 4-6 linear peptides were identified as immunodominant epitopes. On the primary sequence of HP these immunodominant epitopes shown in FIG. 18 were:

```
                                              (SEQ ID NO: 7)
SKDVNSDFNFRIMPMVKNLSGGAFMNAGNGVIGIRPGNQDAILAANKGWG

VAHELGHNFD, (SEQ ID NO: 8)
YDNTFYGKFERQFRERDFGNKNREDIYKSWVVAASDAMELDLTEFFARHG

IRVDDKVKEDLAKYPKPDKKIYYLNDLA,
and (SEQ ID NO: 9)
IKLSFSVDDENKDNILGYEIRRDGKYVGFTSNDSFVDTKSNLDEDGVYVV

TPYD.
```

The first epitope region as defined by reactive peptides was found to have the structurally predicted active site (zinc-binding signature region; GVAHELGHNF—SEQ ID NO: 17) suggestive of a possible zinc-metallopeptidase.

Figure 12:
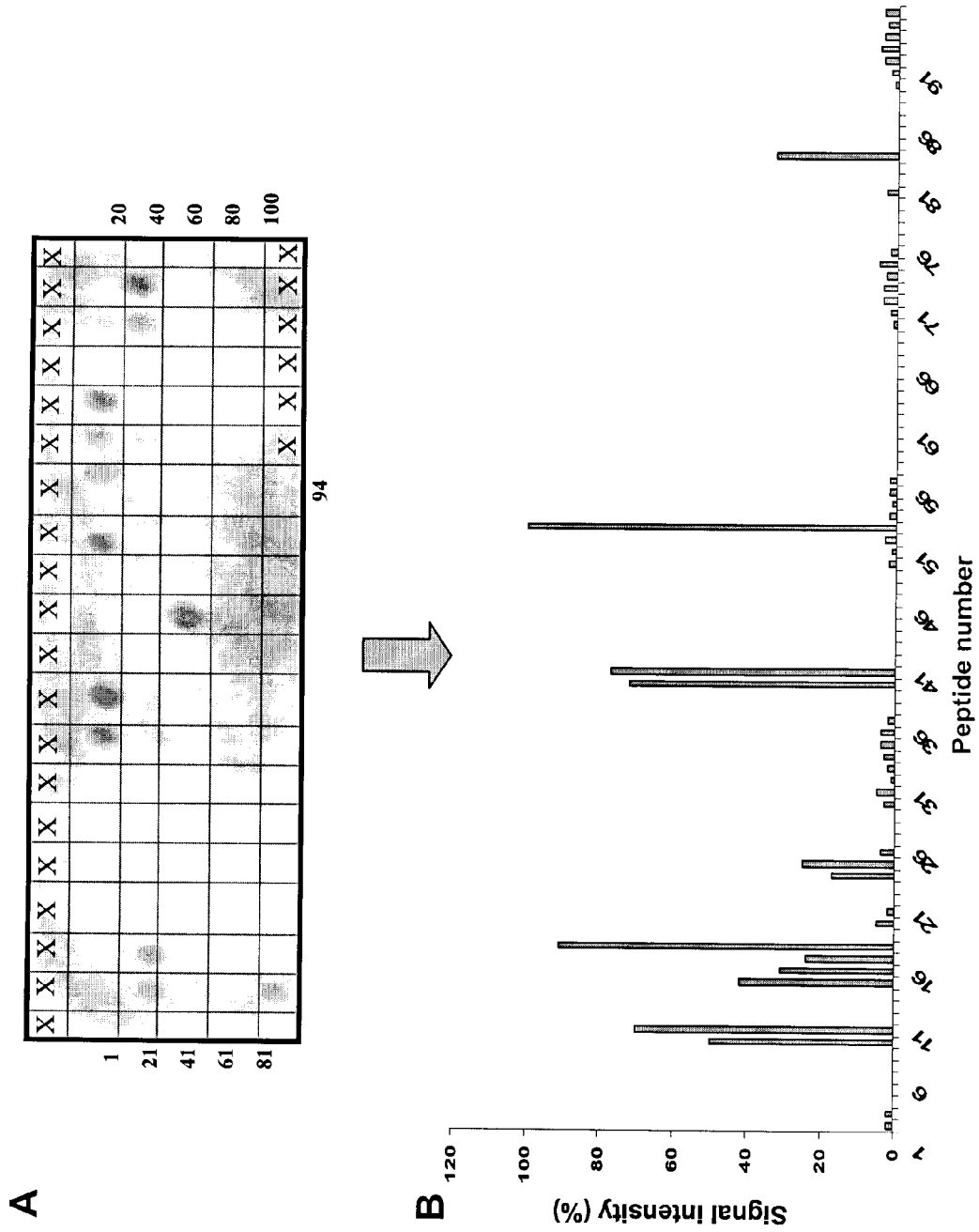
Figure 13:
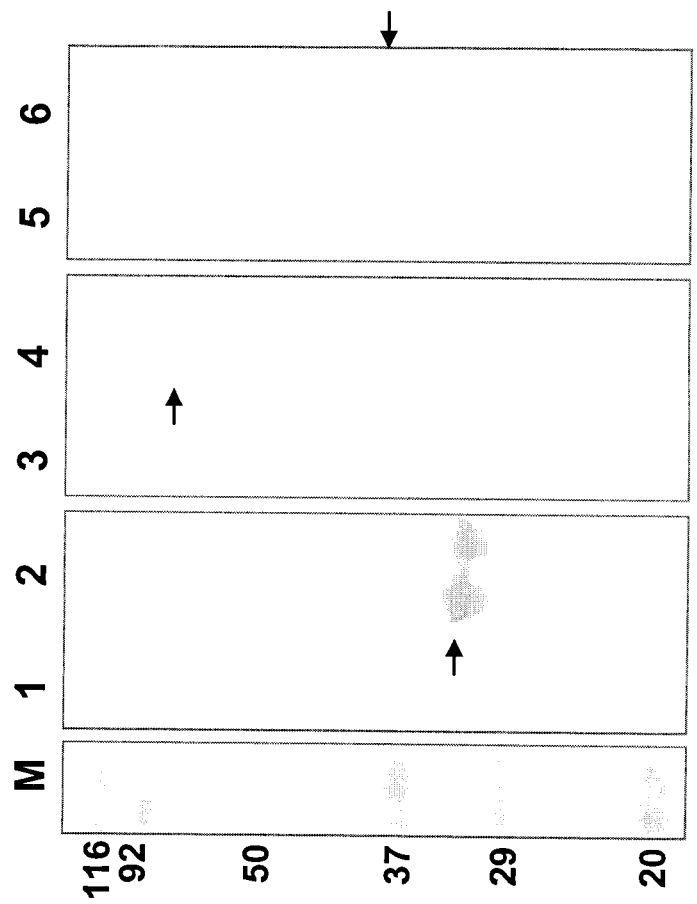
Figure 14:
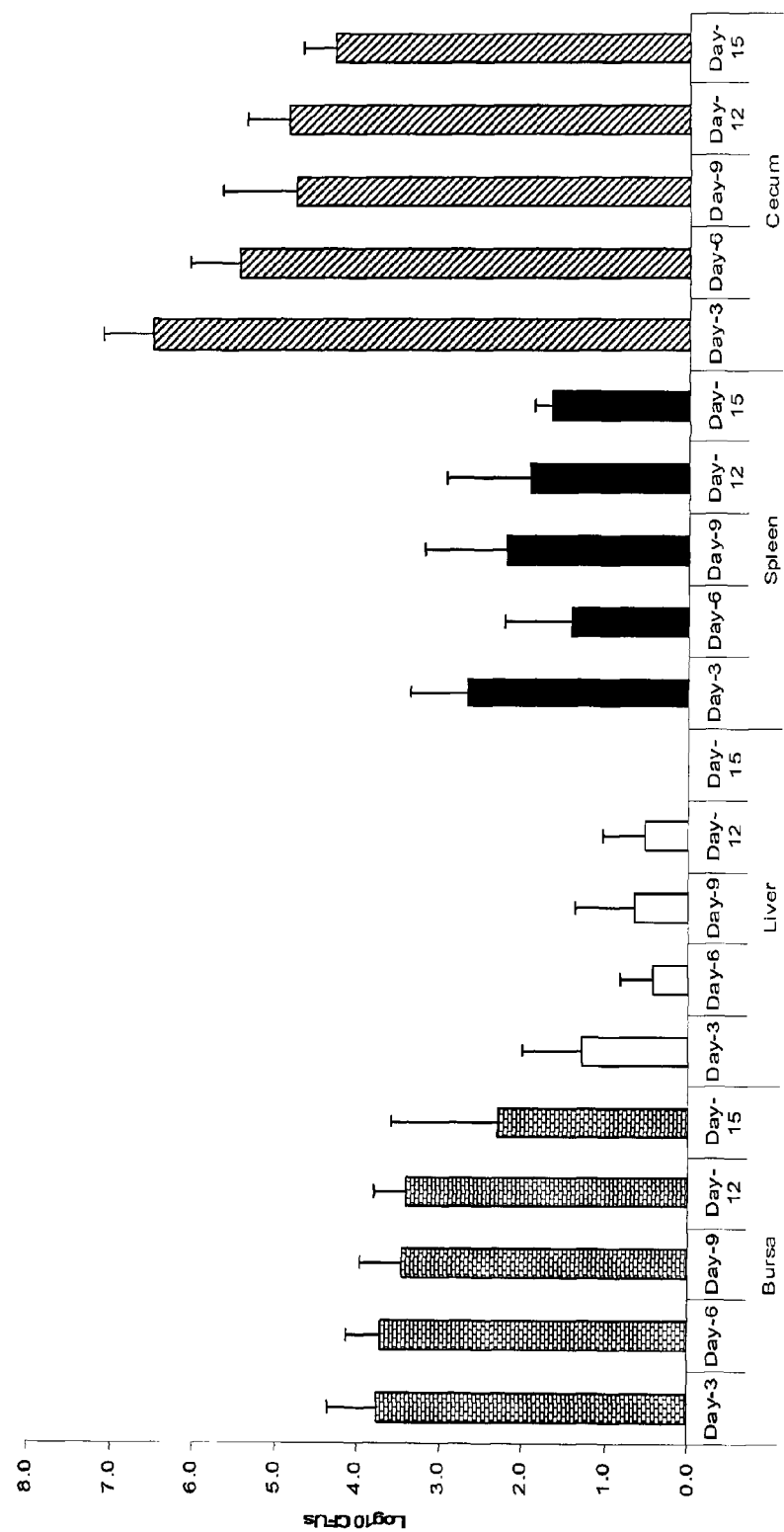

In contrast to HP, five peptides in tPFOR reacted strongly to antibodies (FIG. 12). On the primary sequence of tPFOR, these epitopes shown in FIG. 19 were GYFAYDSKKSGG (SEQ ID NO:10), SYVNKYFVLDGL (SEQ ID NO:11), KDEVVEAKEVPA (SEQ ID NO:12), AKEVPAFIKNIV (SEQ ID NO:13) and AYVCPHATIRPF (SEQ ID NO:14). The fifth peptide was found to have the active site (iron-binding region: AYVCPHAT) of the PFOR enzyme. The third and fourth epitope may be combined as KDEVVEAKEVPAFIKNIV.

Example 6
Construction and Cloning of C. perfringens Antigen-Encoding Nucleic Acids in E. coli* and in *S. Typhimurium*

Several attempts to clone HP (3 kb) into pYA3342 were unsuccessful, possibly due to the relatively large 3 kb size of HP. Hence, based on reactivity of peptides shown in Example 5, a region shown in FIG. 20 of 325 amino acid residues (975 bp) that contained strongly reactive peptides including a predicted active site of the protein was cloned into pYA3342 and expressed as a truncated HP protein (tHP). A hydropathy profile of tHP amino acid sequence using the Hopp-Woods scale available from the database named "Protein Hydrophobicity Plots" which is operated by Colorado State University, Colorado, USA predicted several potentially antigenic (hydrophilic) regions that are likely to be exposed on the surface of tHP upon conformation for recognition by B-cell receptors.

The chromosomal DNA of virulent protective *C. perfringens* strain CP4 was used as the template to amplify fba, tPFOR and tHP nucleic acids using the primers shown in Table 7.

TABLE 7

Primers used to amplify antigen-encoding nucleic acids cloned into pYA3342 (restriction sites in bold letters: GAATTC-EcoRI, GTCGAC-SalI, CTGCAG-PstI)

| Antigen | Direction | Sequence (5'-3') | Amplicon size (bp) |
|---|---|---|---|
| FBA | Forward | CCGCGAATTCATGGCATTAGTTAACGCAAA | 900 |
| | Reverse | CCGCGTCGACAGCTCTGTTTACTGAACCGA | |
| tPFOR | Forward | CCGCGTCGACATTAGAACCAGTTGGAGATA | 1600 |
| | Reverse | CCGCCTGCAGGAAGATCCATTGTGATCTCT | |
| tHP | Forward | CCGCGAATTCTTCTGGGGATTTGATAACTC | 975 |
| | Reverse | CCGCCTGCAGCTCCTCACCTAAAGCTAGTG | |

The PCR amplifications were performed with a platinum PCR-Supermix High-Fidelity Lit (Invitrogen, Burlington, ON, Canada) and the amplicons were purified from agarose gels (PCR purification kit: QIAGEN, Mississauga, ON, Canada), cloned into pBlueScript and the recombinant plasmid then introduced into *E. coli* DH5α competent cells. Positive white colonies were picked from LB agar plates containing ampicillin (50 μg/ml) and grown in LB medium with ampicillin at 37° C. overnight. The recombinant plasmids were then purified and the expected size of the plasmid construct was confirmed on 0.7% agarose gels. After digesting the constructs with appropriate enzymes for the indicated restriction sites (Table 7), the cloned *C. perfringens* nucleic acids purified from the gel (QIAGEN) were then ligated into the appropriately digested and dephosphorylated pYA3342 vector.

The resultant plasmid constructs were introduced into *E. coli* χ6097 competent cells by transformation and the Asd+ transformants were selected on LB plates. All constructs were verified by restriction enzyme analysis and by sequencing both strands of the cloned products. Upon confirmation, recombinant plasmid constructs were isolated and introduced into *Salmonella* χ9241 strains by electroporation and Asd+ transformants selected on LB plates. *Salmonella* χ9241 was further confirmed as containing the individual plasmids by growth in LB medium with and without DAP.

Bacterial Strains and Plasmids

Bacterial strains and plasmids used in Example 6 are listed in Table 8. *Escherichia coli* χ6097, *S. Typhimurium* χ9241 and pYA3342 were kindly provided by R. Curtiss III (The Biodesign Institute, Arizona State University, Tempe, Ariz.). These bacterial strains have a chromosomal deletion of the aspartate B-semialdehyde dehydrogenase (asd) gene which is complemented by an asd+ plasmid (pYA3342) expressing heterologous genes (37), thus ensuring that the recombinant plasmid is stably maintained (38). *Escherichia coli* χ6097 is a derivative of DH5α which was used as an intermediate host to clone the antigen-encoding nucleic acids of interest. *Salmonella* χ9241, an avirulent strain derived from UK-1 strain (*S. Typhimurium* wild-type) has a chromosomal insertion of lacI gene under a BAD (ara) promoter. Thus, antigen expression can be controlled by addition of arabinose to the culture medium. In the absence of arabinose or in vivo, the Ptrc promoter in the plasmid (pYA3342) enables constitutive expression of the recombinant protein. *Escherichia coli* χ6097 and *S. Typhimurium* χ9241 harboring pYA3342 containing *C. perfringens* antigen-encoding nucleic acids were grown in Luria-Bertani (LB) medium (Difco, Detroit, Mich.) and diaminopimelic acid (DAP, 100 µg/ml) was added to the medium when uncomplemented Δasd strains were grown.

To avoid non-specific reactivity, the immune serum was absorbed with sonicated *E. coli* χ6097 (pYA3342) and *S. Typhimurium* χ9241 (pYA3342) cells.

Three recombinant plasmid constructs; pYA3342-fba (950 bp insert), pYA3342-tPFOR (1.6 kb insert) and pYA3342-tHP (1.0 kb insert) were introduced into *E. coli* and *Salmonella* by transformation and by electroporation respectively. FIG. 13 shows the expression of these *C. perfringens* antigen-encoding nucleic acids in *S. Typhimurium* χ9241. The *C. perfringens* polypeptides expressed in both *E. coli* and *S. Typhimurium* reacted strongly to the antigen-specific antibodies. The expression of these *C. perfringens* polypeptides was estimated as ≈1-3% of total proteins expressed by the *Salmonella* vector. However, apart from trace amounts of FBA, none of the proteins was detected in the culture supernatant despite several-fold concentration of the supernatant. No difference was apparent between *E. coli* and *S. Typhimurium* in their expression of *C. perfringens* polypeptides.

TABLE 8

Bacterial strains and plasmids used in Examples 6 to 8

| Bacterial strains and plasmids | Relevant genotype or phenotype | Source |
|---|---|---|
| *E. coli* strain χ6097 | $F^-$ ara Δ(pro-lac) ϕ80dlacZM15 rps L Δasd Δ4 thi | R. Curtiss III |
| DH5α | supE44 lacU169(80lacZM15) hsdR17 recA1 endA1 gyrA96 thi1relA1 | Stratagene |
| *Salmonella enterica* sv. *Typhimurium* strain χ9241 | ΔpabA, ΔpabB, Δasd, ΔaraBAD, relA198:araCPBAD lacI | R. Curtiss III |
| *Clostridium perfringens* strain CP4 | Wild-type, virulent NE isolate | Laboratory |
| Plasmids pYA3342 | $Asd^+$; pBR ori | R. Curtiss III |
| pYA3342-fba | $Asd^+$, fba | This work |
| pYA3342-tPFOR | $Asd^+$, tPFOR | This work |
| pYA3342-tHP | $Asd^+$, tHP | This work |

Example 7

Expression of Recombinant *C. perfringens* Proteins in *E. coli* and in *S. Typhimurium*

Three recombinant plasmid constructs prepared in Example 6; pYA3342-fba (950 bp insert), pYA3342-tPFOR (1.6 kb insert) and pYA3342-tHP (1.0 kb insert) were introduced into *E. coli* and *Salmonella* by transformation and by electroporation respectively.

To confirm the expression of recombinant proteins (FBA, tPFOR and tHP) by *E. coli* and *S. Typhimurium*, cells from cultures grown in LB to OD600≈1.0 were pelleted and resuspended in 2×SDS sample buffer (16) and boiled at 95° C. for 5 min. Recombinant protein expression in *Salmonella* was constitutive but expression was induced in *E. coli* by adding isopropyl-β-D-thiogalactopyranoside (IPTG) to the LB medium at a final concentration of 1 mM. Total proteins expressed by these cells were analyzed by standard SDS-PAGE and immuno-blot techniques. The proteins separated on a 12% polyacrylamide gel were stained by Coomassie stain or transferred onto a nitrocellulose membrane. The blots were developed using protein-specific (FBA, PFOR or HP) antiserum collected from immunized birds in Example 4 as the source of primary antibodies, followed by binding with alkaline phosphatase-conjugated goat anti-chicken IgY (heavy and light chains) antibodies (Cedarlane Laboratories).

Example 8

Protection of Immunized Birds Against Experimentally-Induced Necrotic Enteritis

The use of an attenuated *Salmonella* vector to deliver an antigen by oral delivery is known to the skilled person (36, 39, 40). For example, a ΔpabA, ΔpabB mutant attenuated *Salmonella* vector has been reported to deliver the immunogenic C-terminal domain of alpha-toxin to chickens and induce production of toxin-neutralizing antibodies capable of reducing *C. perfringens*-induced intestinal pathology (39). However, a definitive conclusion on the efficacy of such a vaccine in reducing intestinal pathology in immunized birds cannot be made since this study used few chickens (n=5) in the challenge experiments and required an intramuscular booster with recombinant alpha-toxoid protein to induce sufficient antibody titers.

The experiments in this example demonstrate the ability of an attenuated *S. Typhimurium* vaccine strain in successfully delivering *C. perfringens* antigens through the oral route to elicit immunity against NE in broiler chickens.

The experiments with chickens and the conditions for their use were approved by the University of Guelph Animal Care Committee, in accordance with the guidelines of Canadian Council on Animal Care.

Vaccination and Challenge Procedure For vaccination, the vaccine strains of *Salmonella* were grown in 100 ml of LB broth at 37° C., after inoculation with an overnight culture (2% inoculum) under aeration to an OD600≈0.8 to 0.9. The cells were recovered by centrifugation at 7000 g for 15 min at 4° C. and the pellet was resuspended in 1 ml of PBS containing 1% gelatin (BSG). Viable cell counts (colony-forming units, CFU) were determined by plating serial dilutions onto LB and MacConkey agar plates. The vaccine was prepared freshly each time on the day of immunization.

Commercial day-old male White Plymouth Rock broiler chickens were deprived of food and water for 4 h. Then these day-old chicks were immunized orally with 100 μl of BSG containing $1.2 \times 10^9$ CFU of *Salmonella* χ9241 carrying pYA3342-fba, pYA3342-tPFOR, or pYA3342-tHP plasmid constructs (36). Birds that received *Salmonella* χ9241 (pYA3342, vector-only) were used as negative/vector-only controls and were challenged. Thirty minutes later, the feed and water were given. Chicks were fed an antibiotic-free starter diet containing 20% protein for thirteen days, followed by a formulated wheat-based grower diet containing 28% protein (Arkell Research Station, University of Guelph). On day 14, birds were given a second dose of vaccine ($2 \times 10^9$ cells/bird) and observed for diarrhea and other adverse effects. On day 29, for the experimental infection (challenge) of birds, virulent *C. perfringens* (strain CP4) was grown in cooked meat medium (CMM, Difco) for 24 h at 37° C. Fluid thioglycolate medium (FTG; Difco) was then inoculated with a 3% (v/v) inoculum with *C. perfringens* infected CMM and incubated at 37° C. for 24 h. The growth at 24 h was $\log_{10}$ 8.3±0.1 *C. perfringens* CFU/ml. The infected FTG was then mixed with feed at a ratio of 2:1 (v/w). Infected feed was prepared freshly twice daily and fed to chickens (that were fasted for 20 h prior to initial challenge) twice daily for five days. All birds were individually identified by wing-band numbers.

Colonization of Chickens with the Recombinant *Salmonella* Strain

To determine the colonization of *Salmonella* χ9241 harboring *C. perfringens* antigens after the first oral immunization with $1.2 \times 10^9$ CFU/bird, the liver, spleen, cecum and bursa from each of three birds were collected aseptically at each time point of post-inoculation on days 3, 6, 9, 12 and 15, and tissues were homogenized and plated on Brilliant Green with Sulfa (BSG) plates and viable cells (pink) were counted. Further, the pink colonies were plated on MacConkey plates to confirm the colorless phenotype of *Salmonella* colonies. To confirm that the vaccine strains had not lost the heterologous *C. perfringens* nucleic acids, PCR was performed on representative colonies plated at each time point.

FIG. 14 shows the colonization and tissue distribution of the vaccine strain in liver, spleen, cecum and bursa of immunized birds on days 3, 6, 9, 12 and 15 (three birds each time point) post-immunization. Consistent colonization ($10^4$-$10^6$ CFU/gram) was observed in the cecum and bursa at all times compared to the spleen and liver, in which infection was inconsistent between birds. Infection of the liver was less than that of the spleen, and in both organs, as in the cecum and bursa, reduction of infection was observed over time. Polymerase chain reaction testing on selected colonies confirmed that the vaccine strain had retained the plasmid with cloned *C. perfringens* antigen-encoding nucleic acid.

Protection Assessment

Protection against *C. perfringens* challenge was assessed on the basis of gross intestinal lesion scores at necropsy and by body weight gains of birds during the entire study. Necropsy and scoring of intestinal lesions were described in Example 4. Blind scoring was used to avoid scorer bias. Birds from each group were weighed individually at weekly intervals until necropsy.

Data were analysed to determine whether there was a significant difference between the number of birds with lesions from immunized groups and birds from the non-immunized, vector-only controls. A two-tailed Fisher's exact test determined whether the two groups differed in the proportion with which they fell into the two classifications of either lesions or no lesions, under the null hypothesis that the proportions were the same. Data were analyzed in a 2×2 contingency table with the vector-only control group in one column and immunized groups in the other column. Lesion scores were ranked from 0 to 5+, however, a "protective" response was given to birds with 0 to 1+ lesions. The null hypothesis was rejected at $\alpha=0.05$.

Protection in birds against a *C. perfringens* challenge in vaccinated birds compared to their concurrent vector-only controls (vector plus plasmid without *C. perfringens* insert) was assessed on their gross pathology at necropsy and body weight gains during the experiment. The results of gross pathology are given in Table 9. Birds immunized with *S. Typhimurium* χ9241 carrying pYA3342-fba or pYA3342-tHP were significantly protected against challenge compared to vector-only controls. Birds immunized with *S. Typhimurium* carrying pYA3342 only but not challenged had no lesions.

TABLE 9

Intestinal lesion scores of birds orally immunized with recombinant *S. Typhimurium* X9241 carrying *C. perfringens* nucleic acids, then infected with *C. perfringens* CP4

| Groups | No. of chickens | Lesion scores 0 | 1+ | 2+ | 3+ | 4+ | 5+ | Mean |
|---|---|---|---|---|---|---|---|---|
| Immunized, not challenged | 7 | 7 | — | — | — | — | — | 0 |
| *Salmonella* (vector-only) controls | 20 | — | 6 | 8 | 3 | 1 | 2 | 2.25 |
| *Salmonella* (FBA)* | 17 | 2 | 11 | 4 | — | — | — | 1.11 |
| *Salmonella* (tPFOR) | 17 | — | 6 | 4 | 6 | — | 1 | 1.88 |
| *Salmonella* (tHP)* | 17 | 2 | 9 | 6 | — | — | — | 1.23 |

(*immunized groups that had significantly fewer chickens with lesions compared to vector-only controls; Fisher's exact test, $p < 0.05$)

The increase in body weight gain in birds from all the groups at weekly intervals was constant until challenge. During the challenge period, a significant increase in body weight gains was observed in birds immunized with *S. Typhimurium* χ9241 (pYA3342-fba or pYA3342-tHP) compared to *S. Typhimurium* carrying pYA3342 only controls (data not shown). No significant increase in weight gain was observed in birds immunized with *S. Typhimurium* χ9241 (pYA3342-tPFOR). A group of eight birds that were immunized with *S. Typhimurium* (pYA3342) only but not challenged had the highest weight gains.

Although tPFOR in Example 4 induced significant protection against a severe challenge following intramuscular immunization, it failed to protect birds significantly when administered through the oral vector. However, the trend of protection was apparent when the lesion scores of immunized birds were compared with that of the concurrent controls (Table 9). Failure of tPFOR to protect significantly was perhaps because of poor expression in *Salmonella* in vivo, as evident from low antibody titers to tPFOR in serum (FIG. 16) as well by its lack of reactivity to both intestinal IgY and IgA in Western blot (FIG. 15). It may be possible to improve its expression in *Salmonella* by cloning a smaller region (<1 kb) containing the immuno-reactive peptides (B-cell epitopes) since heterologous proteins of low molecular weight (30-40 kDa) are better expressed by *Salmonella* (36, 40, 41, 42).

Example 9

Antibody Responses to *C. Perfringens* Antigens Delivered by Recombinant *S. Typhimurium* χ9241

The presence of *C. perfringens* antigen-specific antibodies in the serum as well as the intestine of immunized broiler chickens was initially determined using Western blot and then confirmed by ELISA.

Sample Collection

Blood was collected from wing veins of eight birds from each group on week 0 (day 1 of hatch), week 2 (mid-experiment) and week 4 (pre-challenge) to assess the antibody responses to *Salmonella* and *C. perfringens* antigens in serum. Intestinal washings/scrapings from the mucosal side were collected from five birds from each group at necropsy in a PBS solution containing Tween-20 (0.05%) (PBST), EDTA (0.1 mg/ml) and protease inhibitor mix (1:100; Amersham Biosciences Corp., Piscataway, N.J.) and shaken at 4° C. for 3 hr followed by centrifugation at 20000 g×30 min. The supernatant was stored at −20° C. until further use.

Measurement of Antibody in Chicken Sera and Intestinal Washings

To determine the presence of *C. perfringens* antigen-specific IgY and IgA in immunized birds, purified proteins run on a 12% SDS-PAGE gel were reacted with serum or intestinal antibodies obtained from immunized and non-immunized control birds. To detect anti-IgY and anti-IgA antibodies, goat anti-chicken-IgY (heavy and light chains) and IgA (Cedarlane Laboratories) were used as secondary antibodies respectively.

For serum and intestinal ELISA, *C. perfringens* proteins (FBA, tPFOR and HP) purified from *E. coli* were used as coating antigens. An end-point dilution method was used to determine antigen-specific antibody titers by ELISA in vaccinated chickens in comparison to their concurrent controls. Microtiter plates (Immulon-2; Dynatech Laboratories, Chantilly, Va.) were coated with purified proteins (10 µg/ml in 0.1 M carbonate buffer, pH 9.6) for 60 min at 37° C., followed by an overnight incubation at 4° C. Blocking was done at 37° C. for 60 min with PBS containing 3% bovine serum albumen (BSA).

Sera from birds immunized with *Salmonella* χ9241 carrying *C. perfringens* nucleic acids, together with vector-only controls, were serially diluted in PBS containing 1% BSA and incubated for 2 h with protein-coated plates at room temperature. To eliminate non-specific reactivity of antibodies to *E. coli* proteins, serum was absorbed with *E. coli* cells and their lysates. Alkaline phosphatase-conjugated goat anti-chicken IgY (heavy and light chains; diluted 1:5000 in PBST)-1% BSA) were used as secondary antibodies and the color reaction was developed by using an alkaline phosphate substrate kit (Bio-Rad Laboratories) following the manufacturer's instructions. After stopping the reaction with 0.4 M NaOH, the absorbance at 405 nm was measured in an ELISA plate reader. The specific antibody titer of immune serum was expressed as the reciprocal of the serum dilution ($\log_2$) that gave an $A_{405}$ OD value above the cut-off, defined as twice the absorbance value of the control wells run in duplicates.

For intestinal ELISA, antibody titers were determined following the procedure described for serum. Intestinal samples from five chickens per group were collected as described above and the total protein content was measured using PlusOne™2-D Quant kit (Amersham Biosciences, San Francisco, Calif.) and used as source of primary antibody after keeping the protein content of initial dilution constant. Alkaline phosphatase conjugated goat anti-chicken IgY and IgA were used as secondary antibodies at dilutions of 1:4000 and 1:2000 respectively. The end-point titers were determined as described above for serum ELISA.

To assess anti-*Salmonella* ELISA responses in the serum and intestine of birds immunized with recombinant *Salmonella* expressing a *C. perfringens* antigen, as well as vector-only infected control birds, a *Salmonella* lysate was used. To make lysates, *S. Typhimurium* carrying pYA3342 without an inserted *C. perfringens* nucleic acid was grown in LB medium to an OD600≈0.8 and the cells were then pelleted and resuspended in the 0.1 M carbonate buffer, before sonication on ice for 5-10 min. The resultant lysate was used as a coating antigen (10 µg protein/ml) in ELISA as described, and *Salmonella* antibody titers were determined as outlined above.

For serum ELISA, a one-way ANOVA was used to determine significant ($p<0.05$) differences in the antibody titers between pre-immunized and immunized birds across all groups. Statistical analysis could not be made on intestinal ELISA, since the intestinal washings were collected only at the time of necropsy.

Figure 15:
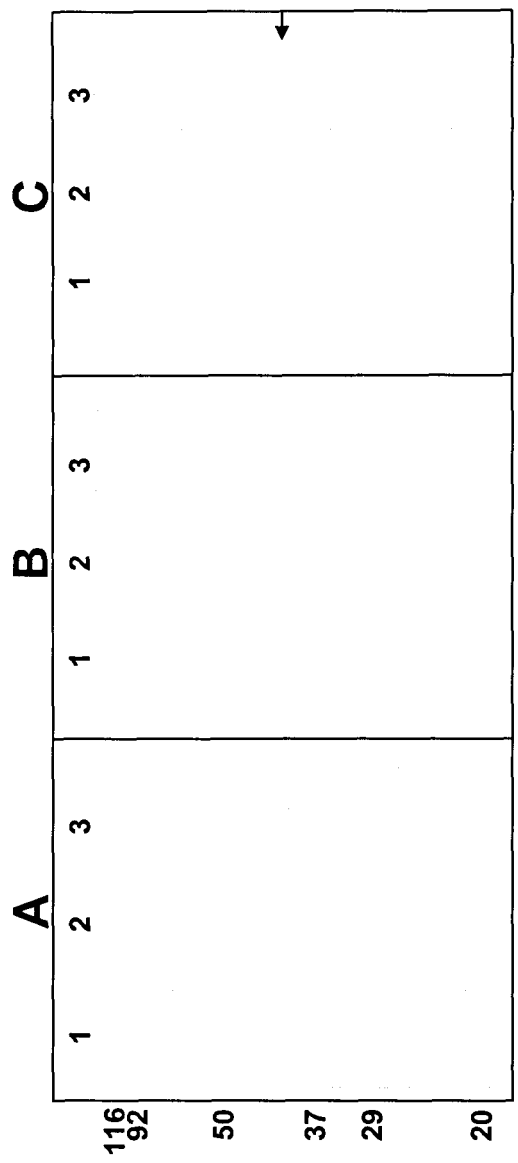

In IgY immunoblots using serum and intestinal washings from immunized birds at the time of necropsy, tHP showed the strongest signal, followed by FBA. Truncated PFOR showed a weaker reactivity (FIG. 15). Intestinal IgA to *C. perfringens* proteins was evident only in birds immunized with *S. Typhimurium* χ9241 expressing tHP. No intestinal antibodies were detected against tPFOR in Western blots (FIG. 15).

Figure 16:
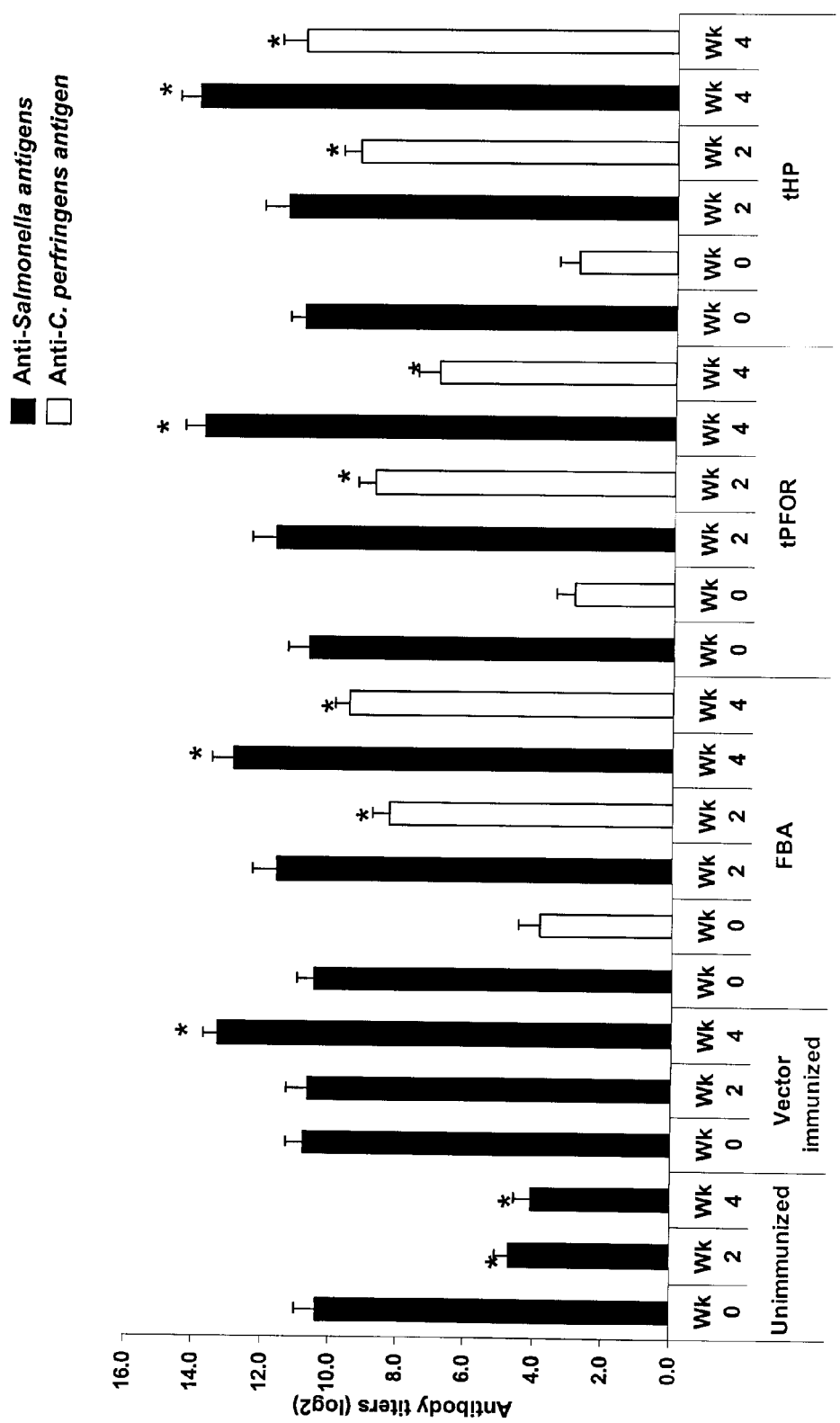
Figure 17:
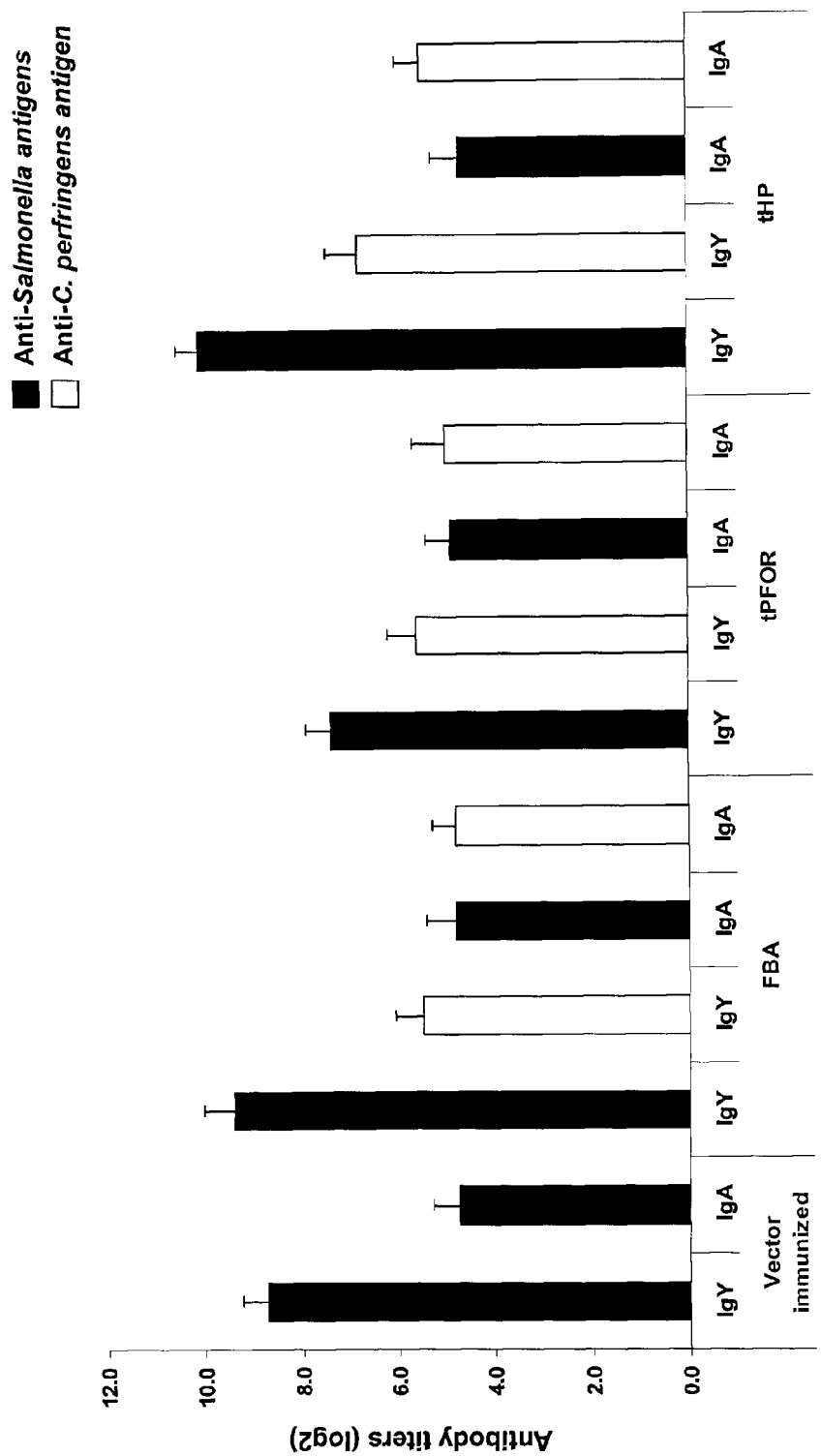

In ELISA experiments, all birds immunized orally with recombinant *S. Typhimurium* carrying *C. perfringens* antigens, as well as birds orally administered vector-only controls, had *S. Typhimurium* antibodies in their serum as well as intestine (FIGS. 16, 17). In the small intestine, IgY titers to *S. Typhimurium* antigens were higher than IgA titers (FIG. 17). The *Salmonella* titers in non-immunized birds declined over time whereas those in immunized birds increased markedly (FIG. 16).

Birds immunized with *S. Typhimurium* χ9241 (pYA3342-fba, pYA3342-tPFOR or pYA3342-tHP) had significant antigen-specific antibody titers in their serum compared to their pre-immunization status (FIG. 16). Serum titers to *Salmonella* were higher than those to *C. perfringens* antigens. Immunized birds developed intestinal antigen-specific IgY and IgA responses to *C. perfringens* antigens, but apart from the *Salmonella* χ9241 (pYA3342-tHP) immunized birds that had relatively higher IgY titers (FIG. 17), no difference was observed between their IgY and IgA titers. Intestinal IgA titers to both *Salmonella* and *C. perfringens* antigens were similar.

REFERENCES

1. Alape-Giron, A., M. Flores-Diaz, I. Guillouard, C. E. Naylor, R. W. Titball, A. 2000. Identification of residues critical for toxicity in *Clostridium perfringens* phospholipase C, the key toxin in gas gangrene. Eur. J. Biochem. 267:5191-5197.
2. Awad, M. M., D. M. Ellemor, R. L. Boyd, J. J. Emmins, and J. I. Rood. 2001. Synergistic effects of alpha-toxin and perfringolysin 0 in *Clostridium perfringens* mediated gas gangrene. Infect. Immun. 69:7904-7910.

3. Banu, S., K. Ohtani, H. Yaguchi, T. Swe, S. T. Cole, H. Hayashi, and T. Shimizu. 2000. Identification of novel VirR/VirS-regulated genes in *Clostridium perfringens*. Mol. Microbiol. 35:854-864.
4. Ba-Thein, W., M. Lyristis, K. Ohtani, I. T. Nisbet, H. Hayashi, J. I. Rood, and T. Shimizu. 1996. The virR/virS locus regulates the transcription of genes encoding extracellular toxin production in *Clostridium perfringens*. J. Bacteriol. 178:2514-2520.
5. Bennett, A. M., T. Lescott, R. J. Phillpotts, M. Mackett, and R. W. Titball. 1999. Recombinant vaccinia viruses protect against *Clostridium perfringens* alpha-toxin. Viral Immunol. 12:97-105.
6. Boel, G., H. Jin, and V. Pancholi. 2005. Inhibition of cell surface export of group A Streptococcal anchorless surface dehydrogenase affects bacterial adherence and antiphagocytic properties. Infect. Immun. 73:6237-6248.
7. Eaton, J. T., C. E. Naylor, A. M. Howells, D. S. Moss, R. W. Titball, and A. K. Basak. 2002. Crystal structure of the *C. perfringens* alpha-toxin with the active site closed by a flexible loop region. J. Mol. Biol. 319:275-281.
8. Efimova, M. G., V. A. Blagoveshchenskii, and B. V. Khatuntseva. 1982. Protective properties of theta-hemolysin obtained by affinity chromatography. Zh. Mikrobiol. Epidemiol. Immunobiol. 12:87-92.
9. Grifantini, R., E. Bartolini, A. Muzzi, M. Draghi, E. Frigimelica, J. Berger, F. Randazzo, and G. Grandi. 2002. Gene expression profile in *Neisseria meningitidis* and *Neisseria lactamica* upon host-cell contact: From basic research to vaccine development. Ann. N.Y. Acad. Sci. 975:202-216.
10. Heier, B. T., A. Lovland, K. B. Soleim, M. Kaldhusdal, and J. Jarp. 2001. A field study of naturally occurring specific antibodies against *Clostridium perfringens* alpha-toxin in Norwegian broiler flocks. Avian Dis. 45:724-732.
11. Ito, A. 1968. Alpha-toxoid of *Clostridium perfringens*. I. purification and toxoiding of alpha-toxin of *C. perfringens*. Jpn. J. Med. Sci. Biol. 21:379-391.
12. Kaldhusdal, M., and A. Lovland. 2000. Necrotic enteritis: The economical impact of *Clostridium perfringens* is greater than anticipated. World Poultry 16:50-51.
13. Kawsar, H. I., K. Ohtani, K. Okumura, H. Hayashi, and T. Shimizu. 2004. Organization and transcriptional regulation of myo-inositol operon in *Clostridium perfringens*. FEMS Microbiol. Lett. 235:289-295.
14. Keyburn, A. L., S. A. Sheedy, M. E. Ford, M. M. Williamson, M. M. Awad, J. I. Rood, and R. J. Moore. 2006. The alpha-toxin of *Clostridium perfringens* is not an essential virulence factor in necrotic enteritis in chickens. Infect. Immun. 74:6496-6500.
15. Kulkarni, R. R., V. R. Parreira, S. Sharif, and J. F. Prescott. 2006. *Clostridium perfringens* antigens recognized by broiler chickens immune to necrotic enteritis. Clin. Vaccine Immunol. 13:1358-1362.
16. Laemmli, U. K. 1970. Cleavage of structural proteins during the assembly of the head of bacteriophage T4. Nature 227:680-685.
17. Ling, E., G. Feldman, M. Portnoi, R. Dagan, K. Overweg, F. Mulholland, V. Chalifa-Caspi, J. Wells, and Y. Mizrachi-Nebenzahl. 2004. Glycolytic enzymes associated with the cell surface of *Streptococcus pneumoniae* are antigenic in humans and elicit protective immune responses in the mouse. Clin. Exp. Immunol. 138:290-298.
18. Logan, A. J., E. D. Williamson, R. W. Titball, D. A. Percival, A. D. Shuttlewoth, J. W. Conlan, and D. C. Kelly. 1991. Epitope mapping of the alpha-toxin of *Clostridium perfringens*. Infect. Immun. 59:4338-4342.
19. Lovland, A., M. Kaldhusdal, K. Redhead, E. Skjerve, and A. Lillehaug. 2004. Maternal vaccination against subclinical necrotic enteritis in broilers. Avian Pathol. 33:83-92.
20. Madureira, P., M. Baptista, M. Vieira, V. Magalhaes, A. Camelo, L. Oliveira, A. Ribeiro, D. Tavares, P. Trieu-Cuot, M. Vilanova, and P. Ferreira. 2007. *Streptococcus agalactiae* GAPDH is a virulence-associated immunomodulatory protein. J. Immunol. 178:1379-1387.
21. McCarthy, J. S., M. Wieseman, J. Tropea, D. Kaslow, D. Abraham, S. glycolytic enzyme fructose-1,6-bisphosphate aldolase as a target for a protective immune response in humans. Infect. Immun. 70:851-858.
22. Modun, B., and P. Williams. 1999. The staphylococcal transferrin-binding protein is a cell wall glyceraldehyde-3-phosphate dehydrogenase. Infect. Immun. 67:1086-1092.
23. Pancholi, V., and G. S. Chhatwal. 2003. Housekeeping enzymes as virulence factors for pathogens. Int. J. Med. Microbiol. 293:391-401.
24. Pancholi, V., and V. A. Fischetti. 1997. Regulation of the phosphorylation of human pharyngeal cell proteins by group A streptococcal surface dehydrogenase: Signal transduction between streptococci and pharyngeal cells. J. Exp. Med. 186:1633-1643.
25. Prescott, J. F. 1979. The prevention of experimentally induced necrotic enteritis in chickens by avoparcin. Avian Dis. 23:1072-1074.
26. Shimizu, T., W. Ba-Thein, M. Tamaki, and H. Hayashi. 1994. The virR gene, a member of a class of two-component response regulators, regulates the production of perfringolysin 0, collagenase, and hemagglutinin in *Clostridium perfringens*. J. Bacteriol. 176:1616-1623.
27. Shimizu, T., K. Ohtani, H. Hirakawa, K. Ohshima, A. Yamashita, T. Shiba, N. Ogasawara, M. Hattori, S. Kuhara, and H. Hayashi. 2002. Complete genome sequence of *Clostridium perfringens*, an anaerobic flesh-eater. Proc. Natl. Acad. Sci. U.S.A. 99:996-1001.
28. Shimizu, T., K. Shima, K. Yoshino, K. Yonezawa, T. Shimizu, and H. Hayashi. 2002. Proteome and transcriptome analysis of the virulence genes regulated by the VirR/VirS system in *Clostridium perfringens*. J. Bacteriol. 184:2587-2594.
29. Stevens, D. L., and A. E. Bryant. 1993. Role of theta toxin, a sulfhydryl-activated cytolysin, in the pathogenesis of clostridial gas gangrene. Clin. Infect. Dis. 16 Suppl 4:S195-9.
30. Stevens, D. L., R. W. Titball, M. Jepson, C. R. Bayer, S. M. Hayes-Schroer, and A. E. Bryant. 2004. Immunization with the C-domain of alpha-toxin prevents lethal infection, localizes tissue injury, and promotes host response to challenge with *Clostridium perfringens*. J. Infect. Dis. 190:767-773.
31. Thammapalerd, N., D. Kotimanusvanij, M. Duchene, J. A. Uperoft, R. Mitchell, A. Healey, N. Samarawickrema, S. Tharavanij, G. Wiedermann, and P. Uperoft. 1996. Pyruvate: Ferredoxin oxidoreductase from *Entamoeba histolytica* recognized by a monoclonal antibody. Southeast Asian J. Trop. Med. Public Health 27:63-70.
32. Thompson, D. R., V. R. Parreira, R. R. Kulkarni, and J. F. Prescott. 2006. Live attenuated vaccine-based control of necrotic enteritis of broiler chickens. Vet. Microbiol. 113:25-34.
33. Titball, R. W., A. M. Fearn, and E. D. Williamson. 1993. Biochemical and immunological properties of the C-terminal domain of the alpha-toxin of *Clostridium perfringens*. FEMS Microbiol. Lett. 110:45-50.

34. Williamson, E. D., and R. W. Titball. 1993. A genetically engineered vaccine against the alpha-toxin of *Clostridium perfringens* protects mice against experimental gas gangrene. Vaccine 11:1253-1258.
35. Winram, S. B., and R. Lottenberg. 1996. The plasmin-binding protein plr of group A streptococci is identified as glyceraldehyde-3-phosphate dehydrogenase. Microbiology 142 (8):2311-2320.
36. Konjufca V, Wanda S Y, Jenkins M C, Curtiss R, 3rd. A recombinant attenuated *Salmonella enterica serovar Typhimurium* vaccine encoding *Eimeria acervulina* antigen offers protection against *E. acervulina* challenge. Infect Immun 2006; 74(12):6785-96.
37. Galan J E, Nakayama K, Curtiss R, 3rd. Cloning and characterization of the asd gene of *Salmonella Typhimurium*: use in stable maintenance of recombinant plasmids in *Salmonella* vaccine strains. Gene 1990; 94(1):29-35.
38. Curtiss R, 3rd, Galan J E, Nakayama K, Kelly S M. Stabilization of recombinant avirulent vaccine strains in vivo. Res Microbiol 1990; 141(7-8):797-805.
39. Zekarias B, Mo H, Curtiss R, 3rd. Recombinant attenuated *Salmonella* expressing the carboxy-terminal domain of alpha-toxin from *Clostridium perfringens* induces protective responses against necrotic enteritis in chickens. Clin Vaccine Immunol 2008; Mar. 12: Epub ahead of print.
40. Wyszynska A, Raczko A, L is M, Jagusztyn-Krynicka E K. Oral immunization of chickens with avirulent *Salmonella* vaccine strain carrying *C. jejuni* 72Dz/92 cjaA gene elicits specific humoral immune response associated with protection against challenge with wild-type *Campylobacter*. Vaccine 2004; 22(11-12):1379-89.
41. Kang H Y, Srinivasan J, Curtiss R, 3rd. Immune responses to recombinant pneumococcal PspA antigen delivered by live attenuated *Salmonella enterica* serovar Typhimurium vaccine. Infect Immun 2002; 70(4):1739-49.
42. Oliveira A F, Ferraz L C, Brocchi M, Roque-Barreira M C. Oral administration of a live attenuated *Salmonella* vaccine strain expressing the VapA protein induces protection against infection by *Rhodococcus equi*. Microbes Infect 2007; 9(3):382-90.

All documents mentioned herein are hereby incorporated by reference.

The above-described embodiments are intended to be examples and alterations and modifications may be effected thereto, by those of skill in the art, without departing from the scope of the invention which is defined by the claims appended hereto.

---

We claim:

1. An immunogenic composition for inducing an immune response against *C. perfringens* in an animal comprising an isolated *C. perfringens* secreted antigenic polypeptide, a pharmaceutically acceptable carrier, and an adjuvant, wherein the antigenic polypeptide comprises an amino acid sequence selected from the group consisting of SEQ ID NO: 1, SEQ ID NO:2, SEQ ID NO:7, SEQ ID NO:8, SEQ ID NO:9, and SEQ ID NO:16.

2. The immunogenic composition of claim 1, wherein the antigenic polypeptide comprises an amino acid sequence selected from the group consisting of SEQ ID NO:7, SEQ ID NO:8, SEQ ID NO:9 and SEQ ID NO:16.

3. The immunogenic composition of claim 1, wherein the antigenic polypeptide comprises the amino acid sequence of SEQ ID NO:1.

4. The immunogenic composition of claim 1, wherein the antigenic polypeptide comprises the amino acid sequence of SEQ ID NO:2.

5. The immunogenic composition of claim 1, wherein the animal is a bird selected from the group consisting of chicken, turkey, goose, duck, pheasant, quail, pigeon and ostrich.

6. The immunogenic composition of claim 5, wherein the bird is a chicken.

7. The immunogenic composition of claim 1, wherein said secreted antigenic polypeptide is comprised within a recombinant cell with the proviso that the recombinant cell is not *C. perfringens*.

8. The immunogenic composition of claim 7, wherein the recombinant cell is a bacterial cell.

9. The immunogenic composition of claim 1, further comprising a preservative.

10. The immunogenic composition of claim 9, formulated for intramuscular, subcutaneous, intravenous, intranasal, intradermal, intrabursal, in ovo, ocular, oral, intra-tracheal or intra-bronchial delivery.

11. A feed additive comprising the immunogenic composition of claim 1.

12. A method of immunizing or treating a subject against *C. perfringens* induced necrotic enteritis comprising administering an effective amount of the immunogenic composition of claim 1 to a subject.

13. The immunogenic composition of claim 1, wherein the animal is a pig or cattle.

14. The method of claim 12 wherein the subject is a pig, cattle or bird.

15. The immunogenic composition of claim 13, wherein the animal is cattle.

* * * * *

UNITED STATES PATENT AND TRADEMARK OFFICE
CERTIFICATE OF CORRECTION

| | | |
|---|---|---|
| PATENT NO. | : 8,501,190 B2 | Page 1 of 2 |
| APPLICATION NO. | : 12/666264 | |
| DATED | : August 6, 2013 | |
| INVENTOR(S) | : Prescott et al. | |

It is certified that error appears in the above-identified patent and that said Letters Patent is hereby corrected as shown below:

Title Page

In column 2 (page 2, item 56) at line 23, Under Other Publications, Change "Infecttion" to --Infection--.

In column 2 (page 2, item 56) at line 37, Under Other Publications, Change "cjaAgene" to --cjaA gene--.

In the Specification

In column 6 at line 42, Change "in 3." to --in J.--.

In column 6 at line 62, Change "FIG." to --FIGS.--.

In column 8 at line 67, Change "Eschercichia" to --Escherichia--.

In column 9 at line 51, Change "lichenifonnis" to --licheniformis--.

In column 10 at line 48, Change "intradermaly," to --intradermally,--.

In column 11 at line 23, Change "well know" to --well known--.

In column 12 at line 61, Change "Necrotis" to --Necrotic--.

In column 14 at line 7, Change "(perfringolysin 0," to --(perfringolysin O,--.

In column 15 at line 56, Change "($OD_{500}$-0.5)." to --($OD_{600}$-0.5).--.

Signed and Sealed this
Fourteenth Day of April, 2015

Michelle K. Lee
*Director of the United States Patent and Trademark Office*

CERTIFICATE OF CORRECTION (continued)
U.S. Pat. No. 8,501,190 B2

In column 15 at line 65, Change "lyzozyme" to --lysozyme--.

In column 23 at line 22, Change "perfingens" to --perfringens--.

In column 24 at line 62 (approx.), Change "substracting" to --subtracting--.

In column 32 at line 66, Change "perfringolysin 0" to --perfringolysin O--.

In column 33 at line 3, Change "VirRIVirS" to --VirR/VirS--.

In column 34 at line 32, Change "0," to --O,--.

In column 36 at line 3, Change "L is M," to --Lis M,--.

SEQUENCE LISTING

```
<160> NUMBER OF SEQ ID NOS: 17

<210> SEQ ID NO 1
<211> LENGTH: 1687
<212> TYPE: PRT
<213> ORGANISM: Clostridium perfringens

<400> SEQUENCE: 1

Met Asn Lys Arg Lys Ile Ala Ala Ile Ile Leu Ala Thr Met Ile Thr
1               5                   10                  15

Asn Leu Ser Ala Thr Thr Ile Asp Val Leu Ala Gln Glu Leu Asn Thr
            20                  25                  30

Lys Asn Asn Ser Lys Val Glu Val Ser His Asp Glu Ser His Gln
        35                  40                  45

Ala Arg Val Ser Lys Phe Asp Leu Tyr Asn Ser Asp Lys Leu Asp Ala
    50                  55                  60

Tyr Asn Gln Glu Phe Gln Ile Asn Arg Ser Asn Ile Lys Ser Ile Thr
65                  70                  75                  80

Asn Asn Gly Gly Lys Tyr Asn Ser Ser Thr Ile Asp Lys Ala Ile Asp
                85                  90                  95

Gly Asn Leu Glu Thr His Trp Glu Thr Gly Lys Pro Asn Asp Ser Asn
            100                 105                 110

Phe Thr Asn Glu Val Val Val Thr Phe Asn Glu Ile Thr Asn Ile Asp
        115                 120                 125

Arg Ile Val Tyr Ser Ala Arg Arg Asp Ser Ala Arg Gly Lys Gly Phe
    130                 135                 140

Ala Lys Glu Phe Glu Ile Tyr Ala Ser Leu Lys Asp Glu Gly Asp Asp
145                 150                 155                 160

Phe Asn Leu Val Ser Ser Gly Glu Tyr Thr Glu Ser Thr Arg Asp Leu
                165                 170                 175

Val Glu Ile Lys Phe Asn Pro Thr Asp Phe Lys Arg Leu Lys Phe Lys
            180                 185                 190

Phe Lys Lys Ala Asp Gln Asn Trp Ala Ser Ser Ala Glu Phe Met Phe
```

-continued

```
            195                 200                 205
Tyr Lys Glu Asp Lys Leu Asn Glu Lys Phe Asn Gly Leu Phe Thr Asp
    210                 215                 220

Ser Ser Met Asn Lys Val Ser Glu Glu Phe Asn Thr Leu Glu Lys Leu
225                 230                 235                 240

Asn Ala Phe Glu Asn Glu Leu Lys Asp His Pro Met Tyr Asp Leu Tyr
                245                 250                 255

Lys Glu Gly Leu Asn Asn Ala Arg Ala Ile Leu Thr Glu Thr Ser Glu
                260                 265                 270

Asn Pro Thr Lys Ala Thr Leu Gly Gln Ile Thr Tyr Asn Leu Asn Asp
            275                 280                 285

Asp Tyr Asn Asn Gln Tyr Arg Met Pro Tyr Thr Asn Ile Lys Ser Ile
        290                 295                 300

Lys Asn Asn Gly Arg His Tyr Ala Ala Gln Asn Ile Glu Lys Ala Ile
305                 310                 315                 320

Asp Asn Asp Val Asn Thr Tyr Trp Glu Thr Gly Thr Leu Asn Ser Ser
                325                 330                 335

Ser Phe Asn Asn Glu Val Glu Val Phe Asn Asp Leu Val Thr Leu
                340                 345                 350

Asp Arg Ile Val Tyr Gly Ser Arg Gln Ser Asp Leu Lys Gly Phe Ala
            355                 360                 365

Glu Glu Val Tyr Ile Tyr Ala Ser Arg Thr Ser Lys Gly Asp Thr Tyr
        370                 375                 380

Lys Leu Val Ala Thr Gly Ala His Glu Ala Thr Lys Gly Leu Val Glu
385                 390                 395                 400

Ala Lys Phe Glu Pro Thr Glu Phe Lys Arg Val Lys Phe Lys Phe Lys
                405                 410                 415

Lys Ser Lys Gln Asn Ser Ala Thr Leu Asn Glu Leu Met Phe Tyr Lys
            420                 425                 430

Pro Asp Glu Val Tyr Ser Ser Ile Pro Lys Leu Phe Thr Asp Gly Thr
        435                 440                 445

Met Ser Glu Leu Ser Glu Glu Phe Asn Ser Leu Glu Lys Ile Asn Ala
450                 455                 460

Phe Lys Glu Lys Ala Lys Asn His Pro Leu Tyr Asn Asp Phe Lys Glu
465                 470                 475                 480

Thr Ile Asp Leu Ala Glu Ser Leu Ile Ser Asn Pro Arg Lys Glu Asp
                485                 490                 495

Val Leu Glu Leu Glu Met Arg Gly Asp Ser Ile Ser Glu Ala Lys Lys
            500                 505                 510

Arg Lys Val Trp Asn Phe Gln Asp Trp Gln Ile Thr Gly Leu Ser Ala
        515                 520                 525

Arg Ala Gly Asp Lys Ile Thr Val Tyr Val Asp Val Ala Glu Gly Asp
530                 535                 540

Pro Thr Pro Thr Leu Leu Tyr Lys Gln Ser Leu Thr Gln His Gly Gly
545                 550                 555                 560

Ala Thr Ser Phe Gln Leu Lys Pro Gly Lys Asn Glu Ile Thr Ile Pro
                565                 570                 575

Glu Ile Asn Tyr Glu Ser Asn Gly Ile Pro Lys Asp Val Ile Gln Gly
            580                 585                 590

Gly Asp Leu Phe Phe Thr Asn Tyr Lys Ser Asp Ser Gln Lys Arg Ala
        595                 600                 605

Pro Lys Val Arg Ile Glu Gly Ala Ser Lys Tyr Pro Val Phe Ile Leu
    610                 615                 620
```

-continued

```
Gly Lys Ser Asp Glu Asn Glu Val Met Lys Glu Leu Glu Ala Tyr Val
625                 630                 635                 640

Glu Lys Ile Lys Ala Glu Pro Lys Thr Thr Pro Asn Ile Phe Ala Val
            645                 650                 655

Ser Ser Asn Lys Ser Leu Glu Phe Val Gln Ala Thr Tyr Ala Leu Asp
            660                 665                 670

Trp Tyr Lys Lys Asn Asn Lys Thr Pro Lys Tyr Thr Ala Glu Gln Trp
        675                 680                 685

Asp Gln Tyr Ile Ala Asp Ala Met Gly Phe Trp Gly Phe Asp Asn Ser
    690                 695                 700

Lys Asp Val Asn Ser Asp Phe Asn Phe Arg Ile Met Pro Met Val Lys
705                 710                 715                 720

Asn Leu Ser Gly Gly Ala Phe Met Asn Ala Gly Asn Gly Val Ile Gly
            725                 730                 735

Ile Arg Pro Gly Asn Gln Asp Ala Ile Leu Ala Ala Asn Lys Gly Trp
            740                 745                 750

Gly Val Ala His Glu Leu Gly His Asn Phe Asp Thr Gly Gly Arg Thr
            755                 760                 765

Ile Val Glu Val Thr Asn Asn Met Met Pro Leu Phe Phe Glu Ser Lys
770                 775                 780

Tyr Lys Thr Lys Thr Arg Ile Thr Asp Gln Asn Ile Trp Glu Asn Asn
785                 790                 795                 800

Thr Tyr Pro Lys Val Gly Leu Asp Asp Tyr Ser Asn Asn Glu Leu Tyr
            805                 810                 815

Asn Lys Ala Asp Ser Thr His Leu Ala Gln Leu Ala Pro Leu Trp Gln
            820                 825                 830

Leu Tyr Leu Tyr Asp Asn Thr Phe Tyr Gly Lys Phe Glu Arg Gln Phe
    835                 840                 845

Arg Glu Arg Asp Phe Gly Asn Lys Asn Arg Glu Asp Ile Tyr Lys Ser
    850                 855                 860

Trp Val Val Ala Ala Ser Asp Ala Met Glu Leu Asp Leu Thr Glu Phe
865                 870                 875                 880

Phe Ala Arg His Gly Ile Arg Val Asp Asp Lys Val Lys Glu Asp Leu
            885                 890                 895

Ala Lys Tyr Pro Lys Pro Asp Lys Lys Ile Tyr Tyr Leu Asn Asp Leu
            900                 905                 910

Ala Met Asn Tyr Lys Gly Asp Gly Phe Thr Asp Asn Ala Lys Val Ser
    915                 920                 925

Val Ser Thr Ser Gly Ser Asn Gly Asn Ile Lys Leu Ser Phe Ser Val
    930                 935                 940

Asp Asp Glu Asn Lys Asp Asn Ile Leu Gly Tyr Glu Ile Arg Arg Asp
945                 950                 955                 960

Gly Lys Tyr Val Gly Phe Thr Ser Asn Asp Ser Phe Val Asp Thr Lys
            965                 970                 975

Ser Asn Leu Asp Glu Asp Gly Val Tyr Val Val Thr Pro Tyr Asp Arg
            980                 985                 990

Lys Leu Asn Thr Leu Asn Pro Ile  Glu Val Asn Ala Leu  Gln Pro Thr
            995                 1000                1005

Leu Ser Val Asn Pro Val Ile  Thr Leu Ala Leu Gly  Glu Glu Phe
    1010                1015                1020

Asn Glu Glu Glu Tyr Ile Val  Ala Lys Asp Ile Lys  Gly Asn Ser
    1025                1030                1035

Leu Ser Glu Ser Val Lys Val  Lys Ser Ser Asn Val  Asn Thr Ser
    1040                1045                1050
```

```
Lys Val Gly Glu Tyr Glu Val Leu Tyr Ser Leu Glu Asp Ser Lys
1055                1060                1065

Gly Asn Glu Tyr Thr Lys Thr Ser Lys Val Asn Val Val Ser Arg
1070                1075                1080

Lys Glu Tyr Met Ser Asp Leu Thr Pro Lys Gln Ser Ser Asn Gly
1085                1090                1095

Trp Gly Thr Val Arg Lys Asp Lys Ser Ile Ser Gly Gly Val Ile
1100                1105                1110

Gly Leu Thr Arg Asp Gly Asp Phe Val Asp Tyr Asn Lys Gly Leu
1115                1120                1125

Gly Leu His Ser Asn Ala Glu Tyr Val Tyr Asp Leu Glu Gly Lys
1130                1135                1140

Asp Tyr Asp Tyr Phe Glu Ser Tyr Val Gly Val Asp Lys Ala Met
1145                1150                1155

Ser Ser Arg Pro Ala Ser Ser Val Ile Phe Lys Val Leu Val Asp
1160                1165                1170

Gly Glu Glu Lys Phe Asn Ser Gly Val Met Arg Ser Thr Thr Pro
1175                1180                1185

Gln Lys Tyr Val Lys Val Asp Val Lys Asn Ala Lys Glu Leu Lys
1190                1195                1200

Leu Ile Val Asn Asp Ala Gly Asp Gly Asp Ser Ser Asp His Ala
1205                1210                1215

Ser Phe Gly Asp Ala Lys Leu Ala Thr Leu Ser Ser Lys Pro Ile
1220                1225                1230

Ile Lys Gly Glu Asn Leu Ala Tyr Asn Met Asp Glu Lys Val Asp
1235                1240                1245

Leu Met Lys Gly Ile Thr Ala Thr Asp Ile Glu Asp Gly Asn Ile
1250                1255                1260

Thr Ser Lys Ile Gln Ile Lys Ser Ser Asp Phe Val Glu Gly Lys
1265                1270                1275

Ser Gly Ile Phe Lys Val Val Tyr Ser Val Thr Asp Ser Asp Gly
1280                1285                1290

Leu Thr Ser Glu Cys Ser Arg Thr Ile Ala Val Thr Asp Lys Glu
1295                1300                1305

Thr Gln Leu Ser Asp Leu Asn Trp Lys Ser Ala Thr Ile Gly Ser
1310                1315                1320

Gly Ser Val Arg Lys Asp Arg Ala Val Ser Gly Asn Gln Ile Arg
1325                1330                1335

Leu Leu Asn Glu Asp Asn Ser Val Gln Thr Phe Ala Lys Gly Ile
1340                1345                1350

Gly Thr His Ser Tyr Ser Glu Ile Val Tyr Asn Ser Glu Gly Tyr
1355                1360                1365

Asp Ile Phe Asp Thr Trp Val Gly Ile Asp Arg His Val Ala Asp
1370                1375                1380

Lys Lys Val Ser Ser Val Lys Phe Lys Val Tyr Val Asp Gly Glu
1385                1390                1395

Leu Lys Ala Glu Thr Asp Val Met Arg Ile Asp Thr Pro Lys Lys
1400                1405                1410

Arg Leu Val Val Asp Val Arg Asn Ser Lys Glu Ile Lys Leu Val
1415                1420                1425

Val Asp Val Ala Asp Asn Gly Asn Thr Trp Asp His Ala Asp Trp
1430                1435                1440

Ala Asp Ala Lys Phe Arg Asn Leu Ala Glu Tyr Asp Thr Thr Glu
```

-continued

```
              1445                1450                1455

Leu Asn  Lys Ala Leu Glu Glu  Ala Lys Lys Leu Asp  Leu Asn Asn
    1460                1465                1470

Tyr Thr  Glu Glu Ser Phe Glu  Ala Leu Lys Asn Ala  Ile Ser Lys
    1475                1480                1485

Gly Glu  Glu Ala Leu Leu Ser  Lys Asp Lys Glu Thr  Ile Asn Ser
    1490                1495                1500

Ala Leu  Glu Glu Leu Asn Lys  Ala Met Asp Ser Leu  Val Lys Val
    1505                1510                1515

Asp Leu  Asn Ala Val Ile Asn  Ile Pro Asp Lys Tyr  Leu Leu Lys
    1520                1525                1530

Ser Ile  Gln Asn Gln Leu Asn  Lys Thr Gly Asp Ile  Thr Leu Gly
    1535                1540                1545

Asp Met  Tyr Ser Leu Thr Thr  Leu Thr Leu Ser Gly  Val Glu Asp
    1550                1555                1560

Leu Ser  Gly Leu Glu Asn Ala  Lys Asn Leu Glu Thr  Leu Asn Met
    1565                1570                1575

Asp Tyr  Asn Glu Val Lys Asp  Leu Arg Pro Leu Ser  Lys Leu Lys
    1580                1585                1590

Lys Leu  Asn Thr Leu Asn Ala  Gln Glu Gln Phe Ile  Ala Ala Gly
    1595                1600                1605

Glu Leu  Lys Pro Ser Asn Gly  Lys Val Ile Gly Asp  Ser Lys Val
    1610                1615                1620

Tyr Asn  Arg Glu Gly Lys Asn  Val Ala Lys Thr Ile  Arg Val Val
    1625                1630                1635

Asp Lys  Asn Gly Asn Thr Ile  Leu Glu Gln Asp Ala  Lys Asp Glu
    1640                1645                1650

Phe Thr  Ile Asn Thr Lys Asp  Leu Ser Ser Gly Leu  Tyr Gly Val
    1655                1660                1665

His Val  Leu Phe Glu Asp Gly  Phe Ser Gly Val Met  Phe Tyr
    1670                1675                1680

Leu Phe  Asn Val
    1685

<210> SEQ ID NO 2
<211> LENGTH: 1171
<212> TYPE: PRT
<213> ORGANISM: Clostridium perfringens

<400> SEQUENCE: 2

Met Ala Met Arg Lys Met Lys Thr Met Asp Gly Asn Thr Ala Ala Ala
1               5                   10                  15

Tyr Ile Ser Tyr Ala Phe Thr Asp Val Ala Ala Ile Phe Pro Ile Thr
                20                  25                  30

Pro Ser Ser Pro Met Ala Glu Trp Val Asp Glu Asn Ser Ala Arg Gly
            35                  40                  45

Leu Lys Asn Ile Phe Gly Gln Pro Val Lys Val Met Glu Met Gln Ser
        50                  55                  60

Glu Ala Gly Ala Ala Gly Ala Val His Gly Ser Leu Gln Ala Gly Ala
65                  70                  75                  80

Leu Thr Thr Thr Tyr Thr Ala Ser Gln Gly Leu Leu Leu Met Ile Pro
                85                  90                  95

Asn Met Tyr Lys Ile Ala Gly Glu Leu Leu Pro Ser Val Phe His Val
                100                 105                 110

Ser Ala Arg Ala Leu Ala Thr Ser Ala Leu Asn Ile Phe Gly Asp His
```

```
            115                 120                 125
Gln Asp Val Met Ala Ala Arg Gln Thr Gly Phe Ala Met Leu Ala Glu
        130                 135                 140
Gly Ser Val Gln Glu Val Met Asp Leu Ser Ala Val Ala His Leu Ala
145                 150                 155                 160
Ala Leu Lys Ala Arg Ile Pro Phe Val Asn Phe Asp Gly Phe Arg
                165                 170                 175
Thr Ser His Glu Ile Gln Lys Val Glu Leu Leu Gln Tyr Asp Glu Leu
                180                 185                 190
Lys Glu Leu Val Asp Met Glu Ala Val Glu Glu Phe Arg Arg Arg Ala
            195                 200                 205
Leu Asn Pro Asn Lys Pro Val Thr Arg Gly Thr Ala Gln Asn Pro Asp
        210                 215                 220
Ile Tyr Phe Gln Glu Arg Glu Ala Val Asn Lys Phe Tyr Asp Ala Val
225                 230                 235                 240
Pro Glu Ile Val Glu Ser Tyr Met Lys Glu Ile Thr Lys Leu Thr Gly
                245                 250                 255
Arg Glu Tyr Asn Cys Phe Asp Tyr Tyr Gly Ala Ala Asp Ala Glu Arg
                260                 265                 270
Val Ile Val Ala Met Gly Ser Val Thr Asp Leu Ile Glu Glu Thr Val
            275                 280                 285
Asp Tyr Leu Asn Ala Lys Gly Glu Lys Val Gly Leu Ile Lys Val Arg
        290                 295                 300
Leu Phe Arg Pro Phe Ser Asn Glu Arg Leu Ile Lys Ala Met Pro Lys
305                 310                 315                 320
Thr Val Lys Lys Val Ala Val Leu Asp Arg Thr Lys Glu Pro Gly Ala
                325                 330                 335
Ala Gly Glu Pro Leu Tyr Leu Glu Val Lys Asn Ala Phe Tyr Gly Leu
                340                 345                 350
Glu Asn Ala Pro Val Ile Val Gly Gly Arg Phe Gly Leu Gly Ser Lys
            355                 360                 365
Asp Thr Val Pro Ala Asp Ile Val Ala Val Tyr Glu Asn Leu Asn Lys
        370                 375                 380
Glu Asp Ala Lys Asn Gly Phe Thr Leu Ser Ile Val Asp Asp Val Thr
385                 390                 395                 400
Asn Thr Ser Leu Glu Pro Val Gly Asp Ile Asp Thr Thr Pro Glu Gly
                405                 410                 415
Thr Lys Ala Cys Lys Phe Trp Gly Leu Gly Ser Asp Gly Thr Val Gly
                420                 425                 430
Ala Asn Lys Ser Ala Ile Lys Ile Ile Gly Asp His Thr Asp Met Tyr
            435                 440                 445
Ala Gln Gly Tyr Phe Ala Tyr Asp Ser Lys Lys Ser Gly Gly Val Thr
        450                 455                 460
Ile Ser His Leu Arg Phe Gly Lys Gln Pro Ile Lys Ser Pro Tyr Leu
465                 470                 475                 480
Ile Asn Lys Ala Asp Phe Val Ala Cys His Asn Gln Ser Tyr Val Asn
                485                 490                 495
Lys Tyr Phe Val Leu Asp Gly Leu Lys Lys Asn Gly Thr Phe Leu Leu
                500                 505                 510
Asn Thr Ile Trp Thr Pro Glu Glu Val Ala Glu His Leu Pro Ala Ser
            515                 520                 525
Tyr Lys Arg Phe Leu Ala Glu Asn Asn Ile Lys Phe Tyr Thr Leu Asn
        530                 535                 540
```

```
Ala Val Lys Ile Ala Gln Glu Val Gly Leu Gly Arg Ile Asn Met
545                 550                 555                 560

Ile Met Gln Ser Ala Phe Phe Lys Leu Ala Asn Ile Ile Pro Val Glu
            565                 570                 575

Asp Ala Val Lys Tyr Leu Lys Asp Ala Val Val Thr Ser Tyr Gly Lys
            580                 585                 590

Lys Gly Glu Lys Val Val Asn Met Asn His Ala Ala Ile Asp Lys Gly
            595                 600                 605

Ile Asp Ala Ile Val Glu Ile Thr Val Pro Ala Glu Trp Ala Asn Ala
610                 615                 620

Lys Asp Glu Val Val Glu Ala Lys Glu Val Pro Ala Phe Ile Lys Asn
625                 630                 635                 640

Ile Val Glu Pro Met Asn Arg Leu Glu Gly Asp Lys Leu Pro Val Ser
                645                 650                 655

Ala Phe Asn Gly Met Glu Asp Gly Thr Phe Glu Pro Gly Thr Ala Ala
                660                 665                 670

Tyr Glu Lys Arg Gly Ile Gly Ile Asn Ile Pro Glu Trp Ile Ala Asp
            675                 680                 685

Asn Cys Ile Gln Cys Asn Gln Cys Ala Tyr Val Cys Pro His Ala Thr
690                 695                 700

Ile Arg Pro Phe Leu Leu Thr Glu Glu Ala Lys Asn Ala Pro Ala
705                 710                 715                 720

Ser Thr Lys Leu Val Ala Ala Lys Ala Leu Lys Thr Glu Pro Met
                725                 730                 735

Gln Phe Thr Met Ala Val Ser Thr Leu Asp Cys Thr Cys Gly Asn
            740                 745                 750

Cys Ala Gln Val Cys Pro Ala Lys Glu Lys Ala Leu Val Met Lys Pro
            755                 760                 765

Gln His Thr Gln Glu Asp Gln Ile Glu Ala Trp Asp Tyr Cys Val Asn
            770                 775                 780

Asp Val Val Pro Lys Lys Asn Pro Met Asn Lys Asn Thr Val Lys Gly
785                 790                 795                 800

Ser Gln Phe Glu Gln Pro Leu Phe Glu Phe Ser Gly Ala Cys Ala Gly
                805                 810                 815

Cys Gly Glu Thr Pro Tyr Ala Lys Leu Ile Thr Gln Leu Phe Gly Asp
            820                 825                 830

Arg Met Met Ile Ala Asn Ala Thr Gly Cys Ser Ser Ile Trp Gly Gly
            835                 840                 845

Ser Ala Pro Ser Thr Pro Tyr Thr Thr Asn His Asn Gly His Gly Pro
850                 855                 860

Ala Trp Ala Asn Ser Leu Phe Glu Asp Asn Ala Glu Phe Gly Leu Gly
865                 870                 875                 880

Met Phe Leu Gly Val Lys Ala Ile Arg Glu Arg Leu Val Asp Leu Ala
                885                 890                 895

Gly Lys Ala Ile Glu Ala Gly Val Lys Pro Glu Ala Lys Glu Ala Leu
            900                 905                 910

Glu Ala Trp Ile Ala Glu Val Asp Asn Gly Glu Gly Thr Arg Asp Arg
            915                 920                 925

Ala Asp Ala Val Val Ala Ala Leu Gln Gly Glu Thr Asn Glu Phe Ala
930                 935                 940

Lys Glu Ile Leu Lys Asp Gln Asp Tyr Leu Ala Lys Arg Ser Gln Trp
945                 950                 955                 960

Ile Phe Gly Gly Asp Gly Trp Ala Tyr Asp Ile Gly Tyr Gly Gly Val
                965                 970                 975
```

Asp His Val Leu Ala Ser Gly Glu Asp Val Asn Ile Leu Val Met Asp
            980                 985                 990

Thr Glu Ile Tyr Ser Asn Thr Gly Gly Gln Ala Ser Lys Ser Thr Pro
        995                 1000                1005

Thr Ala Ala Ile Ala Lys Phe Ala Ala Ala Gly Lys Arg Thr Lys
    1010                1015                1020

Lys Lys Asp Leu Gly Met Met Ala Met Ser Tyr Gly Tyr Val Tyr
    1025                1030                1035

Val Ala Gln Ile Ala Met Gly Ala Asp Lys Asn Gln Thr Leu Lys
    1040                1045                1050

Ala Ile Ala Glu Ala Glu Ala Tyr Lys Gly Pro Ser Leu Ile Ile
    1055                1060                1065

Ala Tyr Ala Pro Cys Ile Ser His Gly Leu Lys Ala Gly Met Gly
    1070                1075                1080

Asn Ser Gln Leu Glu Glu Lys Arg Ala Val Glu Cys Gly Tyr Trp
    1085                1090                1095

Ala Met Tyr Arg Phe Asn Pro Met Leu Lys Glu Thr Gly Lys Asn
    1100                1105                1110

Pro Phe Ser Leu Asp Ser Lys Glu Pro Thr Gly Asp Phe Arg Glu
    1115                1120                1125

Phe Ile Met Gly Glu Val Arg Tyr Ala Ala Leu Ala Lys Ala Phe
    1130                1135                1140

Pro Glu Ala Ala Glu Ala Leu Phe Glu Lys Thr Glu Arg Asp Ala
    1145                1150                1155

Lys Glu Arg Leu Glu Asn Tyr Lys Lys Leu Ala Ala Asn
    1160                1165                1170

<210> SEQ ID NO 3
<211> LENGTH: 688
<212> TYPE: PRT
<213> ORGANISM: Clostridium perfringens

<400> SEQUENCE: 3

Met Ala Arg Gln Tyr Pro Leu Glu Lys Phe Arg Asn Phe Gly Ile Met
1               5                   10                  15

Ala His Ile Asp Ala Gly Lys Thr Thr Thr Thr Glu Arg Ile Leu Phe
            20                  25                  30

Tyr Thr Gly Arg Asn His Lys Ile Gly Glu Thr His Asp Gly Ala Ser
        35                  40                  45

Thr Met Asp Trp Met Ala Gln Glu Gln Glu Arg Gly Ile Thr Ile Thr
    50                  55                  60

Ser Ala Ala Thr Thr Cys Phe Trp Lys Gly Tyr Glu Leu Asn Ile Ile
65                  70                  75                  80

Asp Thr Pro Gly His Val Asp Phe Thr Val Glu Val Glu Arg Ser Leu
                85                  90                  95

Arg Val Leu Asp Gly Ala Val Thr Val Leu Asp Ala Lys Ser Gly Val
            100                 105                 110

Glu Pro Gln Thr Glu Thr Val Trp Arg Gln Ala Asp Lys Tyr Gly Val
        115                 120                 125

Pro Arg Met Ile Tyr Val Asn Lys Met Asp Ala Thr Gly Ala Asp Tyr
    130                 135                 140

Tyr Asn Cys Ile Asn Thr Val Arg Glu Arg Leu Gln Ala Asn Ala Val
145                 150                 155                 160

Ala Ile Gln Ile Pro Ile Gly Gln Glu Asp Gln Phe Gln Gly Met Val
                165                 170                 175

```
Asp Leu Leu Thr Asn Gln Ala Ile Ile Phe Lys Asp Asp Leu Gly Lys
            180                 185                 190

Asp Ile Glu Val Gly Glu Val Pro Ala Asp Leu Ala Asp Lys Ala Glu
        195                 200                 205

Glu Tyr Arg Ala Ala Met Ile Glu Ala Ile Ala Glu Thr Asp Glu Glu
210                 215                 220

Leu Met Met Lys Tyr Leu Glu Gly Glu Leu Thr Leu Glu Glu Leu
225                 230                 235                 240

Lys Val Ala Leu Arg Lys Ala Thr Ile Asn Asn Glu Ile Ile Pro Val
                245                 250                 255

Ile Cys Gly Ser Ser Tyr Lys Asn Lys Gly Val Gln Gln Met Ile Asp
                260                 265                 270

Gly Val Val Asp Tyr Leu Pro Ser Pro Leu Asp Ile Pro Ala Val Lys
                275                 280                 285

Gly Thr Asn Leu Asp Gly Glu Glu Val Arg Glu Ala Ser Asp Asp
            290                 295                 300

Ala Pro Met Ser Ala Leu Ala Phe Lys Ile Ala Thr Asp Pro Phe Val
305                 310                 315                 320

Gly Arg Leu Ala Phe Thr Arg Val Tyr Ser Gly Val Leu Glu Ser Gly
                325                 330                 335

Ser Tyr Val Leu Asn Ser Thr Lys Gly Lys Lys Glu Arg Ile Gly Arg
                340                 345                 350

Leu Val Lys Met His Ala Asn Ser Arg Glu Glu Val Glu Ser Leu Glu
            355                 360                 365

Ala Ala Glu Leu Gly Ala Val Ile Gly Leu Lys Asn Thr Thr Thr Gly
370                 375                 380

Asp Thr Leu Cys Thr Glu Ala Pro Ile Ile Leu Glu Lys Met Glu
385                 390                 395                 400

Phe Pro Glu Pro Val Ile Ser Ile Ala Ile Glu Pro Lys Thr Lys Ala
                405                 410                 415

Gly Gln Glu Lys Met Gly Ile Ala Leu Ser Lys Leu Ala Glu Glu Asp
            420                 425                 430

Pro Thr Phe Lys Thr Trp Thr Asp Gln Glu Thr Gly Gln Thr Ile Ile
            435                 440                 445

Ala Gly Met Gly Glu Leu His Leu Asp Ile Ile Val Asp Arg Leu Gln
450                 455                 460

Arg Glu Phe Lys Val Glu Cys Asn Val Gly Ala Pro Gln Val Ala Tyr
465                 470                 475                 480

Lys Glu Thr Ile Lys Lys Ala Val Glu Ala Glu Ala Lys Phe Ala Arg
                485                 490                 495

Gln Ser Gly Gly Arg Gly Gln Tyr Gly His Cys Lys Ile Glu Met Ile
            500                 505                 510

Pro Thr Glu Gly Glu Tyr Glu Phe Glu Asn Ala Ile Val Gly Gly Ala
            515                 520                 525

Ile Pro Arg Glu Tyr Ile Pro Ala Val Asp Asn Gly Ile Arg Glu Ala
            530                 535                 540

Ala Glu Ser Gly Ile Ile Ala Gly Tyr Pro Val Ile Asn Phe Lys Ile
545                 550                 555                 560

Arg Leu Phe Asp Gly Ser Tyr His Asp Val Asp Ser Ser Glu Met Ala
                565                 570                 575

Phe Lys Ile Ala Gly Ser Met Ala Phe Lys Asn Ala Met Ala Lys Ala
                580                 585                 590

Asp Ala Val Leu Leu Glu Pro Ile Met Lys Val Glu Ile Thr Val Pro
```

```
                      595                 600                 605
Glu Glu Tyr Met Gly Asp Val Ile Gly Asp Val Asn Ser Arg Arg Gly
610                 615                 620

Arg Met Glu Gly Met Asp Ser Arg Asn Gly Ala Gln Ile Ile Arg Ala
625                 630                 635                 640

Phe Ile Pro Leu Ser Glu Met Phe Gly Tyr Ala Thr Ala Leu Arg Ser
                645                 650                 655

Arg Thr Gln Gly Arg Gly Thr Tyr Ala Met Glu Phe Asp His Tyr Asp
                660                 665                 670

Asp Val Pro Lys Ser Ile Gln Glu Glu Val Ala Gly Lys Lys Asn Lys
                675                 680                 685

<210> SEQ ID NO 4
<211> LENGTH: 500
<212> TYPE: PRT
<213> ORGANISM: Clostridium perfringens

<400> SEQUENCE: 4

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
                20                  25                  30

Asp Lys Asn Gln Ser Ile Asp Ser Gly Ile Ser Ser Leu Ser Tyr Asn
            35                  40                  45

Arg Asn Glu Val Leu Ala Ser Asn Gly Asp Lys Ile Glu Ser Phe Val
        50                  55                  60

Pro Lys Glu Gly Lys Lys Thr Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125

Ile Asn Ile Asn Ile Asp Leu Pro Gly Leu Lys Gly Glu Asn Ser Ile
    130                 135                 140

Lys Val Asp Asp Pro Thr Tyr Gly Lys Val Ser Gly Ala Ile Asp Glu
145                 150                 155                 160

Leu Val Ser Lys Trp Asn Glu Lys Tyr Ser Ser Thr His Thr Leu Pro
                165                 170                 175

Ala Arg Thr Gln Tyr Ser Glu Ser Met Val Tyr Ser Lys Ser Gln Ile
            180                 185                 190

Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
    210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255

Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
        275                 280                 285

Asp Val Gln Ala Ala Phe Lys Ala Leu Ile Lys Asn Thr Asp Ile Lys
```

```
                        290                 295                 300
Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
                340                 345                 350

Thr Lys Asn Pro Ala Tyr Pro Ile Ser Tyr Thr Ser Val Phe Leu Lys
                355                 360                 365

Asp Asn Ser Val Ala Ala Val His Asn Lys Thr Asp Tyr Ile Glu Thr
                370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415

Lys Glu Gly Asn Glu Val Leu Thr His Lys Thr Trp Asp Gly Asn Tyr
                420                 425                 430

Gln Asp Lys Thr Ala His Tyr Ser Thr Val Ile Pro Leu Glu Ala Asn
                435                 440                 445

Ala Arg Asn Ile Arg Ile Lys Ala Arg Glu Cys Thr Gly Leu Ala Trp
                450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn
            500

<210> SEQ ID NO 5
<211> LENGTH: 332
<212> TYPE: PRT
<213> ORGANISM: Clostridium perfringens

<400> SEQUENCE: 5

Met Val Lys Val Ala Ile Asn Gly Phe Gly Arg Ile Gly Arg Leu Ala
1               5                   10                  15

Leu Arg Leu Met Ile Asp Asn Pro Glu Phe Glu Val Val Ala Ile Asn
                20                  25                  30

Asp Leu Thr Asp Ala Lys Thr Leu Ala His Leu Phe Lys Tyr Asp Ser
                35                  40                  45

Ala Gln Gly Arg Phe Asn Gly Glu Ile Glu Val Lys Glu Gly Ala Phe
            50                  55                  60

Val Val Asn Gly Lys Glu Ile Lys Val Thr Ala Lys Ser Asn Pro Ala
65                  70                  75                  80

Glu Leu Pro Trp Gly Glu Leu Gly Val Asp Val Val Leu Glu Cys Thr
                85                  90                  95

Gly Phe Phe Ala Ser Lys Glu Lys Ala Ser Ala His Leu Thr Ala Gly
                100                 105                 110

Ala Lys Lys Val Val Ile Ser Ala Pro Ala Gly Asn Asp Leu Pro Thr
            115                 120                 125

Val Val Tyr Asn Val Asn His Asp Ile Leu Asp Gly Ser Glu Asp Val
            130                 135                 140

Ile Ser Gly Ala Ser Cys Thr Thr Asn Cys Leu Ala Pro Met Ala Lys
145                 150                 155                 160

Ala Leu Asn Asp Asn Phe Gly Leu Asn Lys Gly Phe Met Thr Thr Ile
```

```
                       165                 170                 175
His Ala Tyr Thr Asn Asp Gln Asn Thr Leu Asp Ala Pro His Lys Lys
            180                 185                 190

Gly Asp Leu Arg Arg Ala Arg Ala Ala Ala Asn Ile Val Pro Asn
        195                 200                 205

Ser Thr Gly Ala Ala Lys Ala Ile Gly Leu Val Ile Pro Glu Leu Ala
    210                 215                 220

Gly Lys Leu Asp Gly Asn Ala Gln Arg Val Pro Val Ile Thr Gly Ser
225                 230                 235                 240

Leu Thr Glu Leu Val Cys Thr Leu Asp Lys Lys Val Thr Val Glu Glu
                245                 250                 255

Val Asn Ala Ala Met Lys Ala Ala Ser Asn Glu Ser Phe Gly Tyr Thr
            260                 265                 270

Glu Asp Pro Ile Val Ser Ser Asp Val Ile Gly Ile Ser Phe Gly Ser
        275                 280                 285

Leu Phe Asp Ala Thr Gln Thr Lys Ile Met Glu Val Asp Gly Gln Gln
    290                 295                 300

Leu Val Lys Val Ala Ser Trp Tyr Asp Asn Glu Ala Ser Tyr Thr Asn
305                 310                 315                 320

Gln Leu Ile Arg Thr Leu Lys Cys Leu Val Ser Lys
                325                 330

<210> SEQ ID NO 6
<211> LENGTH: 288
<212> TYPE: PRT
<213> ORGANISM: Clostridium perfringens

<400> SEQUENCE: 6

Met Ala Leu Val Asn Ala Lys Glu Met Leu Asn Lys Ala Arg Glu Gly
1               5                   10                  15

Lys Tyr Ala Val Gly Gln Phe Asn Ile Asn Asn Leu Glu Trp Thr Lys
            20                  25                  30

Ala Ile Leu Leu Thr Ala Gln Glu Asn Asn Ser Pro Val Ile Leu Gly
        35                  40                  45

Val Ser Glu Gly Ala Ala Lys Tyr Met Cys Gly Phe Lys Thr Ile Val
    50                  55                  60

Gly Met Val Asn Gly Met Leu Glu Glu Leu Lys Ile Thr Val Pro Val
65                  70                  75                  80

Ala Leu His Leu Asp His Gly Ser Tyr Gln Gly Ala Ile Asp Ala Met
                85                  90                  95

Asp Ala Gly Phe Ser Ser Val Met Phe Asp Gly Ser His Tyr Ser Ile
            100                 105                 110

Glu Glu Asn Ile Val Lys Thr Lys Glu Ile Ile Asn Leu Ala Ala Ala
        115                 120                 125

Lys Asn Val Ser Val Glu Ala Glu Val Gly Ser Ile Gly Gly Glu Glu
    130                 135                 140

Asp Gly Val Val Gly Ala Gly Glu Ile Ala Asp Pro Ala Glu Cys Lys
145                 150                 155                 160

Gln Ile Ala Glu Leu Gly Val Thr Met Leu Ala Ala Gly Ile Gly Asn
                165                 170                 175

Ile His Gly Lys Tyr Pro Ala Asn Trp Ala Gly Leu Asn Phe Glu Ala
            180                 185                 190

Leu Ala Asn Ile Lys Ala Ala Thr Gly Asp Met Pro Leu Val Leu His
        195                 200                 205

Gly Gly Thr Gly Ile Pro Ser Asp Met Ile Ala Glu Ala Ile Ser Leu
```

```
                210                 215                 220
Gly Val Ser Lys Ile Asn Val Asn Thr Glu Cys Gln Leu Ser Phe Ala
225                 230                 235                 240

Glu Ala Thr Arg Lys Tyr Ile Glu Ala Gly Lys Asp Leu Gly Lys
                245                 250                 255

Gly Phe Asp Pro Arg Lys Leu Leu Asn Pro Gly Phe Glu Ala Ile Lys
                260                 265                 270

Ala Thr Val Lys Glu Lys Met Glu Leu Phe Gly Ser Val Asn Arg Ala
                275                 280                 285

<210> SEQ ID NO 7
<211> LENGTH: 60
<212> TYPE: PRT
<213> ORGANISM: Clostridium perfringens

<400> SEQUENCE: 7

Ser Lys Asp Val Asn Ser Asp Phe Asn Phe Arg Ile Met Pro Met Val
1               5                   10                  15

Lys Asn Leu Ser Gly Gly Ala Phe Met Asn Ala Gly Asn Gly Val Ile
                20                  25                  30

Gly Ile Arg Pro Gly Asn Gln Asp Ala Ile Leu Ala Ala Asn Lys Gly
                35                  40                  45

Trp Gly Val Ala His Glu Leu Gly His Asn Phe Asp
    50                  55                  60

<210> SEQ ID NO 8
<211> LENGTH: 78
<212> TYPE: PRT
<213> ORGANISM: Clostridium perfringens

<400> SEQUENCE: 8

Tyr Asp Asn Thr Phe Tyr Gly Lys Phe Glu Arg Gln Phe Arg Glu Arg
1               5                   10                  15

Asp Phe Gly Asn Lys Asn Arg Glu Asp Ile Tyr Lys Ser Trp Val Val
                20                  25                  30

Ala Ala Ser Asp Ala Met Glu Leu Asp Leu Thr Glu Phe Phe Ala Arg
                35                  40                  45

His Gly Ile Arg Val Asp Asp Lys Val Lys Glu Asp Leu Ala Lys Tyr
    50                  55                  60

Pro Lys Pro Asp Lys Lys Ile Tyr Tyr Leu Asn Asp Leu Ala
65                  70                  75

<210> SEQ ID NO 9
<211> LENGTH: 54
<212> TYPE: PRT
<213> ORGANISM: Clostridium perfringens

<400> SEQUENCE: 9

Ile Lys Leu Ser Phe Ser Val Asp Asp Glu Asn Lys Asp Asn Ile Leu
1               5                   10                  15

Gly Tyr Glu Ile Arg Arg Asp Gly Lys Tyr Val Gly Phe Thr Ser Asn
                20                  25                  30

Asp Ser Phe Val Asp Thr Lys Ser Asn Leu Glu Asp Gly Val Tyr
        35                  40                  45

Val Val Thr Pro Tyr Asp
    50

<210> SEQ ID NO 10
<211> LENGTH: 12
```

```
<212> TYPE: PRT
<213> ORGANISM: Clostridium perfringens

<400> SEQUENCE: 10

Gly Tyr Phe Ala Tyr Asp Ser Lys Lys Ser Gly Gly
1               5                   10

<210> SEQ ID NO 11
<211> LENGTH: 12
<212> TYPE: PRT
<213> ORGANISM: Clostridium perfringens

<400> SEQUENCE: 11

Ser Tyr Val Asn Lys Tyr Phe Val Leu Asp Gly Leu
1               5                   10

<210> SEQ ID NO 12
<211> LENGTH: 12
<212> TYPE: PRT
<213> ORGANISM: Clostridium perfringens

<400> SEQUENCE: 12

Lys Asp Glu Val Val Glu Ala Lys Glu Val Pro Ala
1               5                   10

<210> SEQ ID NO 13
<211> LENGTH: 12
<212> TYPE: PRT
<213> ORGANISM: Clostridium perfringens

<400> SEQUENCE: 13

Ala Lys Glu Val Pro Ala Phe Ile Lys Asn Ile Val
1               5                   10

<210> SEQ ID NO 14
<211> LENGTH: 12
<212> TYPE: PRT
<213> ORGANISM: Clostridium perfringens

<400> SEQUENCE: 14

Ala Tyr Val Cys Pro His Ala Thr Ile Arg Pro Phe
1               5                   10

<210> SEQ ID NO 15
<211> LENGTH: 975
<212> TYPE: DNA
<213> ORGANISM: Clostridium perfringens

<400> SEQUENCE: 15
ttctggggat tgataactc aaaagatgtt aattcagatt ttaattttag aataatgcct      60
atggttaaaa accttagtgg tggagcattc atgaatgctg aaatggtgt tataggtata    120 agacctggaa atcaggatgc aatacttgca gctaataaag gatggggtgt tgctcatgaa    180
cttggacata actttgatac aggcggaaga accatagtag aagtaacaaa taatatgatg    240
ccattattct ttgagtctaa atataaaact aaaacaagaa taactgacca aaacatatgg    300
gaaaacaata cttaccctaa agttggctta gatgattatt ctaataatga gttatataat    360
aaggctgata gtactcattt agctcagtta gcgccattat ggcaattata tttatatgat    420
aatactttct atggaaagtt tgaaagacag tttagagaaa gagattttgg aaataaaaat    480
agagaagata tatataaatc ttgggttgtg gcagcgtcag atgctatgga gttagattta    540
actgagttct ttgcaagaca tggtattcgt gttgatgata aggttaagga ggatttagct    600
```

-continued

```
aagtatccaa agcctgataa aaagatctat tacttaaatg atttagcaat gaattataaa       660
ggtgatggat ttacggataa tgcaaaggta tctgtaagta caagtggttc aaatggtaat       720
ataaaacttt cattctcagt agatgatgaa aataaagata atatacttgg atatgaaata       780
cgcagagatg gaaagtatgt aggatttact tctaatgata gctttgttga tactaaatct       840
aatttagatg aggatggtgt atatgtagta acaccatatg atagaaagtt aaataccttg       900
aatccaatag aggtaaatgc attgcaacca actttatctg taaacccagt gattacacta       960
gctttaggtg aggag                                                        975
```

```
<210> SEQ ID NO 16
<211> LENGTH: 325
<212> TYPE: PRT
<213> ORGANISM: Clostridium perfringens

<400> SEQUENCE: 16
```

Phe Trp Gly Phe Asp Asn Ser Lys Asp Val Asn Ser Asp Phe Asn Phe
1               5                   10                  15

Arg Ile Met Pro Met Val Lys Asn Leu Ser Gly Gly Ala Phe Met Asn
            20                  25                  30

Ala Gly Asn Gly Val Ile Gly Ile Arg Pro Gly Asn Gln Asp Ala Ile
        35                  40                  45

Leu Ala Ala Asn Lys Gly Trp Gly Val Ala His Glu Leu Gly His Asn
    50                  55                  60

Phe Asp Thr Gly Gly Arg Thr Ile Val Glu Val Thr Asn Asn Met Met
65                  70                  75                  80

Pro Leu Phe Phe Glu Ser Lys Tyr Lys Thr Lys Thr Arg Ile Thr Asp
                85                  90                  95

Gln Asn Ile Trp Glu Asn Thr Tyr Pro Lys Val Gly Leu Asp Asp
            100                 105                 110

Tyr Ser Asn Asn Glu Leu Tyr Asn Lys Ala Asp Ser Thr His Leu Ala
        115                 120                 125

Gln Leu Ala Pro Leu Trp Gln Leu Tyr Leu Tyr Asp Asn Thr Phe Tyr
    130                 135                 140

Gly Lys Phe Glu Arg Gln Phe Arg Glu Arg Asp Phe Gly Asn Lys Asn
145                 150                 155                 160

Arg Glu Asp Ile Tyr Lys Ser Trp Val Val Ala Ala Ser Asp Ala Met
                165                 170                 175

Glu Leu Asp Leu Thr Glu Phe Phe Ala Arg His Gly Ile Arg Val Asp
            180                 185                 190

Asp Lys Val Lys Glu Asp Leu Ala Lys Tyr Pro Lys Pro Asp Lys Lys
        195                 200                 205

Ile Tyr Tyr Leu Asn Asp Leu Ala Met Asn Tyr Lys Gly Asp Gly Phe
    210                 215                 220

Thr Asp Asn Ala Lys Val Ser Val Ser Thr Ser Gly Ser Asn Gly Asn
225                 230                 235                 240

Ile Lys Leu Ser Phe Ser Val Asp Asp Glu Asn Lys Asp Asn Ile Leu
                245                 250                 255

Gly Tyr Glu Ile Arg Arg Asp Gly Lys Tyr Val Gly Phe Thr Ser Asn
            260                 265                 270

Asp Ser Phe Val Asp Thr Lys Ser Asn Leu Asp Glu Asp Gly Val Tyr
        275                 280                 285

Val Val Thr Pro Tyr Asp Arg Lys Leu Asn Thr Leu Asn Pro Ile Glu
    290                 295                 300

Val Asn Ala Leu Gln Pro Thr Leu Ser Val Asn Pro Val Ile Thr Leu

```
305                 310                 315                 320
Ala Leu Gly Glu Glu
                    325

<210> SEQ ID NO 17
<211> LENGTH: 10
<212> TYPE: PRT
<213> ORGANISM: Clostridium perfringens

<400> SEQUENCE: 17

Gly Val Ala His Glu Leu Gly His Asn Phe
1               5                   10
```